United States Patent
Haze et al.

(10) Patent No.: US 6,635,751 B1
(45) Date of Patent: Oct. 21, 2003

(54) ISOLATED NUCLEIC ACIDS ENCODING ACTIVATED AND SUPPRESSIVE FORMS OF ATF6

(75) Inventors: Kyosuke Haze, Shizuoka (JP); Hiderou Yoshida, Shiga (JP); Kazutoshi Mori, Kyoto (JP); Hideki Yanagi, Tekarazuka (JP); Takashi Yura, Kyoto (JP)

(73) Assignee: HSP Research Institute, Inc., Osaka (JP)

( * ) Notice: Subject to any disclaimer, the term of this patent is extended or adjusted under 35 U.S.C. 154(b) by 0 days.

(21) Appl. No.: 09/831,642

(22) PCT Filed: Nov. 12, 1999

(86) PCT No.: PCT/JP99/06305

§ 371 (c)(1),
(2), (4) Date: Aug. 13, 2001

(87) PCT Pub. No.: WO00/29429

PCT Pub. Date: May 25, 2000

(30) Foreign Application Priority Data

Nov. 13, 1998 (JP) .............................................. 10-324227
Jun. 9, 1999 (JP) ........................................... 11-163112

(51) Int. Cl.$^7$ ............................................. C12N 15/12
(52) U.S. Cl. .................................................... 536/23.5
(58) Field of Search ............................... 536/23.5, 23.1

(56) References Cited

PUBLICATIONS

Zhu et al., Molecular and Cellular Biology, vol. 17, No. 9, pp. 4957–4966 (1997).
Hai et al., Genes and Development, vol. 3, pp. 2083–2090 (1989).
Min et al., Genomics, vol. 30, pp. 149–156 (1996).
Yoshida et al., The Journal of Biological Chemistry, vol. 273, No. 50, pp. 33741–33749 (1998).
Roy et al., Nucleic Acids Research, vol. 27, No. 6, pp. 1437–1443 (1999).
Roy et al., The Journal of Biological Chemistry, vol. 271, No. 46, pp. 28995–29002 (1996).
Lee, Current Opinion in Cell Biology 1992, 4:267–273.
Kozutsumi et al., Nature, vol. 332, pp. 462–464 (Mar. 31, 1988).
Lee, Trends in Biochem. Sci., 12, 20–23 (1987).
Resendez, Jr. et al., Molecular and Cellular Biology, vol. 8, No. 10, pp. 4579–4584 (Oct. 1988).
Wooden et al., Molecular and Cellular Biology, vol. 11, No. 11, pp. 5612–5623 (Nov. 1991).
Li et al., Molecular and Cellular Biology, vol. 14, No. 8, pp. 5533–5546 (Aug. 1994).
Mori et al., Genes to Cells, 1, 803–817 (1996).
Cai et al., Journal of Cellular Physiology, 154:229–237 (1993).
Sugawara et al., Cancer Research, 53, 6001–6005 (Dec. 15, 1993).
Jamora et al., Proc. Natl. Acad. Sci. USA, vol. 93, pp. 7690–7694 (Jul. 1996).
Tsukamoto et al., J. Clin. Invest., vol. 98, No. 8, pp. 1930–1941 (Oct. 1996).
Welsch et al., Cell, vol. 73, pp. 1251–1254 (Jul. 2, 1993).
Denning et al., Nature, vol. 358, pp. 761–764 (Aug. 27, 1992).
Wang et al., Neurochem. Int., vol. 23, No. 6, pp. 575–582 (1993).
Higashi et al., Brain Research, 650 (1994) 239–248.
Lowenstein et al., Molecular Brain Research, 22 (1994) 299–308.
Little et al., Neuroscience, vol. 75, No. 1, pp. 209–219 (1996).
Kuwabara et al., The Journal of Biological Chemistry, vol. 271, No. 9, pp. 5025–5032 (1996).
Yoshida et al., The Journal of Biological Chemistry, vol. 273, No. 50, pp. 33741–33749 (1998).

Primary Examiner—Terry McKelvey
(74) Attorney, Agent, or Firm—Birch, Stewart, Kolasch & Birch, LLP

(57) ABSTRACT

A factor capable of efficiently regulating expression of an endoplasmic chaperone gene, a nucleic acid encoding it, a complementary strand nucleic acid thereof, a method for regulating expression of an endoplasmic reticulum chaperone gene, and a method for expressing a foreign gene is provided. The endoplasmic reticulum stress transcription factor is capable of regulating transcription-inducing activity, wherein the transcription-inducing activity is exhibited by an element having the nucleotide sequence shown in SEQ ID NO:1 or an element having a nucleotide sequence resulting from substitution of 1 to 3 bases with other bases in the nucleotide sequence as shown in SEQ ID NO:1. A method for controlling expression of an endoplasmic reticulum chaperone, comprising expressing the factor; a method for expressing a foreign protein, comprising positively regulating expression of an endoplasmic reticulum chaperone gene by the method for controlling expression; and a nucleic acid encoding activated form of ATF6, activated form of CREB-RP, suppressive form of ATF6, or suppressive form of CREB-RP, or the complementary strand thereto are also provided. It is expected to be applied to treatment or prophylaxis of cancers, arteriosclerosis, cystic fibrosis, ischemic diseases, wounds or ulcers.

2 Claims, 32 Drawing Sheets

```
                    |-------ERSE------|
                    CCAAT.........CCACG (-139)   GAGGGGGCCGCTTCGAATCGGCGGCGGCCAGC     (-108)
(-107)   TTGGTGGCGTGGGCCAATGAACGGCCTCCAACG    (-75)
(-74)    AGCAGGGCCTTCACCAATCGGCGGCCTCCACGA    (-42)
```

FIG. 2

| | | | |
|---|---|---|---|
| GRP78 | ERSE1 | (human) | CCAATCGGCGGCCTCCACG |
| | ERSE1 | (murine) | CCAATCGGAGGCCTCCACG |
| | ERSE1 | (rat) | CCAATCGGAGGCCTCCACG |
| GRP94 | ERSE1 | (human) | CCAATCGCGCCGCACCACG |
| | ERSE1 | (chicken) | CCAATGGGAGCGCACCACG |
| | ERSE3 | (human) | CCAATCGGAAGGAGCCACG |
| | ERSE3 | (chicken) | CCAATCGACGCCGGCCACG |
| CRT | ERSE3 | (human) | CCAATGATGGTCGACCACG |
| | ERSE3 | (murine) | CCAATGAGGGTCGACCACG |
| | | | |
| GRP78 | ERSE2 | (human) | CCAATGAACGGCCTCCAAC |
| | ERSE2 | (murine) | CCAATCAGCGGCCTCCAAC |
| | ERSE2 | (rat) | CCAACCAGCGGCCTCCAAC |
| | ERSE3 | (human) | CGAATCGGCGGCGGCCAGC |
| | ERSE3 | (murine) | CGAATCGGCAGCAGCCAGC |
| | ERSE3 | (rat) | CGAATCGGCAGCGGCCAGC |
| GRP94 | ERSE2 | (human) | CCAATCGGAGCTGTCCAGG |
| | ERSE2 | (chicken) | CCAATCGTGGCTTTCCATG |
| | ERSE4 | (human) | CCAATCAAATGGCTCCGCG |
| CRT | ERSE1 | (human) | CCAATGACAAAGTGGCAGG |
| | ERSE2 | (human) | CCAATAGAAATCGGCCATC |
| | ERSE2 | (murine) | CCAATAGAAATCAGCCATC |
| ERp72 | ERSE1 | (murine) | CCAATCAGAAGGGGCACC |
| | ERSE2 | (murine) | CCAATCACGGGCTGCCACT |
| PDI | ERSE1 | (human) | CCAGTCAGAATGCAACACG |
| | ERSE2 | (human) | CCAACTGGCACGCCCCCG |
| GRP58 | ERSE1 | (human) | CCAATCAGCGGCTGCCACA |

FIG. 3

| | | | | |
|---|---|---|---|---|
| Dm | CRT | ERSE1 | | CCAATGAAAACGTTCCAGC |
| | | ERSE2 | | CCAATCAGGGATGTCTACG |
| Ce | GRP78 | ERSE1 | | CCAATCGGCGACGGCCGTG |
| | GRP78 | ERSE2 | | CCTATCGTCCTAGGCCACG |
| At | GRP78 | ERSE1 | | CCAATCAGGTTTTAACTCG |
| | CRT | ERSE1 | | CCAATAGGTAACCGACACG |
| | CRT | ERSE2 | | CCAATACTAACGCCATG |
| So | GRP78 | ERSE1 | | GGAATATCATTGGTCCACG |
| Rc | CRT | ERSE1 | -185 | CCAATCGTATTATGCCATG |
| | CRT | ERSE2 | -243 | CAAATACGATATTACCACG |
| | CRT | ERSE3 | -314 | CCCCTCATAGCACGCCACG |
| | CRT | ERSE4 | -1695 | CCATTCTTTGCTGCTCACG |
| An | GRP78 | ERSE1 | | CCAATTGAGCAGCTCGTCG |

F I G. 5

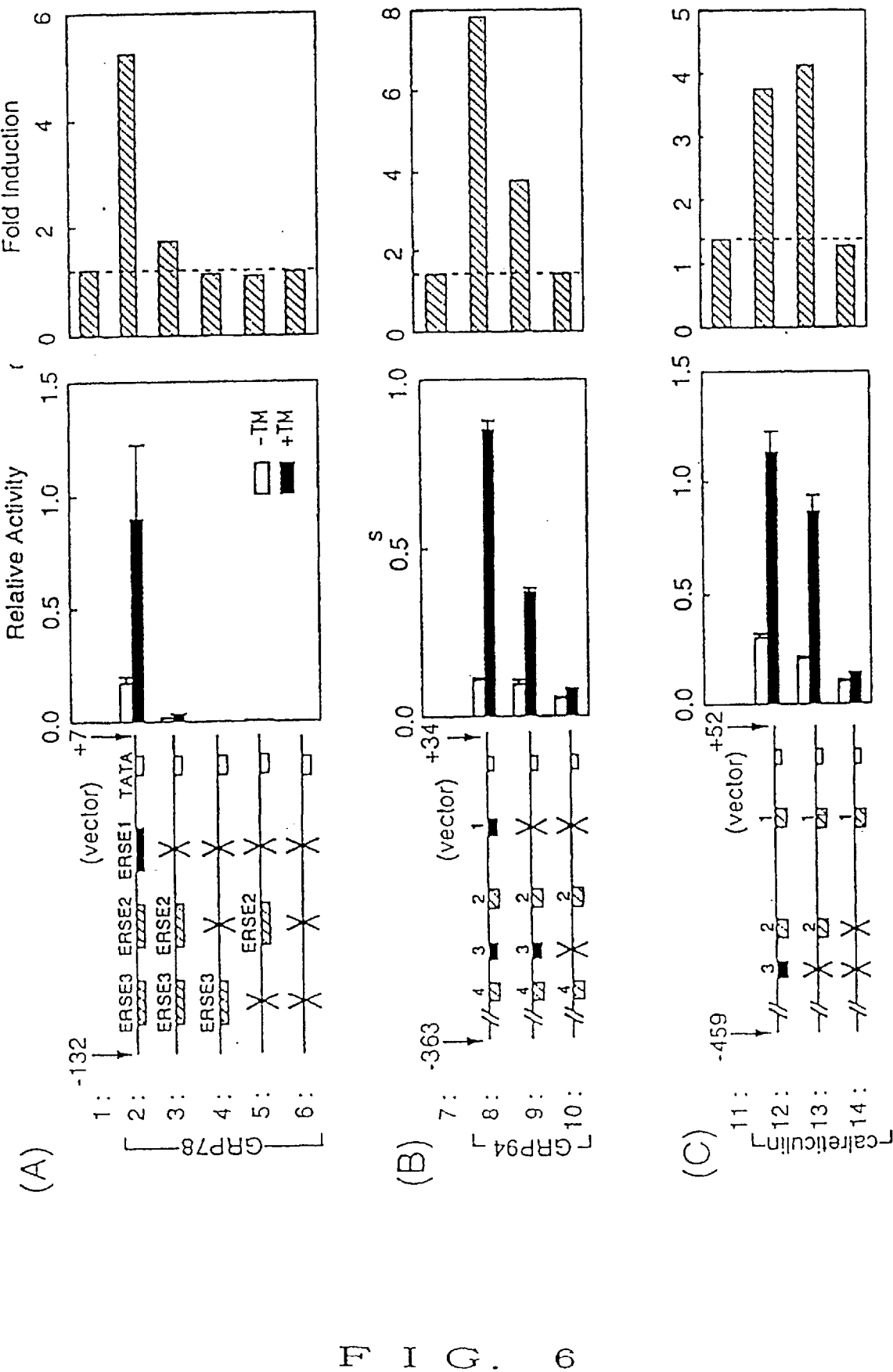
F I G. 6

(A)

| | |
|---|---|
| ATF6 | RRQQRMIKNRESACQSRKKKKEY |
| Hac1 | RRIERILRNRRAAHQSREKKRLH |

(B)

| | |
|---|---|
| ATF6 | RRQQRMIKNRESACQSRKKKKEY |
| CREB-RP/G13 | KRQQRMIKNRESACQSRRKKKEY |
| CREB | KREVRLMKNREAARECRRKKKEY |
| ATF1 | KREIRLMKNREAARECRRKKKEY |
| CRE-BP1/ATF2 | KRRKFLERNRAAASRCRQKRKVW |
| ATF3 | RKKRRRERNKIAAAKCRNKKKEK |
| ATF4 | KKLKKMEQNKTAATRYRQKKRAE |
| c-fos(ATF5) | EKENPKERNKMAAAKCRNRRREL |

(C)

| | |
|---|---|
| ATF6 | RRQQRMIKNRESACQSRKKKKEY |
| GBF4 | QRQKRMIKNRESAARSRERKQAY |
| DPBF1 | RRQRRMIKNRESAARSRARKQAY |
| DPBF2 | RRQKRMIKNRESAARSRARKQAY |
| C2546 | RRQRRMIKNRESAARSRARKQAY |

FIG. 13

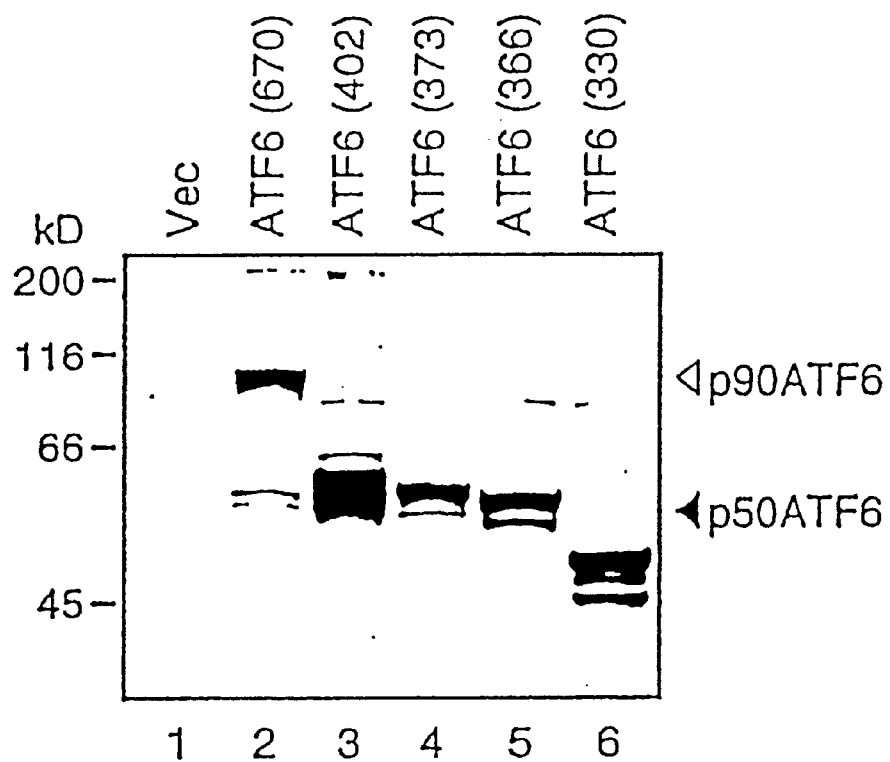
F I G. 2 6

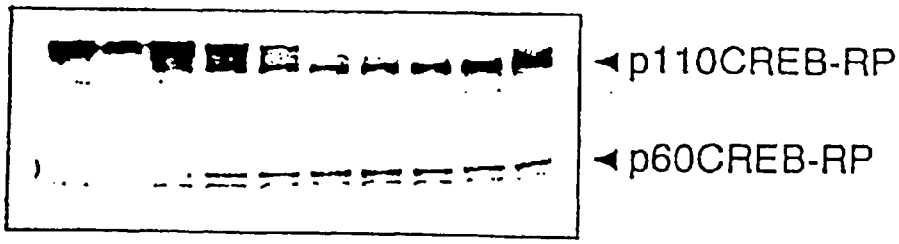
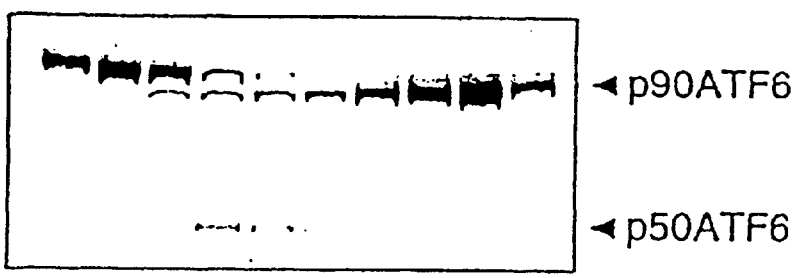
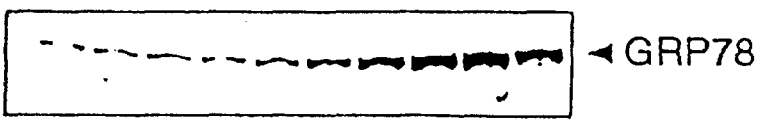
FIG. 29

SEQUENCE LISTING

```
<160> NUMBER OF SEQ ID NOS: 83

<210> SEQ ID NO 1
<211> LENGTH: 19
<212> TYPE: DNA
<213> ORGANISM: Artificial Sequence
<220> FEATURE:
<223> OTHER INFORMATION: ERSE1 consensus sequence
<221> NAME/KEY: misc_feature
<222> LOCATION: (5)..(14)
<223> OTHER INFORMATION: "n" is A, T, C, or G

<400> SEQUENCE: 1
ccaatnnnnn nnnnccacg                                               19

<210> SEQ ID NO 2
<211> LENGTH: 19
<212> TYPE: DNA
<213> ORGANISM: Artificial Sequence
<220> FEATURE:
<223> OTHER INFORMATION: ERSE2 consensus sequence
<221> NAME/KEY: misc_feature
<222> LOCATION: (5)..(14)
<223> OTHER INFORMATION: "n" is A, T, C, or G

<400> SEQUENCE: 2
ccaatnnnnn nnnnccaac                                               19

<210> SEQ ID NO 3
<211> LENGTH: 19
<212> TYPE: DNA
<213> ORGANISM: Artificial Sequence
<220> FEATURE:
<223> OTHER INFORMATION: ERSE3 consensus sequence
<221> NAME/KEY: misc_feature
<222> LOCATION: (5)..(14)
<223> OTHER INFORMATION: "n" is A, T, C, or G

<400> SEQUENCE: 3
cgaatnnnnn nnnnccagc                                               19

<210> SEQ ID NO 4
<211> LENGTH: 122
<212> TYPE: DNA
<213> ORGANISM: Homo sapiens

<400> SEQUENCE: 4 ggaggggggcc gcttcgaatc ggcggcggcc agcttggtgg cctgggccaa tgaacggcct    60
ccaacgagca gggccttcac caatcggcgg cctccacgac ggggctgggg gagggtatat   120
aa                                                                 122

<210> SEQ ID NO 5
<211> LENGTH: 19
<212> TYPE: DNA
<213> ORGANISM: Homo sapiens

<400> SEQUENCE: 5
ccaatcggcg gcctccacg                                               19

<210> SEQ ID NO 6
<211> LENGTH: 19
<212> TYPE: DNA
<213> ORGANISM: Murine
```

```
<400> SEQUENCE: 6
ccaatcggag gcctccacg                                              19

<210> SEQ ID NO 7
<211> LENGTH: 19
<212> TYPE: DNA
<213> ORGANISM: Rat

<400> SEQUENCE: 7
ccaatcggag gcctccacg                                              19

<210> SEQ ID NO 8
<211> LENGTH: 19
<212> TYPE: DNA
<213> ORGANISM: Homo sapiens

<400> SEQUENCE: 8
ccaatcgcgc cgcaccacg                                              19

<210> SEQ ID NO 9
<211> LENGTH: 19
<212> TYPE: DNA
<213> ORGANISM: Chicken

<400> SEQUENCE: 9
ccaatgggag cgcaccacg                                              19

<210> SEQ ID NO 10
<211> LENGTH: 19
<212> TYPE: DNA
<213> ORGANISM: Homo sapiens

<400> SEQUENCE: 10
ccaatcggaa ggagccacg                                              19

<210> SEQ ID NO 11
<211> LENGTH: 19
<212> TYPE: DNA
<213> ORGANISM: Chicken

<400> SEQUENCE: 11
ccaatcgacg ccggccacg                                              19

<210> SEQ ID NO 12
<211> LENGTH: 19
<212> TYPE: DNA
<213> ORGANISM: Homo sapiens

<400> SEQUENCE: 12
ccaatgatgg tcgaccacg                                              19

<210> SEQ ID NO 13
<211> LENGTH: 19
<212> TYPE: DNA
<213> ORGANISM: Murine

<400> SEQUENCE: 13
ccaatgaggg tcgaccacg                                              19

<210> SEQ ID NO 14
<211> LENGTH: 19
<212> TYPE: DNA
<213> ORGANISM: Homo sapiens
```

-continued

```
<210> SEQ ID NO 15
<211> LENGTH: 19
<212> TYPE: DNA
<213> ORGANISM: Murine

<400> SEQUENCE: 15
ccaatcagcg gcctccaac                                                19

<210> SEQ ID NO 16
<211> LENGTH: 19
<212> TYPE: DNA
<213> ORGANISM: Rat

<400> SEQUENCE: 16
ccaaccagcg gcctccaac                                                19

<210> SEQ ID NO 17
<211> LENGTH: 19
<212> TYPE: DNA
<213> ORGANISM: Homo sapiens

<400> SEQUENCE: 17
cgaatcggcg gcggccagc                                                19

<210> SEQ ID NO 18
<211> LENGTH: 19
<212> TYPE: DNA
<213> ORGANISM: Murine

<400> SEQUENCE: 18
cgaatcggca gcagccagc                                                19

<210> SEQ ID NO 19
<211> LENGTH: 19
<212> TYPE: DNA
<213> ORGANISM: Rat

<400> SEQUENCE: 19
cgaatcggca gcggccagc                                                19

<210> SEQ ID NO 20
<211> LENGTH: 19
<212> TYPE: DNA
<213> ORGANISM: Homo sapiens

<400> SEQUENCE: 20
ccaatcggag ctgtccagg                                                19

<210> SEQ ID NO 21
<211> LENGTH: 19
<212> TYPE: DNA
<213> ORGANISM: Chicken

<400> SEQUENCE: 21
ccaatcgtgg ctttccatg                                                19

<210> SEQ ID NO 22
<211> LENGTH: 19
<212> TYPE: DNA
```

<400> SEQUENCE: 14
ccaatgaacg gcctccaac                                                19

```
<213> ORGANISM: Homo sapiens

<400> SEQUENCE: 22
ccaatcaaat ggctccgcg                                                19

<210> SEQ ID NO 23
<211> LENGTH: 19
<212> TYPE: DNA
<213> ORGANISM: Homo sapiens

<400> SEQUENCE: 23
ccaatgacaa agtggcagg                                                19

<210> SEQ ID NO 24
<211> LENGTH: 19
<212> TYPE: DNA
<213> ORGANISM: Homo sapiens

<400> SEQUENCE: 24
ccaatagaaa tcggccatc                                                19

<210> SEQ ID NO 25
<211> LENGTH: 19
<212> TYPE: DNA
<213> ORGANISM: Murine

<400> SEQUENCE: 25
ccaatagaaa tcagccatc                                                19

<210> SEQ ID NO 26
<211> LENGTH: 19
<212> TYPE: DNA
<213> ORGANISM: Murine

<400> SEQUENCE: 26
ccaatcagaa gggggcacc                                                19

<210> SEQ ID NO 27
<211> LENGTH: 19
<212> TYPE: DNA
<213> ORGANISM: Murine

<400> SEQUENCE: 27
ccaatcacgg gctgccact                                                19

<210> SEQ ID NO 28
<211> LENGTH: 19
<212> TYPE: DNA
<213> ORGANISM: Rat

<400> SEQUENCE: 28
ccagtcagaa tgcaacacg                                                19

<210> SEQ ID NO 29
<211> LENGTH: 19
<212> TYPE: DNA
<213> ORGANISM: Rat

<400> SEQUENCE: 29
ccaactggca cgcccccccg                                               19

<210> SEQ ID NO 30
<211> LENGTH: 19
```

<212> TYPE: DNA
<213> ORGANISM: Homo sapiens

<400> SEQUENCE: 30

| ccaatcagcg gctgccaca | 19 |

<210> SEQ ID NO 31
<211> LENGTH: 2509
<212> TYPE: DNA
<213> ORGANISM: Homo sapiens

<400> SEQUENCE: 31

| tttttgtccg cctgccgccg ccgtcccaga tattaatcac ggagttccag ggagaaggaa | 60 |
| cttgtgaaat gggggagccg gctggggttg ccggcaccat ggagtcacct tttagcccgg | 120 |
| gactctttca caggctggat gaagattggg attctgctct ctttgctgaa cttggttatt | 180 |
| tcacagacac tgatgagctg caattggaag cagcaaatga cgtatgaa aacaattttg | 240 |
| ataatcttga ttttgatttg gatttgatgc cttgggagtc agacatttgg gacatcaaca | 300 |
| accaaatctg tacagttaaa gatattaagg cagaacccca gccactttct ccagcctcct | 360 |
| caagttattc agtctcatct cctcggtcag tggactctta ttcttcaact cagcatgttc | 420 |
| ctgaggagtt ggatttgtct tctagttctc agatgtctcc cctttcctta tatggtgaaa | 480 |
| actctaatag tctctcttca ccggagccac tgaaggaaga taagcctgtc actggttcta | 540 |
| ggaacaagac tgaaaatgga ctgactccaa agaaaaaaat tcaggtgaat tcaaaacctt | 600 |
| caattcagcc caagccttta ttgcttccag cagcacccaa gactcaaaca aactccagtg | 660 |
| ttccagcaaa aaccatcatt attcagacag taccaacgct tatgccattg caaagcagc | 720 |
| aaccaattat cagtttacaa cctgcaccca ctaaaggcca gacggttttg ctgtctcagc | 780 |
| ctactgtggt acaacttcaa gcacctggag ttctgccctc tgctcagcca gtccttgctg | 840 |
| ttgctggggg agtcacacag ctccctaatc acgtggtgaa tgtggtacca gccccttcag | 900 |
| cgaatagccc agtgaatgga aaactttccg tgactaaacc tgtcctacaa gtaccatga | 960 |
| gaaatgtcgg ttcagatatt gctgtgctaa ggagacagca acgtatgata aaaaatcgag | 1020 |
| aatccgcttg tcagtctcgc aagaagaaga agaatatat gctagggtta gaggcgagat | 1080 |
| taaaggctgc cctctcagaa aacgagcaac tgaagaaaga aaatggaaca ctgaagcggc | 1140 |
| agctggatga agttgtgtca gagaaccaga ggcttaaagt ccctagtcca aagcgaagag | 1200 |
| ttgtctgtgt gatgatagta ttggcattta taatactgaa ctatgaccct atgagcatgt | 1260 |
| tggaacagga ttccaggaga atgaaccta gtgtgagccc tgcaaatcaa aggaggcacc | 1320 |
| ttctaggatt ttctgctaaa gaggcacagg acacatcaga tggtattatc cagaaaaaca | 1380 |
| gctacagata tgatcattct gtttcaaatg acaaagccct gatggtgcta actgaagaac | 1440 |
| cattgcttta cattcctcca cctccttgtc agccctaat taacacaaca gagtctctca | 1500 |
| ggttaaatca tgaacttcga ggatgggttc atagacatga agtagaaagg accaagtcaa | 1560 |
| gaagaatgac aaataatcaa cagaaaaccc gtattcttca gggtgctctg aacagggct | 1620 |
| caaattctca gctgatggct gttcaataca cagaaaccac tagtagtatc agcaggaact | 1680 |
| cagggagtga gctacaagtg tattatgctt cacccagaag ttatcaagac ttttttgaag | 1740 |
| ccatccgcag aaggggagac acattttatg ttgtgtcatt tcgaagggat cacctgctgt | 1800 |
| taccagctac cacccataac aagaccacaa gaccaaaaat gtcaattgtg ttaccagcaa | 1860 |
| taaacataaa tgagaatgtg atcaatgggc aggactacga agtgatgatg cagattgact | 1920 |

-continued

```
gtcaggtgat ggacaccagg atcctccata tcaaaagttc gtcagttcct ccttacctcc    1980
gagatcagca gaggaatcaa accaacacct tctttggctc ccctcccgca gccacagagg    2040
caacccacgt tgtcagcacc atccctgagt cattacaata gcaccctgca gctatgctgg    2100
aaaactgagc gtgggaccct gccagactga agagcaggtg agcaaaatgc tgctttctgc    2160
cttggtggca ggcagagaac tgtctcgtac tagaattcaa ggaggaaaga agaagaaata    2220
aaagaagctg ctccattttt catcatctac ccatctattt ggaaagcact ggaattcaga    2280
tgcaagagaa caatgtttct tcagtggcaa atgtagccct gcatcctcca gtgttacctg    2340
gtgtagattt ttttttctgt acctttctaa acctctcttc cctctgtgat ggttttgtgt    2400
ttaaacaatc atcttctttt aaataatatc cacctctcct ttttgccatt tcacttattg    2460
attcataaag tgaattttat ttaaagctat gccacacatg catgttcaa               2509
```

<210> SEQ ID NO 32
<211> LENGTH: 670
<212> TYPE: PRT
<213> ORGANISM: Homo sapiens

<400> SEQUENCE: 32

```
Met Gly Glu Pro Ala Gly Val Ala Gly Thr Met Glu Ser Pro Phe Ser
1               5                   10                  15

Pro Gly Leu Phe His Arg Leu Asp Glu Asp Trp Asp Ser Ala Leu Phe
            20                  25                  30

Ala Glu Leu Gly Tyr Phe Thr Asp Thr Asp Glu Leu Gln Leu Glu Ala
        35                  40                  45

Ala Asn Glu Thr Tyr Glu Asn Asn Phe Asp Asn Leu Asp Phe Asp Leu
    50                  55                  60

Asp Leu Met Pro Trp Glu Ser Asp Ile Trp Asp Ile Asn Asn Gln Ile
65                  70                  75                  80

Cys Thr Val Lys Asp Ile Lys Ala Glu Pro Gln Pro Leu Ser Pro Ala
                85                  90                  95

Ser Ser Ser Tyr Ser Val Ser Ser Pro Arg Ser Val Asp Ser Tyr Ser
            100                 105                 110

Ser Thr Gln His Val Pro Glu Glu Leu Asp Leu Ser Ser Ser Ser Gln
        115                 120                 125

Met Ser Pro Leu Ser Leu Tyr Gly Glu Asn Ser Asn Ser Leu Ser Ser
    130                 135                 140

Pro Glu Pro Leu Lys Glu Asp Lys Pro Val Thr Gly Ser Arg Asn Lys
145                 150                 155                 160

Thr Glu Asn Gly Leu Thr Pro Lys Lys Lys Ile Gln Val Asn Ser Lys
                165                 170                 175

Pro Ser Ile Gln Pro Lys Pro Leu Leu Leu Pro Ala Ala Pro Lys Thr
            180                 185                 190

Gln Thr Asn Ser Ser Val Pro Ala Lys Thr Ile Ile Ile Gln Thr Val
        195                 200                 205

Pro Thr Leu Met Pro Leu Ala Lys Gln Gln Pro Ile Ile Ser Leu Gln
    210                 215                 220

Pro Ala Pro Thr Lys Gly Gln Thr Val Leu Leu Ser Gln Pro Thr Val
225                 230                 235                 240

Val Gln Leu Gln Ala Pro Gly Val Leu Pro Ser Ala Gln Pro Val Leu
                245                 250                 255

Ala Val Ala Gly Gly Val Thr Gln Leu Pro Asn His Val Val Asn Val
            260                 265                 270
```

-continued

```
Val Pro Ala Pro Ser Ala Asn Ser Pro Val Asn Gly Lys Leu Ser Val
            275                 280                 285

Thr Lys Pro Val Leu Gln Ser Thr Met Arg Asn Val Gly Ser Asp Ile
        290                 295                 300

Ala Val Leu Arg Arg Gln Gln Arg Met Ile Lys Asn Arg Glu Ser Ala
305                 310                 315                 320

Cys Gln Ser Arg Lys Lys Lys Glu Tyr Met Leu Gly Leu Glu Ala
                325                 330                 335

Arg Leu Lys Ala Ala Leu Ser Glu Asn Glu Gln Leu Lys Lys Glu Asn
                340                 345                 350

Gly Thr Leu Lys Arg Gln Leu Asp Glu Val Val Ser Glu Asn Gln Arg
            355                 360                 365

Leu Lys Val Pro Ser Pro Lys Arg Val Val Cys Val Met Ile Val
        370                 375                 380

Leu Ala Phe Ile Ile Leu Asn Tyr Gly Pro Met Ser Met Leu Glu Gln
385                 390                 395                 400

Asp Ser Arg Arg Met Asn Pro Ser Val Ser Pro Ala Asn Gln Arg Arg
                405                 410                 415

His Leu Leu Gly Phe Ser Ala Lys Glu Ala Gln Asp Thr Ser Asp Gly
                420                 425                 430

Ile Ile Gln Lys Asn Ser Tyr Arg Tyr Asp His Ser Val Ser Asn Asp
            435                 440                 445

Lys Ala Leu Met Val Leu Thr Glu Pro Leu Leu Tyr Ile Pro Pro
450                 455                 460

Pro Pro Cys Gln Pro Leu Ile Asn Thr Thr Glu Ser Leu Arg Leu Asn
465                 470                 475                 480

His Glu Leu Arg Gly Trp Val His Arg His Glu Val Glu Arg Thr Lys
                485                 490                 495

Ser Arg Arg Met Thr Asn Asn Gln Gln Lys Thr Arg Ile Leu Gln Gly
                500                 505                 510

Ala Leu Glu Gln Gly Ser Asn Ser Gln Leu Met Ala Val Gln Tyr Thr
            515                 520                 525

Glu Thr Thr Ser Ser Ile Ser Arg Asn Ser Gly Ser Glu Leu Gln Val
530                 535                 540

Tyr Tyr Ala Ser Pro Arg Ser Tyr Gln Asp Phe Phe Glu Ala Ile Arg
545                 550                 555                 560

Arg Arg Gly Asp Thr Phe Tyr Val Val Ser Phe Arg Arg Asp His Leu
                565                 570                 575

Leu Leu Pro Ala Thr Thr His Asn Lys Thr Thr Arg Pro Lys Met Ser
            580                 585                 590

Ile Val Leu Pro Ala Ile Asn Ile Asn Glu Asn Val Ile Asn Gly Gln
        595                 600                 605

Asp Tyr Glu Val Met Met Gln Ile Asp Cys Gln Val Met Asp Thr Arg
    610                 615                 620

Ile Leu His Ile Lys Ser Ser Val Pro Pro Tyr Leu Arg Asp Gln
625                 630                 635                 640

Gln Arg Asn Gln Thr Asn Thr Phe Phe Gly Ser Pro Pro Ala Ala Thr
                645                 650                 655

Glu Ala Thr His Val Val Ser Thr Ile Pro Glu Ser Leu Gln
            660                 665                 670
```

<210> SEQ ID NO 33
<211> LENGTH: 2620
<212> TYPE: DNA

<213> ORGANISM: Homo sapiens

<400> SEQUENCE: 33

| | | | | | |
|---|---|---|---|---|---|
| ggcgggcctt | gggaaccgtc | tcctggttgt | ggggtggggg | ggaaagatgg | cggagctgat | 60 |
| gctgctcagc | gagattgctg | acccgacgcg | tttcttcacc | gacaacctgc | ttagcccgga | 120 |
| ggactgggac | agcaccttgt | attctggcct | agatgaagtg | gccgaggagc | agacgcagct | 180 |
| cttccgttgc | ccggagcagg | atgtcccgtt | tgacggcagc | tccctggacg | tggggatgga | 240 |
| tgtcagcccc | tctgagcccc | catgggaact | cctgccgatc | ttcccagatc | ttcaggtgaa | 300 |
| gtctgagcca | tcttccccct | gctcttcctc | ctccctcagc | tccgagtcat | cgcgtctctc | 360 |
| cacagagcca | tccagcgagg | ctcttggggt | aggggaggtg | ctccatgtga | agacagagtc | 420 |
| cttggcaccc | ccactgtgtc | tcctgggaga | tgacccaaca | tcctcatttg | aaaccgtcca | 480 |
| gatcaacgtt | atccccacct | ctgatgattc | ctcagatgtc | cagaccaaga | tagaacctgt | 540 |
| ctctccatgt | tcttccgtca | actctgaggc | ctccctgctc | tcagccgact | cctccagcca | 600 |
| ggcttttata | ggagaggagg | tcctggaagt | gaagacagag | tccctgtccc | cttcaggatg | 660 |
| cctcctgtgg | gatgtcccag | cccctcact | tggagctgtc | cagatcagca | tgggcccatc | 720 |
| ccttgatggc | tcctcaggca | aagccctgcc | caccggaag | ccgccactgc | agcccaaacc | 780 |
| tgtagtgcta | accactgtcc | caatgccatc | cagagctgtg | cctcccagca | ccacagtcct | 840 |
| tctgcagtcc | ctcgtccagc | caccccccagt | gtccccagtt | gtcctcatcc | agggtgctat | 900 |
| tcgagtccag | cctgaagggc | cggctccctc | tctaccacgg | cctgagagga | agagcatcgt | 960 |
| tcccgctcct | atgcctggaa | actcctgccc | gcctgaagtg | gatgcaaagc | tgctgaagcg | 1020 |
| gcagcagcga | atgatcaaga | accgggagtc | agcctgccag | tcccggagaa | agaagaaaga | 1080 |
| gtatctgcag | ggactggagg | ctcggctgca | agcagtactg | gctgacaacc | agcagctccg | 1140 |
| ccgagagaat | gctgccctcc | ggcggcggct | ggaggccctg | ctggctgaaa | acagcgagct | 1200 |
| caagttaggg | tctggaaaca | ggaaggtggt | ctgcatcatg | gtcttccttc | tcttcattgc | 1260 |
| cttcaacttt | ggacctgtca | gcatcagtga | gcctccttca | gctcccatct | ctcctcggat | 1320 |
| gaacaagggg | gagcctcaac | cccggagaca | cttgctgggg | ttctcagagc | aagagccagt | 1380 |
| tcagggagtt | gaacctctcc | agggtcctc | ccagggccct | aaggagcccc | agcccagccc | 1440 |
| cacagaccag | cccagtttca | gcaacctgac | agccttccct | gggggcgcca | aggagctact | 1500 |
| actaagagac | ctagaccagc | tcttcctctc | tctctgattgc | cggcacttca | accgcactga | 1560 |
| gtccctgagg | cttgctgacg | agttgagtgg | ctgggtccag | cgccaccaga | gaggccggag | 1620 |
| gaagatccct | cagagggccc | aggagagaca | gaagtctcag | ccacgaagaa | agtcacctcc | 1680 |
| agttaaggca | gtccccatcc | aaccccctgg | accccagaa | agggattctg | tgggccagct | 1740 |
| gcaactatat | cgccacccag | accgttcgca | gccagcattc | ttggatgcaa | ttgaccgacg | 1800 |
| ggaagacaca | ttttatgttg | tctctttccg | aaggggccac | ctgctgctcc | cagccatcag | 1860 |
| ccacaacaag | acctcccggc | caagatgtc | cctggtgatg | cctgccatgg | ccccaatga | 1920 |
| gaccctgtca | ggccgtgggg | cccgggggga | ctatgaggag | atgatgcaga | tcgagtgtga | 1980 |
| ggtcatggac | accagggtga | ttcacatcaa | gacctccaca | gtgcccccct | cgctccgaaa | 2040 |
| acagccatcc | ccaaccccag | gcaatgccac | aggtggcccc | ttgccagtct | ctgcagccag | 2100 |
| ccaggcccac | caggcctccc | accagcccct | ctacctcaat | catccctgac | ctctgccatt | 2160 |
| cacactgact | tagaacgggg | ggaggggggta | ccaggtggcc | aggtgggact | gtttcaaatt | 2220 |
| tccctgatcc | ccaggcttgg | ggcaattggt | aaaggaaaga | gcaggtgtgg | gggttaagca | 2280 |

-continued

```
cttatttgag gtgggggtgt tcacctctct tctcatccct ttatcagaat ataggggctcc    2340 tctcattcct gtgaacccc agtcctggct tctttgtttg aggggattgt gtgaggttca     2400
gttgtggggt gggtggtgag ctgctgcata ttttttattg tgtttctcta gtgttatggc    2460
agtggaggtg ggaatttagt ccccaggtgg gacaagggaa gttttttcat tttggagcta    2520
gttactggga gtaaggggag gtggggtggg ggggagttca ggtttatgtg tgtgcatttc    2580 tttttttatta ttactaaata aacaacttgg agggagttga                         2620
```

<210> SEQ ID NO 34
<211> LENGTH: 700
<212> TYPE: PRT
<213> ORGANISM: Homo sapiens

<400> SEQUENCE: 34

```
Met Ala Glu Leu Met Leu Ser Glu Ile Ala Asp Pro Thr Arg Phe
 1               5                  10                  15

Phe Thr Asp Asn Leu Leu Ser Pro Glu Asp Trp Asp Ser Thr Leu Tyr
                20                  25                  30

Ser Gly Leu Asp Glu Val Ala Glu Glu Gln Thr Gln Leu Phe Arg Cys
            35                  40                  45

Pro Glu Gln Asp Val Pro Phe Asp Gly Ser Ser Leu Asp Val Gly Met
        50                  55                  60

Asp Val Ser Pro Ser Glu Pro Pro Trp Glu Leu Leu Pro Ile Phe Pro
65                  70                  75                  80

Asp Leu Gln Val Lys Ser Glu Pro Ser Ser Pro Cys Ser Ser Ser Ser
                85                  90                  95

Leu Ser Ser Glu Ser Ser Arg Leu Ser Thr Glu Pro Ser Ser Glu Ala
            100                 105                 110

Leu Gly Val Gly Glu Val Leu His Val Lys Thr Glu Ser Leu Ala Pro
        115                 120                 125

Pro Leu Cys Leu Leu Gly Asp Asp Pro Thr Ser Ser Phe Glu Thr Val
    130                 135                 140

Gln Ile Asn Val Ile Pro Thr Ser Asp Asp Ser Ser Asp Val Gln Thr
145                 150                 155                 160

Lys Ile Glu Pro Val Ser Pro Cys Ser Ser Val Asn Ser Glu Ala Ser
                165                 170                 175

Leu Leu Ser Ala Asp Ser Ser Gln Ala Phe Ile Gly Glu Glu Val
            180                 185                 190

Leu Glu Val Lys Thr Glu Ser Leu Ser Pro Ser Gly Cys Leu Leu Trp
        195                 200                 205

Asp Val Pro Ala Pro Ser Leu Gly Ala Val Gln Ile Ser Met Gly Pro
    210                 215                 220

Ser Leu Asp Gly Ser Ser Gly Lys Ala Leu Pro Thr Arg Lys Pro Pro
225                 230                 235                 240

Leu Gln Pro Lys Pro Val Val Leu Thr Val Pro Met Pro Ser Arg
                245                 250                 255

Ala Val Pro Pro Ser Thr Thr Val Leu Leu Gln Ser Leu Val Gln Pro
            260                 265                 270

Pro Pro Val Ser Pro Val Val Leu Ile Gln Gly Ala Ile Arg Val Gln
        275                 280                 285

Pro Glu Gly Pro Ala Pro Ser Leu Pro Arg Pro Glu Arg Lys Ser Ile
    290                 295                 300

Val Pro Ala Pro Met Pro Gly Asn Ser Cys Pro Pro Glu Val Asp Ala
```

-continued

```
                305                 310                 315                 320
Lys Leu Leu Lys Arg Gln Gln Arg Met Ile Lys Asn Arg Glu Ser Ala
                325                 330                 335
Cys Gln Ser Arg Arg Lys Lys Glu Tyr Leu Gln Gly Leu Glu Ala
            340                 345                 350
Arg Leu Gln Ala Val Leu Ala Asp Asn Gln Gln Leu Arg Arg Glu Asn
                355                 360                 365
Ala Ala Leu Arg Arg Arg Leu Glu Ala Leu Leu Ala Glu Asn Ser Glu
        370                 375                 380
Leu Lys Leu Gly Ser Gly Asn Arg Lys Val Val Cys Ile Met Val Phe
385                 390                 395                 400
Leu Leu Phe Ile Ala Phe Asn Phe Gly Pro Val Ser Ile Ser Glu Pro
                405                 410                 415
Pro Ser Ala Pro Ile Ser Pro Arg Met Asn Lys Gly Glu Pro Gln Pro
            420                 425                 430
Arg Arg His Leu Leu Gly Phe Ser Glu Gln Glu Pro Val Gln Gly Val
        435                 440                 445
Glu Pro Leu Gln Gly Ser Ser Gln Gly Pro Lys Glu Pro Gln Pro Ser
450                 455                 460
Pro Thr Asp Gln Pro Ser Phe Ser Asn Leu Thr Ala Phe Pro Gly Gly
465                 470                 475                 480
Ala Lys Glu Leu Leu Leu Arg Asp Leu Asp Gln Leu Phe Leu Ser Ser
                485                 490                 495
Asp Cys Arg His Phe Asn Arg Thr Glu Ser Leu Arg Leu Ala Asp Glu
            500                 505                 510
Leu Ser Gly Trp Val Gln Arg His Gln Arg Gly Arg Arg Lys Ile Pro
        515                 520                 525
Gln Arg Ala Gln Glu Arg Gln Lys Ser Gln Pro Arg Lys Lys Ser Pro
        530                 535                 540
Pro Val Lys Ala Val Pro Ile Gln Pro Pro Gly Pro Pro Glu Arg Asp
545                 550                 555                 560
Ser Val Gly Gln Leu Gln Leu Tyr Arg His Pro Asp Arg Ser Gln Pro
                565                 570                 575
Ala Phe Leu Asp Ala Ile Asp Arg Arg Glu Asp Thr Phe Tyr Val Val
            580                 585                 590
Ser Phe Arg Arg Gly His Leu Leu Pro Ala Ile Ser His Asn Lys
        595                 600                 605
Thr Ser Arg Pro Lys Met Ser Leu Val Met Pro Ala Met Ala Pro Asn
        610                 615                 620
Glu Thr Leu Ser Gly Arg Gly Ala Pro Gly Asp Tyr Glu Glu Met Met
625                 630                 635                 640
Gln Ile Glu Cys Glu Val Met Asp Thr Arg Val Ile His Ile Lys Thr
                645                 650                 655
Ser Thr Val Pro Pro Ser Leu Arg Lys Gln Pro Ser Pro Thr Pro Gly
            660                 665                 670
Asn Ala Thr Gly Gly Pro Leu Pro Val Ser Ala Ala Ser Gln Ala His
        675                 680                 685
Gln Ala Ser His Gln Pro Leu Tyr Leu Asn His Pro
        690                 695                 700

<210> SEQ ID NO 35
<211> LENGTH: 29
<212> TYPE: DNA
<213> ORGANISM: Artificial Sequence
```

```
<220> FEATURE:
<223> OTHER INFORMATION: ERSEI sequence from the Human GRP78 promoter

<400> SEQUENCE: 35
ccttcaccaa tcggcggcct ccacgacgg                                              29

<210> SEQ ID NO 36
<211> LENGTH: 29
<212> TYPE: DNA
<213> ORGANISM: Homo sapiens

<400> SEQUENCE: 36
ccttcagact acggcggcct gatgtacgg                                              29

<210> SEQ ID NO 37
<211> LENGTH: 122
<212> TYPE: DNA
<213> ORGANISM: Homo sapiens

<400> SEQUENCE: 37 ggaggggggcc gcttcgaatc ggcggcggcc agcttggtgg cctgggccaa tgaacggcct          60
ccaacgagca gggccttcac caatcggcgg cctccacgac ggggctgggg gagggtatat         120
aa                                                                        122

<210> SEQ ID NO 38
<211> LENGTH: 32
<212> TYPE: DNA
<213> ORGANISM: Homo sapiens

<400> SEQUENCE: 38 gaggggggccg cttcgaatcg gcggcggcca gc                                        32

<210> SEQ ID NO 39
<211> LENGTH: 33
<212> TYPE: DNA
<213> ORGANISM: Homo sapiens

<400> SEQUENCE: 39
ttggtggcct gggccaatga acggcctcca acg                                        33

<210> SEQ ID NO 40
<211> LENGTH: 33
<212> TYPE: DNA
<213> ORGANISM: Homo sapiens

<400> SEQUENCE: 40
agcagggcct tcaccaatcg gcggcctcca cga                                        33

<210> SEQ ID NO 41
<211> LENGTH: 19
<212> TYPE: DNA
<213> ORGANISM: Drosophila melanogaster

<400> SEQUENCE: 41
ccaatgaaaa cgttccagc                                                        19

<210> SEQ ID NO 42
<211> LENGTH: 19
<212> TYPE: DNA
<213> ORGANISM: Drosophila melanogaster

<400> SEQUENCE: 42
```

-continued ccaatcaggg atgtctacg                                            19

<210> SEQ ID NO 43
<211> LENGTH: 19
<212> TYPE: DNA
<213> ORGANISM: Caenorhabditis elegans

<400> SEQUENCE: 43
ccaatcggcg acggccgtg                                            19

<210> SEQ ID NO 44
<211> LENGTH: 19
<212> TYPE: DNA
<213> ORGANISM: Caenorhabditis elegans

<400> SEQUENCE: 44
cctatcgtcc taggccacg                                            19

<210> SEQ ID NO 45
<211> LENGTH: 19
<212> TYPE: DNA
<213> ORGANISM: Arabidopsis thaliana

<400> SEQUENCE: 45
ccaatcaggt tttaactcg                                            19

<210> SEQ ID NO 46
<211> LENGTH: 19
<212> TYPE: DNA
<213> ORGANISM: Arabidopsis thaliana

<400> SEQUENCE: 46
ccaataggta accgacacg                                            19

<210> SEQ ID NO 47
<211> LENGTH: 19
<212> TYPE: DNA
<213> ORGANISM: Arabidopsis thaliana

<400> SEQUENCE: 47
ccaatactat aacgccatg                                            19

<210> SEQ ID NO 48
<211> LENGTH: 19
<212> TYPE: DNA
<213> ORGANISM: Spinacia oreracea

<400> SEQUENCE: 48
ggaatatcat tggtccacg                                            19

<210> SEQ ID NO 49
<211> LENGTH: 19
<212> TYPE: DNA
<213> ORGANISM: Ricinus communis

<400> SEQUENCE: 49
ccaatcgtat tatgccatg                                            19

<210> SEQ ID NO 50
<211> LENGTH: 19
<212> TYPE: DNA
<213> ORGANISM: Ricinus communis

<400> SEQUENCE: 50
caaatacgat attaccacg					19

<210> SEQ ID NO 51
<211> LENGTH: 19
<212> TYPE: DNA
<213> ORGANISM: Ricinus communis

<400> SEQUENCE: 51
cccctcatag cacgccacg					19

<210> SEQ ID NO 52
<211> LENGTH: 19
<212> TYPE: DNA
<213> ORGANISM: Ricinus communis

<400> SEQUENCE: 52
ccattctttg ctgctcacg					19

<210> SEQ ID NO 53
<211> LENGTH: 19
<212> TYPE: DNA
<213> ORGANISM: Aspergillus nigar

<400> SEQUENCE: 53
ccaattgagc agctcgtcg					19

<210> SEQ ID NO 54
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: "n" is A, T, G, or C

<400> SEQUENCE: 54
gatctnnnnn nnnnaacat					19

<210> SEQ ID NO 55
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: "n" is A, T, G, or C

<400> SEQUENCE: 55
ctcgannnnn nnnnaacac					19

<210> SEQ ID NO 56
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: "n" is A, T, G, or C

<400> SEQUENCE: 56
gagctnnnnn nnnnaacgc					19

<210> SEQ ID NO 57
<211> LENGTH: 19
<212> TYPE: DNA

<210> SEQ ID NO 57
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: "n" is A, T, G, or C

<400> SEQUENCE: 57
atgttnnnnn nnnnagctc                                              19

<210> SEQ ID NO 58
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: "n" is A, T, G, or C

<400> SEQUENCE: 58
gatctnnnnn nnnnaactc                                              19

<210> SEQ ID NO 59
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: "n" is A, T, G, or C

<400> SEQUENCE: 59
atgttnnnnn nnnnagatc                                              19

<210> SEQ ID NO 60
<211> LENGTH: 24
<212> TYPE: DNA
<213> ORGANISM: Artificial Sequence
<220> FEATURE:
<223> OTHER INFORMATION: oligonucleotide encoding ERSE1 used in
      transcriptional induction of GRP78

<400> SEQUENCE: 60
ttcaccaatc ggcggcctcc acga                                        24

<210> SEQ ID NO 61
<211> LENGTH: 28
<212> TYPE: DNA
<213> ORGANISM: Artificial Sequence
<220> FEATURE:
<223> OTHER INFORMATION: oligonucleotide encoding ERSE1 used in
      transcriptional induction of GRP94

<400> SEQUENCE: 61
cccaccaatc gcgccgcacc acgcacca                                    28

<210> SEQ ID NO 62
<211> LENGTH: 30
<212> TYPE: DNA
<213> ORGANISM: Artificial Sequence
<220> FEATURE:
<223> OTHER INFORMATION: oligonucleotide encoding ERSE3 used in
      transcriptional induction of GRP94

<400> SEQUENCE: 62
ccctgaccaa tcggaaggag ccacgcttcg                                  30

<210> SEQ ID NO 63

<211> LENGTH: 28
<212> TYPE: DNA
<213> ORGANISM: Artificial Sequence
<220> FEATURE:
<223> OTHER INFORMATION: oligonucleotide encoding ERSE3 used in
      transcriptional induction of CRT

<400> SEQUENCE: 63
ccgaccaatg atggtcgacc acgcgtgg                                          28

<210> SEQ ID NO 64
<211> LENGTH: 24
<212> TYPE: DNA
<213> ORGANISM: Artificial Sequence
<220> FEATURE:
<223> OTHER INFORMATION: ERSE1 from human GRP78 promoter where each
      nucleotide was substituted by transversion, forming a group of
      mutants.
<221> NAME/KEY: misc_feature
<222> LOCATION: (1)..(2)
<223> OTHER INFORMATION: "n" is t or g
<221> NAME/KEY: misc_feature
<222> LOCATION: (3)..(3)
<223> OTHER INFORMATION: "n" is c or a
<221> NAME/KEY: misc_feature
<222> LOCATION: (6)..(6)
<223> OTHER INFORMATION: "n" is c or a
<221> NAME/KEY: misc_feature
<222> LOCATION: (4)..(5)
<223> OTHER INFORMATION: "n" is c or a
<221> NAME/KEY: misc_feature
<222> LOCATION: (8)..(8)
<223> OTHER INFORMATION: "n" is c or a
<221> NAME/KEY: misc_feature
<222> LOCATION: (9)..(9)
<223> OTHER INFORMATION: "n" is c or t
<221> NAME/KEY: misc_feature
<222> LOCATION: (10)..(10)
<223> OTHER INFORMATION: "n" is c or g
<221> NAME/KEY: misc_feature
<222> LOCATION: (11)..(11)
<223> OTHER INFORMATION: "n" is a or g
<221> NAME/KEY: misc_feature
<222> LOCATION: (12)..(12)
<223> OTHER INFORMATION: "n" is t or g
<221> NAME/KEY: misc_feature
<222> LOCATION: (13)..(13)
<223> OTHER INFORMATION: "n" is t or c
<221> NAME/KEY: misc_feature
<222> LOCATION: (14)..(14)
<223> OTHER INFORMATION: "n" is g or a
<221> NAME/KEY: misc_feature
<222> LOCATION: (15)..(15)
<223> OTHER INFORMATION: "n" is g or t
<221> NAME/KEY: misc_feature
<222> LOCATION: (16)..(16)
<223> OTHER INFORMATION: "n" is c or t
<221> NAME/KEY: misc_feature
<222> LOCATION: (17)..(17)
<223> OTHER INFORMATION: "n" is c or a
<221> NAME/KEY: misc_feature
<222> LOCATION: (18)..(18)
<223> OTHER INFORMATION: "n" is t or a
<221> NAME/KEY: misc_feature
<222> LOCATION: (19)..(19)
<223> OTHER INFORMATION: "n" is g or c
<221> NAME/KEY: misc_feature
<222> LOCATION: (23)..(23)
<223> OTHER INFORMATION: "n" is g or a
<221> NAME/KEY: misc_feature
<222> LOCATION: (24)..(24)
<223> OTHER INFORMATION: "n" is t or a
<221> NAME/KEY: misc_feature
<222> LOCATION: (20)..(20)
<223> OTHER INFORMATION: "n" is a or c

<400> SEQUENCE: 64
nnnnnnannn nnnnnnnnnn acnn          24

<210> SEQ ID NO 65
<211> LENGTH: 24
<212> TYPE: DNA
<213> ORGANISM: Homo sapiens
<220> FEATURE:
<221> NAME/KEY: misc_feature
<222> LOCATION: (24)..(24)
<223> OTHER INFORMATION: "n" is a or c
<221> NAME/KEY: misc_feature
<222> LOCATION: (23)..(23)
<223> OTHER INFORMATION: "n" is t or g
<221> NAME/KEY: misc_feature
<222> LOCATION: (22)..(22)
<223> OTHER INFORMATION: "n" is a or c
<221> NAME/KEY: misc_feature
<222> LOCATION: (21)..(21)
<223> OTHER INFORMATION: "n" is a or c
<221> NAME/KEY: misc_feature
<222> LOCATION: (20)..(20)
<223> OTHER INFORMATION: "n" is a or c
<221> NAME/KEY: misc_feature
<222> LOCATION: (19)..(19)
<223> OTHER INFORMATION: "n" is a, t, c or g
<221> NAME/KEY: misc_feature
<222> LOCATION: (18)..(18)
<223> OTHER INFORMATION: "n" is t or g

<400> SEQUENCE: 65
ttcaccaatc ggcggccnnn nnnn          24

<210> SEQ ID NO 66
<211> LENGTH: 28
<212> TYPE: DNA
<213> ORGANISM: Homo sapiens
<220> FEATURE:
<221> NAME/KEY: misc_feature
<222> LOCATION: (24)..(24)
<223> OTHER INFORMATION: "n" is a or c
<221> NAME/KEY: misc_feature
<222> LOCATION: (23)..(23)
<223> OTHER INFORMATION: "n" is t or g
<221> NAME/KEY: misc_feature
<222> LOCATION: (22)..(22)
<223> OTHER INFORMATION: "n" is a or c
<221> NAME/KEY: misc_feature
<222> LOCATION: (21)..(21)
<223> OTHER INFORMATION: "n" is a or c
<221> NAME/KEY: misc_feature
<222> LOCATION: (20)..(20)
<223> OTHER INFORMATION: "n" is a or c
<221> NAME/KEY: misc_feature
<222> LOCATION: (19)..(19)
<223> OTHER INFORMATION: "n" is a, t, c, or g
<221> NAME/KEY: misc_feature
<222> LOCATION: (18)..(18)
<223> OTHER INFORMATION: "n" is t or g

<400> SEQUENCE: 66
ttcaccaatc ggcggccnnn nnnncggg          28

<210> SEQ ID NO 67
<211> LENGTH: 29
<212> TYPE: DNA
<213> ORGANISM: Homo sapiens

<400> SEQUENCE: 67
ttcaccaatc ggcgagcctc cacgacggg          29

<210> SEQ ID NO 68

```
<211> LENGTH: 30
<212> TYPE: DNA
<213> ORGANISM: Homo sapiens

<400> SEQUENCE: 68
ttcaccaatc ggcgaagcct ccacgacggg                                          30

<210> SEQ ID NO 69
<211> LENGTH: 31
<212> TYPE: DNA
<213> ORGANISM: Homo sapiens

<400> SEQUENCE: 69
ttcaccaatc ggcgaaagcc tccacgacgg g                                        31

<210> SEQ ID NO 70
<211> LENGTH: 29
<212> TYPE: DNA
<213> ORGANISM: Homo sapiens

<400> SEQUENCE: 70
ccttcaccaa tcggcggcct ccacgacgg                                           29

<210> SEQ ID NO 71
<211> LENGTH: 23
<212> TYPE: PRT
<213> ORGANISM: Homo sapiens

<400> SEQUENCE: 71

Arg Arg Gln Gln Arg Met Ile Lys Asn Arg Glu Ser Ala Cys Gln Ser
1               5                  10                  15

Arg Lys Lys Lys Lys Glu Tyr
            20

<210> SEQ ID NO 72
<211> LENGTH: 23
<212> TYPE: PRT
<213> ORGANISM: Yeast Hac1p

<400> SEQUENCE: 72

Arg Arg Ile Glu Arg Ile Leu Arg Asn Arg Arg Ala Ala His Gln Ser
1               5                  10                  15

Arg Glu Lys Lys Arg Leu His
            20

<210> SEQ ID NO 73
<211> LENGTH: 23
<212> TYPE: PRT
<213> ORGANISM: Homo sapiens

<400> SEQUENCE: 73

Lys Arg Gln Gln Arg Met Ile Lys Asn Arg Glu Ser Ala Cys Gln Ser
1               5                  10                  15

Arg Arg Lys Lys Lys Glu Tyr
            20

<210> SEQ ID NO 74
<211> LENGTH: 23
<212> TYPE: PRT
<213> ORGANISM: Homo sapiens

<400> SEQUENCE: 74

Lys Arg Glu Val Arg Leu Met Lys Asn Arg Glu Ala Ala Arg Glu Cys
```

```
                    1               5               10              15
Arg Arg Lys Lys Lys Glu Tyr
            20

<210> SEQ ID NO 75
<211> LENGTH: 23
<212> TYPE: PRT
<213> ORGANISM: Homo sapiens

<400> SEQUENCE: 75

Lys Arg Glu Ile Arg Leu Met Lys Asn Arg Glu Ala Ala Arg Glu Cys
1               5                   10                  15
Arg Arg Lys Lys Lys Glu Tyr
            20

<210> SEQ ID NO 76
<211> LENGTH: 23
<212> TYPE: PRT
<213> ORGANISM: Homo sapiens

<400> SEQUENCE: 76

Lys Arg Arg Lys Phe Leu Glu Arg Asn Arg Ala Ala Ala Ser Arg Cys
1               5                   10                  15
Arg Gln Lys Arg Lys Val Trp
            20

<210> SEQ ID NO 77
<211> LENGTH: 23
<212> TYPE: PRT
<213> ORGANISM: Homo sapiens

<400> SEQUENCE: 77

Arg Lys Lys Arg Arg Glu Arg Asn Lys Ile Ala Ala Ala Lys Cys
1               5                   10                  15
Arg Asn Lys Lys Lys Glu Lys
            20

<210> SEQ ID NO 78
<211> LENGTH: 23
<212> TYPE: PRT
<213> ORGANISM: Homo sapiens

<400> SEQUENCE: 78

Lys Lys Leu Lys Lys Met Glu Gln Asn Lys Thr Ala Ala Thr Arg Tyr
1               5                   10                  15
Arg Gln Lys Lys Arg Ala Glu
            20

<210> SEQ ID NO 79
<211> LENGTH: 23
<212> TYPE: PRT
<213> ORGANISM: Homo sapiens

<400> SEQUENCE: 79

Glu Lys Glu Asn Pro Lys Glu Arg Asn Lys Met Ala Ala Ala Lys Cys
1               5                   10                  15
Arg Asn Arg Arg Arg Glu Leu
            20

<210> SEQ ID NO 80
<211> LENGTH: 23
<212> TYPE: PRT
```

```
<213> ORGANISM: Homo sapiens

<400> SEQUENCE: 80

Gln Arg Gln Lys Arg Met Ile Lys Asn Arg Glu Ser Ala Ala Arg Ser
1               5                   10                  15

Arg Glu Arg Lys Gln Ala Tyr
            20

<210> SEQ ID NO 81
<211> LENGTH: 23
<212> TYPE: PRT
<213> ORGANISM: Artificial Sequence
<220> FEATURE:
<223> OTHER INFORMATION: Sequence from bZIP protein

<400> SEQUENCE: 81

Arg Arg Gln Arg Arg Met Ile Lys Asn Arg Glu Ser Ala Ala Arg Ser
1               5                   10                  15

Arg Ala Arg Lys Gln Ala Tyr
            20

<210> SEQ ID NO 82
<211> LENGTH: 23
<212> TYPE: PRT
<213> ORGANISM: Artificial Sequence
<220> FEATURE:
<223> OTHER INFORMATION: Sequence from bZIP protein

<400> SEQUENCE: 82

Arg Arg Gln Lys Arg Met Ile Lys Asn Arg Glu Ser Ala Ala Arg Ser
1               5                   10                  15

Arg Ala Arg Lys Gln Ala Tyr
            20

<210> SEQ ID NO 83
<211> LENGTH: 23
<212> TYPE: PRT
<213> ORGANISM: Artificial Sequence
<220> FEATURE:
<223> OTHER INFORMATION: Sequence from bZIP protein

<400> SEQUENCE: 83

Arg Arg Gln Arg Arg Met Ile Lys Asn Arg Glu Ser Ala Ala Arg Ser
1               5                   10                  15

Arg Ala Arg Lys Gln Ala Tyr
            20
```

ISOLATED NUCLEIC ACIDS ENCODING ACTIVATED AND SUPPRESSIVE FORMS OF ATF6

This application is the national phase under 35 U.S.C. §371 of PCT International Application No. PCT/JP99/06305 which has an International filing date of Nov. 12, 1999, which designated the United States of America and was published in English.

TECHNICAL FIELD

The present invention relates to a factor capable of efficiently regulating expression of an endoplasmic reticulum chaperone gene, a nucleic acid encoding it or a complementary strand nucleic acid thereof, a method for regulating expression of an endoplasmic reticulum chaperone gene, and a method for expressing a foreign gene.

BACKGROUND ART

Mammalian cells, like other eukaryotic cells and prokaryotic cells, have developed a number of homeostatic mechanisms to cope with to various physiological and environmental conditions that threaten their survival. Among them, the tightly regulated synthesis of heat shock proteins (HSPs) is a well-known mechanism universally found in all organisms. In addition, the regulated synthesis of glucose-regulated proteins (GRPs), based on a mechanism differing from that of HSP described above, is specifically found in eukaryotic endoplasmic reticulum [Lee, A. S., Curr. Opin. Cell Biol. 4, 267–273 (1992); Morimoto, R. I. et al., The Biology of HEAT SHOCK PROTEINS and MOLECULAR CHAPERONES, Cold Spring Harbor Laboratory (1994)].

In mammals, eight kinds of GRPs, namely, GRP78/Bip, GRP94/ERp99, ORP150/GRP170, ERp72, GRP58/ERp60/ERp61, calreticulin, protein disulfide isomerase (PDI) and FKBP13, have been identified. These GRPs are a series of molecular chaperones or folding enzymes characteristic of the endoplasmic reticulum, each of which expression is induced by the accumulation of proteins that have failed to be folded or have undergone incorrect folding (hereinafter referred to as unfolded proteins) in the endoplasmic reticulum (endoplasmic reticulum stress) [Kozutsumi, Y. et al., Nature 332, 462–464 (1988); Lee, A. S., Trends Biochem. Sci. 12, 20–23 (1987)], and play a very important role in the folding of nascent secretory proteins and membrane proteins in the endoplasmic reticulum. Therefore, these GRPs are hereinafter generically referred to as "endoplasmic reticulum chaperones".

Expression of endoplasmic reticulum chaperones is also induced by a reagent, such as tunicamycin, which inhibits N-glycosylation of proteins, calcium ionophore A23187, which depletes calcium storage, or thapsigargin, which inhibits calcium-ATPase. These reagents are generally assumed to cause malfunctioning of the endoplasmic reticulum and elicit endoplasmic reticulum stress.

Induction of the above endoplasmic reticulum chaperone by endoplasmic reticulum stress is primarily regulated at the transcription level. Since the endoplasmic reticulum chaperone is not induced by heat shock stress and the promoter sequence of the endoplasmic reticulum chaperone gene contains no heat shock elements, the induction of endoplasmic reticulum chaperone is suggested based on a regulatory mechanism differing from that for the HSP induction. There has yet remain unknown, however, whether an endoplasmic reticulum stress-response is controlled by a common mechanism or by a variety of mechanisms corresponding to individual endoplasmic reticulum chaperones.

The rat GRP78 gene has already been analyzed to some extent, and it is shown that the upstream CORE region and the C1 region comprising the CCAAT sequence are important for transcriptional regulation [Resendez, E. et al., Mol. Cell. Biol. 8, 4579–4584 (1988); Wooden, S. K. et al., Mol. Cell. Biol. 11, 5612–5623 (1991); Li, W. W. et al., Mol. Cell. Biol. 14, 5533–5546 (1994)] (see FIG. 1); however, its transcriptionally regulatory sequence yet remains undetermined. In the case of yeasts, the transcriptionally regulatory sequence (UPRE sequence; CAGNGTG) of the GRP78 gene of the budding yeast is clarified [Mori, K. et al., Genes Cells 1, 803–817 (1996)]. Although a sequence similar to the UPRE sequence is present upstream of the human GRP78 gene, no activity for directing induced transcription by endoplasmic reticulum stress has been detected in any DNA having a sequence similar to that of the UPRE. As mentioned above, the transcriptionally regulatory region involved in an endoplasmic reticulum stress-response of mammals, especially humans, still remains undetermined.

In cancer cells, endoplasmic reticulum chaperones are expressed at high levels. For example, there has been reported that good correlation exists between intracellular GRP78 level and a tumor size [Cai, J. W. et al., J. Cell. Physiol. 154, 229–237 (1993)], and that when GRP78 expression is suppressed by the antisense method, sensitivity to cytotoxic T-cell (CTL) and tumor necrosis factor (TNF) increases [Sugawara, S. et al., Cancer Res. 53, 6001–6005 (1993)] and take is poor in the mouse, and even if taking, it soon results in regression [Jamora, C. et al., Proc. Natl. Acad. Sci. USA 93, 7690–7694 (1996)].

Also, it has been shown that ORP150 is strongly induced in macrophages which infiltrate into arteriosclerotic lesions, and that macrophages treated with an antisense oligonucleotide to suppress ORP150 expression show decreased viability when exposed to hypoxic conditions, especially in the presence of a denatured LDL (low-density lipoprotein) [Tsukamoto, Y. et al., J. Clin. Invest. 98, 1930–1941 (1996)]. Since the macrophages in arteriosclerotic lesions release cytokines, such as tumor necrosis factor, interleukin-1 (IL-1), interleukin-6 (IL-6), fibroblast growth factor (FGF), platelet-derived growth factor (PDGF) and transforming growth factor (TGF-β), the macrophages are positioned at the center of intercellular response in arteriosclerotic lesions and assumed to play a major role in the progression of arteriosclerosis.

Cystic fibrosis is a hereditary disease caused by a mutation of the cystic fibrosis transmembrane conductance regulator (CFTR) gene, the most prevalent of such a mutation being the deletion of phenylalanine at residue 508 (α508F) [Welsh, M. J. and Smith, A. E., Cell 73, 1251–1254 (1993)]. CFTRΔ508F undergoes abnormal sugar chain addition and is degraded without being transported from the endoplasmic reticulum to the Golgi. However, at low temperatures, such Δ508F mutants leak from endoplasmic reticulum, are localized in the cell membrane, thereby exhibiting activity [Denning, G. M. et al., Nature 358, 761–764 (1992)]. Appropriately modifying the stringency of quality control for nascent membrane proteins in the endoplasmic reticulum would enable the localization and functioning of CTFRΔ508F in the cell membrane.

Furthermore, there have been shown that the mRNA of GRP78, as well as of HSP70, is induced in rat cerebral ischemia [Wang, S. et al., Neurochem. Int. 23, 575–582 (1993); Higashi, T. et al., Brain Res. 650, 239–248 (1994)], that the mRNA of GRP78 and GRP94 is induced in the hippocampal dentate gyrus when convulsive seizures are induced with kainic acid [Lowenstein, D. H. et al., Mol.

*Brain Res.* 22, 299–308 (1994); Little, E. et al., *Neuroscience* 75, 209–219 (1996)], and that ORP150 is induced in the ischemic mouse brain [Kuwabara, K. et al., *J. Biol. Chem.* 271, 5025–5032 (1996)]. Therefore, the endoplasmic reticulum chaperones are assumed to protectively act on damaged neurocytes by cerebral ischemia or the like.

In addition, in wounded tissues and ulcerative tissues, endoplasmic reticulum chaperones, like HSP, are expected to play an important role in repairing the damaged tissues.

On the other hand, when a foreign gene is introduced into a desired cell, to produce a useful protein, the expression of the introduced gene must be controlled, if the desired gene product exhibits cytotoxicity or affects cell function. In addition, when a foreign, useful protein is expressed in a host using a recombinant DNA, the desired protein in many cases fails to retain the correct conformation so that the protein cannot be expressed at high levels. It is suggested that the amount of the endoplasmic reticulum chaperones and folding enzymes in usual hosts may be insufficient to ensure ample protein expression and formation of correct conformation.

Therefore, there is a demand for a technique for enabling efficient control of the expression of the endoplasmic reticulum chaperones.

DISCLOSURE OF INVENTION

An object of the present invention is to provide a method for regulating expression of endoplasmic reticulum chaperone genes, which is capable of increasing or decreasing expression of the above gene; a method for expressing a foreign protein; an endoplasmic reticulum stress transcription factor capable of regulating expression of the above gene; and a nucleic acid encoding it, or a complementary nucleic acid thereof.

The above object and other objects of the present invention will be apparent from the following description.

Concretely, the present invention is concerned with the following:

[1] an endoplasmic reticulum stress transcription factor capable of regulating transcription-inducing activity, wherein the transcription-inducing activity is exhibited by an element having the nucleotide sequence as shown in SEQ ID NO: 1 or an element having a nucleotide sequence having substitution of 1 to 3 bases with other kind of bases in the nucleotide sequence as shown in SEQ ID NO: 1;

[2] a method for controlling expression of an endoplasmic reticulum chaperone, comprising expressing the endoplasmic reticulum stress transcription factor as defined above in item [1];

[3] a method for expressing a foreign protein, comprising positively regulating expression of an endoplasmic reticulum chaperone gene by the method as defined in item [2];

[4] a nucleic acid encoding an activated form of ATF6, or a complementary strand thereto;

[5] a nucleic acid encoding an activated form of CREB-RP, or a complementary strand thereto;

[6] a nucleic acid encoding a suppressive form of ATF6, or a complementary strand thereto; and

[7] a nucleic acid encoding a suppressive form of CREB-RP, or a complementary strand thereto.

BRIEF DESCRIPTION OF THE DRAWINGS

FIG. 2 shows a tandem repeat structure of the region [−139 to −42] in the human GRP78 promoter (SEQ ID NOS:38–40). Three repetitive sequences in the above region are aligned, and the nucleotides conserved among at least two repeat sequences are shaded. The ERSE consensus is shown at the top.

FIG. 3 shows an ERSE-like sequence (SEQ ID NOs: 5 to 30) of known mammalian and chicken GRP promoters. The nucleotides congruent with the consensus are shaded. In the figure, CRT indicates calreticulin.

FIG. 5 shows ERSE-like motifs (SEQ ID NOS:41–53) in vertebrates, plants and fungi. In the figure, CRT indicates calreticulin; PDI, protein disulfide isomerase; Dm, *Drosophila melanogaster*; Ce, *Caenorhabditis elegans*; At, *Arabidopsis thaliana*; So, *Spinacia oreracea*; Rc, *Ricinus communis*; and An, *Aspergillus nigar*.

FIG. 6 shows effects of disrupting ERSEs. Panel (A) show effects of disrupting ERSEs on human GRP78 promoter activities; panel (B) shows effects of disrupting ERSEs on GRP94 promoter activities; and panel (C) shows effects of disrupting ERSEs on calreticulin promoter activities. Each of ERSE1, ERSE2 and ERSE3 of GRP78 promoter, ERSE1 and ERSE3 of GRP94 promoter, and ERSE2 and ERSE3 of calreticulin promoter was disrupted by mutating the respective sequences to gatcT(N9)aacat (SEQ ID NO:54), Ctcga (N9)aacac (SEQ ID NO:55), gagcT(N9)aacgc (SEQ ID NO:56), atgtt(N9)Agctc (SEQ ID NO:57), gatcT(N9)aactc (SEQ ID NO:58) and atgtt(N9)Agatc (SEQ ID NO:59), respectively. The intact or resultant mutant promoters were inserted into the KpnI-XhoI sites of the pGL3-Basic vector. Left panel shows a schematic view of intact or mutant ERSE-disruption constructs. Numbers on arrows indicate a nucleotide position from the transcription initiation site. Closed and hatched boxes indicate the locations of an intact ERSE motif and an ERSE motif with remarkable homology to the consensus, respectively. Crosses indicate disrupted ERSEs. Middle panel shows relative firefly luciferase activities by transection into cells. Closed bars and open bars, respectively, indicate HeLa cells transiently transfected with each construct treated with or without 2 μg/ml tunicamycin (in the figure, referred to as "TM") for 16 hours. Right panel shows fold induction of induced activities to basal levels of a reporter activity. The relative luciferase activity and the fold induction were determined from four independent, transient expression assays.

FIG. 13 shows comparison of a basic region of human ATF6 (SEQ ID NO:71). Panel (A) shows comparison with yeast Hac1p (SEQ ID NO:72); Panel (B) shows comparison with members of human ATF/CREB (SEQ ID NOs:73–79) family; and Panel (C) shows comparison with bZIP (SEQ ID NOS: 80–83) proteins.

FIG. 26 shows comparison of mobility on SDS-PAGE for each of various C-terminal deletion mutants with that of p90ATF6 or p50ATF6. HeLa cells in a 60-mm dish were transiently transfected with pCGN vector alone (Vec), expression plasmids for C-terminal deletion mutants pCGN-ATF6(670), pCGN-ATF6(402), pCGN-ATF6(373), pCGN-ATF6(366), or pCGN-ATF6(330). Whole proteins were directly extracted with 1×Laemmli's SDS sample buffer, and the extract was subjected to SDS-PAGE (10% gel) and analyzed by immunoblotting with an anti-ATF6 antibody. The positions of p90ATF6 and p50ATF6 are indicated by open and closed arrows, respectively.

FIG. 29 shows the results of immunoblot analysis for CREB-RP. In the same manner as the method described in FIG. 20, the analysis was carried out by applying a cell extract to SDS-PAGE, and then immunoblotting the resulting gel using an anti-CREB-RP antibody or an anti-ATF6 antibody or an anti-KDEL antibody.

BEST MODE FOR CARRYING OUT THE INVENTION

Figure 1:
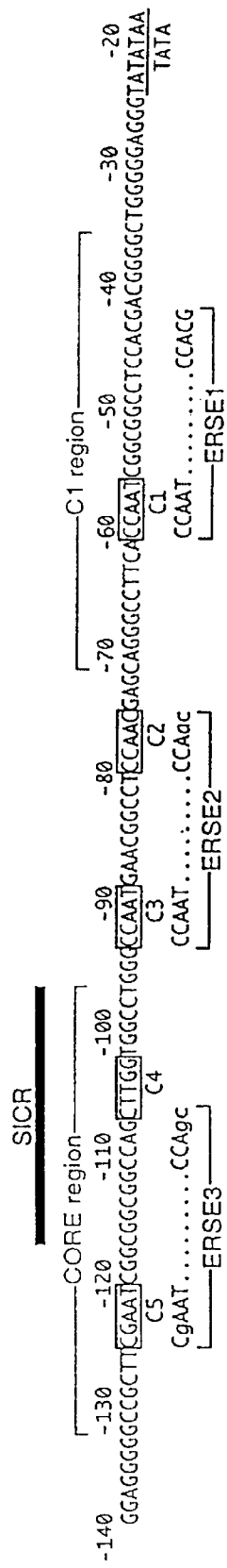
FIG. 1 shows a nucleotide sequence of the proximal region of human GRP78 promoter (SEQ ID NO: 37)[−140 to −19]. The CCAAT-like motifs designated C1 to C5 and TATA sequence are boxed and underlined, respectively. Locations of the CORE and C1 regions, and SICR and CCAAT(N9)CCACG motifs are also indicated.

In the present specification, the term "endoplasmic reticulum chaperone" refers to a series of proteins characteristic of endoplasmic reticulum, wherein expression of the above proteins is induced by endoplasmic reticulum stress, and the above proteins are a protein or enzyme having an activity for promoting or catalyzing folding or formation of conformation of secretory proteins and membrane proteins. The endoplasmic reticulum chaperone includes, for example, GRP78, GRP94, ORP150, ERp72, GRP58, calreticulin, PDI, FKBP13, and the like. The endoplasmic reticulum chaperone also encompasses proteins derived from animals such as mammals, and proteins derived from plants.

In addition, a gene encoding the above endoplasmic reticulum chaperone refers to herein as "endoplasmic reticulum chaperone gene."

(1) Endoplasmic Reticulum Stress Transcription Factor Capable of Regulating Expression of Endoplasmic Reticulum Chaperone Gene and Nucleic Acid Encoding It The phrase "endoplasmic reticulum stress transcription factor capable of regulating expression of endoplasmic reticulum chaperone genes" refers to a factor capable of regulating expression by interaction with an endoplasmic reticulum stress-response element (hereinafter simply referred to as "ERSE") which is present on the above endoplasmic reticulum chaperone gene. Therefore, the endoplasmic reticulum stress transcription factor of the present invention can exhibit an excellent effect for regulating expression of the above endoplasmic reticulum chaperone genes at once.

Here, the term "ERSE" refers to an element having activity for directing induced transcription by endoplasmic reticulum stress, wherein the element is an element having a nucleotide sequence as shown in SEQ ID NO: 1 or an element having a nucleotide sequence having substitution of 1 to 3 bases with other kind of bases in the nucleotide sequence as shown in SEQ ID NO: 1.

Concretely, the above endoplasmic reticulum stress transcription factor includes an endoplasmic reticulum stress transcription factor capable of regulating transcription-inducing activity, wherein the transcription-inducing activity is exhibited by an element having the nucleotide sequence as shown in SEQ ID NO: 1, or an element having a nucleotide sequence having substitution of 1 to 3 bases with other kind of bases in the nucleotide sequence as shown in SEQ ID NO: 1.

The phrase "nucleotide sequence having substitution of 1 to 3 bases with other kind of bases" means a naturally occurring nucleotide sequence having substitution of 1 to 3 bases with other kind of bases and a nucleotide sequence resulting from artificial substitution of 1 to 3 bases with other kind of bases.

The endoplasmic reticulum stress transcription factor includes, for example, bZIP transcription factor, concretely ATF6 [Hai, T. W. et al., *Genes Dev.* 3, 2083–2090 (1989)], CREB-RP [Min, J. et al., *Genomics* 30, 149–156 (1995)], XBP-1/TREB5 [Liou, H. C. et al., *Science* 247, 1581–1584 (1990), Yoshimura, T. et al., *EMBO J.* 9, 2537–2542 (1990)], and the like.

The nucleotide sequence and the amino acid sequence of the above ATF6 are shown in SEQ ID NOs: 31 and 32, respectively. In addition, the nucleotide sequence and the amino acid sequence of the above CREB-RP are shown in SEQ ID NOs: 33 and 34, respectively.

The endoplasmic reticulum stress transcription factor encompasses a factor capable of regulating transcription-inducing activity which is exhibited by the above endoplasmic reticulum stress-response element, wherein the factor comprises a polypeptide which can be encoded by a nucleic acid selected from the group consisting of:

(A) a nucleic acid having the nucleotide sequence as shown in SEQ ID NO: 31;

(B) a nucleic acid having the nucleotide sequence as shown in SEQ ID NO: 33;

(C) a nucleic acid having a nucleotide sequence having substitution, deletion, addition or insertion of one or more bases in the nucleotide sequence of the nucleic acid (A) or (B); and (D) a nucleic acid capable of hybridizing under stringent conditions to the strand complementary to any one of nucleic acids (A) to (C).

In the present specification, the phrase "having substitution, deletion, addition or insertion of one or more bases" refers to a state in which one or more bases are naturally or artificially substituted, deleted, added or inserted. In addition, "one or more bases" can be selected in a range capable of regulating transcription-inducing activity exhibited by an endoplasmic reticulum stress-response element.

Further, the term "nucleic acid" refers, for example, to a DNA, and an RNA corresponding thereto.

The term "stringent conditions" includes hybridizing at 68° C. with 6×SSC in aqueous or at 42° C. in 50% formamide with 6×SSC. Prehybridization is carried out with a solution of 6×SSC (or 6×SSPE), 5×Denhardt's reagent, 0.5% SDS and 100 μg/ml denatured, fragmented salmon sperm DNA in aqueous or in 50% formamide or a solution of 6×SSC (or 6×SSPE) and 0.05×BLOTTO in aqueous or in 50% formamide. This standard protocol is further described in Molecular Cloning: A Laboratory Manual, Second Edition (Sambrook, J. et al. 1989) and is hereby incorporated by reference.

The endoplasmic reticulum stress transcription factor further encompasses, as long as the factor is capable of regulating transcription-inducing activity exhibited by an endoplasmic reticulum stress-response element, a polypeptide comprising an amino acid sequence having substitution, deletion, addition, or insertion of one or more amino acids in the amino acid sequence as shown in each of SEQ ID NOs: 32 and 34.

In the present specification, "having substitution, deletion, addition, or insertion of one or more amino acids" refers to a state in which one or more amino acids are naturally or artificially substituted, deleted, added or inserted. In addition, "one or more amino acids" can be selected in a range capable of regulating transcription-inducing activity exhibited by an endoplasmic reticulum stress-response element.

In addition, the present invention encompasses an endoplasmic reticulum stress transcription factor which can be obtained as follows.

A method for obtaining an endoplasmic reticulum stress transcription factor capable of enhancing expression of endoplasmic reticulum chaperone genes (hereinafter referred to as "activated form of an endoplasmic reticulum stress transcription factor") includes, but not particularly limited to, a method comprising comparing an expression level of a reporter gene which is incorporated downstream of ERSE described as follows in the absence or presence of endoplasmic reticulum stress by a one-hybrid method using ERSE and a yeast host, whereby obtaining the factor using an increase of the expression level as an index.

On the other hand, an endoplasmic reticulum stress transcription factor for decreasing expression of endoplasmic reticulum chaperone genes (hereinafter referred to as "suppressive form of an endoplasmic reticulum stress transcription factor") can be obtained by comparing an expression level of a reporter gene which is incorporated downstream of ERSE in the absence or presence of endoplasmic reticulum stress, whereby obtaining the factor using a decrease in the expression level as an index in the same manner as the above.

The activated form of an endoplasmic reticulum stress transcription factor includes, for example, ATF6, and the like.

It is suggested in the following examples of the present specification that the above ATF6 is a membrane protein of the endoplasmic reticulum, and the ATF6 is a bZIP transcription factor having a characteristic of increasing expression of an endoplasmic reticulum chaperone. Transcription-increasing activity of endoplasmic reticulum chaperone genes in which ERSE having intact CCAAT and CCACG region of the nucleotide sequence as shown in SEQ ID NO: 1 is present can be demonstrated by the presence of the above ATF6.

Although the ATF6 is usually a protein having a molecular weight of about 90 kDa (hereinafter referred to as "p90ATF6"), the p90ATF6 is converted into a 50 kDa activated form of protein (hereinafter referred to as p50ATF6) in the presence of endoplasmic reticulum stress. It is strongly suggested in the following examples of the present specification that the above p50ATF6 is a portion for N-terminal region of p90ATF6, and is localized in the nucleus. p50ATF6 is preferable because the p50ATF6 enhances an activity for increasing expression of endoplasmic reticulum chaperone genes.

The term "endoplasmic reticulum stress" refers to phenomena of accumulation of unfolded proteins in the endoplasmic reticulum under various conditions preventing correct folding of proteins. Concretely, the endoplasmic reticulum stress can be caused by a treatment with, for instance, glucose depletion, tunicamycin [Kozutsumi, Y. et al., Nature 332, 462–464 (1988)], calcium ionophore A23187 [Watowich, S. K., Mol. Cell. Biol. 11, 5612–5623 (191)], thapsigargin [Li, W. W., J. Biol. Chem. 268, 12003–12009 (1993)], 2-deoxyglucose, hypoxia and the like.

Conditions for obtaining p50ATF6 by the above endoplasmic reticulum stress are not particularly limited. For example, when tunicamycin is used, p90ATF6 can be converted into p50ATF6 by treating cells with 0.5 to 8 μg/ml tunicamycin for 2 to 8 hours to induce endoplasmic reticulum stress.

In addition, the activated form of ATF6 includes a polypeptide comprising an N-terminal region (an entire or partial portion of a region of 1st to 373rd amino acids or a region of 1st to 366th amino acids). From the viewpoint of sufficiently exhibiting activity for increasing expression of endoplasmic reticulum chaperone genes, the activated form of ATF6 includes a polypeptide comprising preferably a region of 1st to 43rd amino acids, more preferably a region of 1st to 150th amino acids. Such an activated form of ATF6 can be prepared, for instance, by introducing stop codon at the position of termination for a desired amino acid region.

Alternatively, examples of the suppressive form of an endoplasmic reticulum stress transcription factor include suppressive form of ATF6, CREB-RP, and the like. Those factors have a property for decreasing expression of endoplasmic reticulum chaperone genes.

The above suppressive form of ATF6 is a polypeptide resulting from disruption of an entire or partial portion of a region of 1st to 150th amino acids from ATF6 or activated form of ATF6. Such a suppressive form of ATF6 has properties of acting as dominant negative, and decreasing expression of endoplasmic reticulum chaperone genes.

Here, the term "disruption of an entire or partial portion" refers to a state in which the function possessed by the activated form of the transcription factor cannot be exhibited by mutations such as deletion, insertion, substitution, and the like.

Although the above CREB-RP is usually a 110 kDa protein (hereinafter referred to as "p110CREB-RP"), the p110CREB-RP is converted into a 60 kDa protein (hereinafter referred to as "p60CREB-RP") in the presence of endoplasmic reticulum stress, in the same manner as conversion of p90ATF6 into p50ATF6 by endoplasmic reticulum stress. Surprisingly, differing from p110CREB-RP, p60CREB-RP has an activity for increasing expression of endoplasmic reticulum chaperone genes and acts as an activated form of an endoplasmic reticulum stress transcription factor. That is, in addition to the above ATF6 (p90ATF6 and p50ATF6), the activated form of an endoplasmic reticulum stress transcription factor includes p60CREB-RP.

Furthermore, a polypeptide resulting from deletion of an entire or partial portion of a region of 1st to 307th amino acids from the above activated form of CREB-RP has properties of acting as dominant negative, and is included in the suppressive form of an endoplasmic reticulum stress transcription factor.

The presence or absence of expression of endoplasmic reticulum chaperone genes by the above endoplasmic reticulum stress transcription factor (for example, bZIP transcription factor, and the like) can be confirmed, for instance, by quantifying mRNA to evaluate the presence or absence of transcription. In other words, whether or not the desired gene is transcribed can be determined by extracting an RNA from cells, and subjecting the resulting RNA to Northern blot hybridization or RNA protection assay. The transcription level of the corresponding mRNA also can be relatively evaluated by introducing a plasmid resulting from incorporation of a fusion gene of the above endoplasmic reticulum chaperone gene with a reporter gene such as chloramphenicol acetyltransferase (hereinafter referred to as "CAT") gene or luciferase gene; and then measuring an activity for the reporter gene product CAT or luciferase.

The above endoplasmic reticulum stress transcription factor (for example, bZIP transcription factor, and the like) can be expressed, according to conventional methods, by using cells resulting from incorporation of a DNA comprising a gene encoding the above endoplasmic reticulum stress transcription factor into a chromosome of a host cell; or cells resulting from incorporation of the same DNA into a vector commonly used, and thereafter introducing the resulting vector into a host cell.

There may be used a gene encoding endoplasmic reticulum stress transcription factor in which suitable promoter, and the like are placed. The above promoter includes, for example, SV40 promoter, cytomegalovirus promoter, retrovirus LTR promoter, β-actin promoter, yeast ADH1 promoter, yeast GAP-DH promoter, and the like.

When the above gene is incorporated into a vector, the above vector commonly used includes plasmids, cosmids, viruses, and the like. Concretely, the vector includes, but not limited to, pKCR, pcDL-SRα, pCAGGS, retrovirus vector, adenovirus vector, adeno-associated virus vector, vectors for yeast: YIp, YCp, YEp, YRp derivative plasmids, and the like.

The above host, but not limited to, includes for example, HeLa cells, CHO cells, FM3A cells, L cells, BALB/c3T3 cells, BHK cells, ES cells, yeast Saccharomyces cervisae, and the like.

A method for introducing a DNA carrying a gene encoding the above endoplasmic reticulum stress transcription factor into a host cell includes, but not limited to, conventional methods such as calcium phosphate method, electroporation method, lipofection method, and DEAE dextran method.

In the endoplasmic reticulum transcription factor of the present invention, there may be a case where the extent of exhibiting the effect of increase or decrease in expression is different depending upon the ERSE nucleotide sequence in the gene.

Examples of the ERSE include an element [CCAAT(N)$_9$CCACG] having the nucleotide sequence as shown in SEQ ID NO: 1. By analyzing the transcriptional regulatory region (SEQ ID NO: 4, FIG. 1) of a gene encoding a kind of GRP, human GRP78 protein, the above sequence was clarified for the first time that the sequence is a region involved in the transcriptional regulation by endoplasmic reticulum stress and obtained thereby.

The nucleotide sequence as shown in SEQ ID NO: 1 is a well preserved sequence in ERSE1 (SEQ ID NO: 5) of human GRP78, ERSE1 (SEQ ID NO: 6) of murine GRP78, ERSE1 (SEQ ID NO: 7) of rat GRP78, ERSE1 (SEQ ID NO: 8) of human GRP94, ERSE1 (SEQ ID NO: 9) of chicken GRP94, ERSE3 (SEQ ID NO: 10) of human GRP94, ERSE3 (SEQ ID NO: 11) of chicken GRP94, ERSE3 (SEQ ID NO: 12) of human calreticulin, ERSE3 (SEQ ID NO: 13) of murine calreticulin, and the like.

In addition, the ERSE is a nucleotide sequence having substitution of 1 to 3 bases with other kind of bases in the nucleotide sequence as shown in SEQ ID NO: 1, which may be an element capable of exhibiting transcription-inducing activity by endoplasmic reticulum stress. The above element may be a DNA resulting from substitution of 1 to 3 bases with other kind of bases in the nucleotide sequence as shown in SEQ ID NO: 1 by genetic engineering techniques, or it may be a naturally occurring DNA having a nucleotide sequence having substitution of 1 to 3 bases. Examples of the naturally occurring DNAs include ERSE2 (SEQ ID NO: 14) of human GRP78, ERSE2 (SEQ ID NO: 15) of murine GRP78, ERSE2 (SEQ ID NO: 16) of rat GRP78, ERSE3 (SEQ ID NO: 17) of human GRP78, ERSE3 (SEQ ID NO: 18) of murine GRP78, ERSE3 (SEQ ID NO: 19) of rat GRP78, ERSE2 (SEQ ID NO: 20) of human GRP94, ERSE4 (SEQ ID NO: 21) of human GRP94, ERSE2 (SEQ ID NO: 22) of chicken GRP94, ERSE1 (SEQ ID NO: 23) of human calreticulin, ERSE2 (SEQ ID NO: 24) of human calreticulin, ERSE2 (SEQ ID NO: 25) of murine calreticulin, ERSE1 (SEQ ID NO: 26) of murine ERp72, ERSE2 (SEQ ID NO: 27) of murine ERp72, ERSE1 (SEQ ID NO: 28) of human protein disulfide isomerase, ERSE2 (SEQ ID NO: 29) of human protein disulfide isomerase, ERSE2 (SEQ ID NO: 30) of human GRP58, and the like. In the ERSE, similar sequences are found in vertebrates, plants, fungi, and the like (FIG. 5).

In the ERSE, the expression can be further effectively controlled by having coexistence of three elements ERSEs 1 to 3 as shown in SEQ ID NOs: 1 to 3.

A method for obtaining the ERSE is not particularly limited thereto, and the ERSE can be obtained as described in Examples set forth below.

The nucleic acid for encoding the endoplasmic reticulum stress transcription factor has an excellent characteristic that the nucleic acid can be used in gene therapies for diseases such as ischemic diseases and cancers. For instance, there are expected that the ischemic diseases can be treated by positively controlling the expression of the endoplasmic reticulum chaperone gene (increase in expression level), and conversely the cancers can be treated by negatively controlling the expression (decrease in expression level).

When expression of the endoplasmic reticulum chaperone gene is positively controlled, as the nucleic acid encoding the endoplasmic reticulum stress transcription factor, there can be used a nucleic acid encoding an activated form of ATF6 or a nucleic acid encoding an activated form of CREB-RP.

Concrete examples of the nucleic acid encoding an activated form of ATF6 include any one of nucleic acids selected from the group consisting of:
(a) a nucleic acid having a nucleotide sequence encoding an amino acid sequence as shown in amino acid numbers: 1 to 373 in SEQ ID NO: 32;
(b) a nucleic acid having a nucleotide sequence encoding an amino acid sequence as shown in amino acid numbers: 1 to 366 in SEQ ID NO: 32;
(c) a nucleic acid having a nucleotide sequence as shown in base numbers: 69 to 1187 in SEQ ID NO: 31;
(d) a nucleic acid having a nucleotide sequence as shown in base numbers: 69 to 1166 in SEQ ID NO: 31;
(e) a nucleic acid having a nucleotide sequence having substitution, deletion, addition or insertion of at least one base in the nucleic acid of any one of (a) to (d); and
(f) a nucleic acid capable of hybridizing to a strand complementary to the nucleic acid of any one of (a) to (e) under stringent conditions, or the complementary strand thereto. In addition, concrete examples of the nucleic acid encoding an activated form of CREB-RP include any one of nucleic acids selected from the group consisting of:
(g) a nucleic acid having a nucleotide sequence encoding an amino acid sequence as shown in amino acid numbers: 1 to 389 in SEQ ID NO: 34;
(h) a nucleic acid having a nucleotide sequence as shown in base numbers: 47 to 1213 in SEQ ID NO: 33;
(i) a nucleic acid having a nucleotide sequence having substitution, deletion, addition or insertion of at least one base in the nucleic acid of any one of (g) and (h); and
(j) a nucleic acid capable of hybridizing to the strand complementary to the nucleic acid of any one of (g) to (i) under stringent conditions, or the complementary strand thereto.

When expression of the endoplasmic reticulum chaperone gene is negatively regulated (decrease in expression level), as the nucleic acid encoding the endoplasmic reticulum stress transcription factor, there can be used a strand nucleic acid complementary to the nucleic acid encoding an activated form of ATF6, a nucleic acid strand complementary to the nucleic acid encoding an activated form of CREB-RP, a nucleic acid encoding a suppressive form of ATF6, a nucleic acid encoding a suppressive form of CREB-RP, and the like.

Concretely, as the complementary strand to the nucleic acid encoding an activated form of ATF6, there can be cited complementary strand to the nucleic acids selected from the group consisting of (a) to (f) above. The complementary strand to the nucleic acid encoding an activated form of CREB-RP includes complementary strand to the nucleic acids selected from the group consisting of (g) to (j) above. As the nucleic acid encoding a suppressive form of ATF6, there can be cited nucleic acids selected from the group consisting of:
(k) a nucleic acid having a nucleotide sequence encoding an amino acid sequence as shown in amino acid numbers: 151 to 670 in SEQ ID NO: 32;
(l) a nucleic acid having a nucleotide sequence encoding an amino acid sequence as shown in amino acid numbers: 151 to 373 in SEQ ID NO: 32;
(m) a nucleic acid having a nucleotide sequence encoding an amino acid sequence as shown in amino acid numbers: 151 to 366 in SEQ ID NO: 32;
(n) a nucleic acid having a nucleotide sequence as shown in base numbers: 519 to 2078 in SEQ ID NO: 31;
(o) a nucleic acid having a nucleotide sequence as shown in base numbers: 519 to 1187 in SEQ ID NO: 31;
(p) a nucleic acid having a nucleotide sequence as shown in base numbers: 519 to 1166 in SEQ ID NO: 31;
(q) a nucleic acid having a nucleotide sequence having substitution, deletion, addition or insertion of at least one base in the nucleic acid of any one of (k) to (p); and
(r) a nucleic acid capable of hybridizing to the strand complementary to the nucleic acid of any one of (k) to (q) under stringent conditions, or the complementary strand thereto. The nucleic acid encoding a suppressive form of CREB-RP includes nucleic acids selected from the group consisting of:

(s) a nucleic acid having a nucleotide sequence encoding an amino acid sequence as shown in amino acid numbers: 308 to 386 in SEQ ID NO: 34;

(t) a nucleic acid having a nucleotide sequence as shown in base numbers: 968 to 1204 in SEQ ID NO: 33;

(u) a nucleic acid having a nucleotide sequence encoding an amino acid sequence as shown in amino acid numbers: 151 to 389 in SEQ ID NO: 34;

(v) a nucleic acid having a nucleotide sequence as shown in base numbers: 497 to 1213 in SEQ ID NO: 33;

(w) a nucleic acid having a nucleotide sequence encoding an amino acid sequence as shown in amino acid numbers: 81 to 389 in SEQ ID NO: 34;

(x) a nucleic acid having a nucleotide sequence as shown in base numbers: 287 to 1213 in SEQ ID NO: 33;

(y) a nucleic acid having a nucleotide sequence having substitution, deletion, addition or insertion of at least one base in the nucleic acid of any one of (s) to (x); and (z) a nucleic acid capable of hybridizing to the strand complementary to the nucleic acid of any one of (s) to (y) under stringent conditions, or the complementary strand thereto.

The substances having activity for suppressing expression of the endoplasmic reticulum chaperones [for instance, a suppressive form of ATF6, nucleic acids of (k) to (r), complementary strands to nucleic acids of (a) to (f), a suppressive form of CREB-RP, nucleic acids of (s) to (z), complementary strands to nucleic acids of (g) to (j), and the like] are expected to be used as a therapeutic drug or a prophylactic drug for cancers, arteriosclerosis or cystic fibrosis. In addition, the substances having activity for inducing expression of the endoplasmic reticulum chaperones [for instance, an activated form of ATF6, nucleic acids of (a) to (f), an activated form of CREB-RP, nucleic acids of (g) to (j), and the like] are expected to be used as a therapeutic drug or a prophylactic drug for ischemic diseases, wounds or ulcers.

When the substance having activity for suppressing expression of the endoplasmic reticulum chaperones or the substance having activity for inducing expression of the endoplasmic reticulum chaperones is used as a therapeutic drug or prophylactic drug, its administration form includes oral administration, inhalant administration, intravenous injection, subcutaneous injection, and the like.

From the viewpoint of easiness in the introduction of the nucleic acid or the complementary strand thereto into cells, the method for administering the nucleic acid or the complementary strand thereto of the present invention includes a method of administration of a construct resulting from incorporation of the nucleic acid or the complementary strand thereto into a virus vector by means such as oral administration, inhalant administration, intravenous injection, subcutaneous injection, and the like; a method for directly intramuscularly administering a composition comprising an expression plasmid harboring the nucleic acid or the complementary strand thereto (DNA vaccine method); liposome method; lipofection method; microinjection method; calcium phosphate method; electroporation method, and the like.

The nucleic acid or the complementary strand thereto of the present invention may be chemically modified nucleic acids, including, for instance, phosphothioates, phosphodithioates, trialkylphosphoric acid esters, alkyl phosphonates, alkylphosphoamidates, and the like.

(2) Method for Controlling Expression of Endoplasmic Reticulum Chaperone

One of the great features of a method for controlling expression of an endoplasmic reticulum chaperone resides in that the endoplasmic reticulum stress transcription factor, for instance, bZIP transcription factor, or the like) is expressed. According to the method for controlling expression of endoplasmic reticulum chaperones of the present invention, there is exhibited an excellent effect in that treatment or prophylaxis of cancers, arteriosclerosis, cystic fibrosis, ischemic diseases, wounds or ulcers is made possible by controlling expression of endoplasmic reticulum chaperone genes using the endoplasmic reticulum stress transcription factor. In addition, according to the method for controlling expression of endoplasmic reticulum chaperone genes of the present invention, there is exhibited an excellent effect in that a correct conformation can be maintained and a desired protein can be exhibited at a high level in the expression of a foreign protein by a recombinant DNA.

Since the endoplasmic reticulum stress transcription factor of the present invention can control expression of all of the endoplasmic reticulum chaperone genes at once, the method using the endoplasmic reticulum stress transcription factor of the present invention is expected to have remarkably excellent controlling effects as compared to the method of controlling expression of each of the individual endoplasmic reticulum chaperone genes.

In the present invention, expression of endoplasmic reticulum chaperone genes can be controlled by regulating an expression level of the endoplasmic reticulum stress transcription factor within the cell, or the activity for positively or negatively regulating expression of endoplasmic chaperone genes can be adjusted by selecting the endoplasmic reticulum stress transcription factor to be expressed in the cells.

When expression of the endoplasmic reticulum chaperone genes is controlled by regulating the expression level of the endoplasmic reticulum stress transcription factor, the expression level can be regulated by introducing into cells a DNA encoding the endoplasmic reticulum stress transcription factor, or a DNA encoding antisense RNA of the endoplasmic reticulum stress transcription factor, or an antisense oligonucleotide.

When expression of the endoplasmic reticulum chaperone genes is regulated positively (increase in expression level) or negatively (decrease in expression level) in accordance with the selection of the endoplasmic reticulum stress transcription factor to be expressed, the expression can be regulated by, for instance, selecting an endoplasmic reticulum stress transcription factor from a bZIP transcription factor ATF6, CREB-RP, XBP-1/TREB5, or the like in accordance with the direction (positive or negative) of the regulation of expression. Besides the above, there may be appropriately selected the endoplasmic reticulum stress transcription factors described in item (1) above (for instance, bZIP transcription factors), or other transcription factors depending upon the characteristics owned by nucleic acids.

When the expression level of the endoplasmic reticulum chaperone gene is increased, for instance, one obtained by expressing AFT6 within the cell as p90ATF6, to form p50ATF6 by endoplasmic reticulum stress may be used, or one obtained by expressing a DNA encoding p50ATF6 may be used. Further, there may be used one obtained by expressing a DNA encoding p60CREB-RP.

In addition, when the ATF6 is used, a polypeptide containing an N-terminal region (an entire or partial portion of a region of 1st to 373th amino acids, or of an entire or partial portion of a region of 1st to 366th amino acids) can be used. From the viewpoint of sufficiently exhibiting activity of increasing expression of the endoplasmic reticulum chaperone genes, there may be employed one obtained by expressing within the cells a DNA encoding a polypeptide preferably containing a region of 1st to 43rd amino acids, more preferably a region of 1st to 150th amino acids.

Further, when the activated form of CREP-RP is used, there may be employed a polypeptide containing an N-terminal region (an entire or partial portion of a region of 1st to 389th amino acids), or one obtained by expressing a DNA encoding the above polypeptide within the cell.

On the other hand, when the expression level of the endoplasmic reticulum chaperone genes is decreased, a polypeptide resulting from disruption of an entire or partial portion of a region of 1st to 150th amino acids from ATF6 or the activated form of ATF6 is used as a dominant negative form, and whereby the expression level of the endoplasmic reticulum chaperone genes can be decreased. In this case, there may be used one obtained by expressing a DNA encoding the above polypeptide within the cell.

In addition, when the expression level of the endoplasmic reticulum chaperone genes is decreased, a polypeptide resulting from disruption of an entire or partial portion of a region of 1st to 307th amino acids from the activated form of CREB-RP is used as a dominant negative form, and whereby the expression level of the endoplasmic reticulum chaperone genes can be decreased. In this case, there may be used one obtained by expressing a DNA encoding the above polypeptide within the cell.

(3) Method for Expressing Foreign Protein

There is further provided a method for expressing a foreign protein comprising the method of the present invention for controlling expression of endoplasmic reticulum chaperon genes. The method for expressing a foreign protein is also encompassed in the present invention.

When utilized for control of expression of a foreign gene, 1) a gene encoding the activated form of endoplasmic reticulum stress transcription factor may be simultaneously expressed with a foreign gene located downstream of a promoter for the endoplasmic reticulum chaperone gene, or 2) a gene encoding the activated form of endoplasmic reticulum stress transcription factor may be simultaneously expressed with a DNA in which an appropriate promoter, a foreign gene, or the like is located downstream of the DNA containing an ERSE portion of the endoplasmic reticulum chaperone gene.

1) Embodiment where a gene encoding the activated form of endoplasmic reticulum stress transcription factor is simultaneously expressed with a foreign gene located downstream of a promoter for the endoplasmic reticulum chaperone gene In this embodiment, a vector carrying a gene encoding the activated form of endoplasmic reticulum stress transcription factor may be coexpressed with a vector carrying a foreign gene located downstream of the endoplasmic reticulum chaperone gene. Alternatively, a foreign gene may be expressed by introducing the vector carrying the foreign gene into a previously prepared host capable of controlling expression of a gene encoding the activated form of an endoplasmic reticulum stress transcription factor by endoplasmic reticulum stress.

The vector includes, but not particularly limited to, the vectors mentioned above.

The host used for expression includes, but not particularly limited to, the hosts mentioned above.

The method of transfection using a vector includes, but not particularly limited to, the conventional methods mentioned above.

2) Embodiment where a gene encoding the activated form of an endoplasmic reticulum stress transcription factor is simultaneously expressed with a DNA in which an appropriate promoter, a foreign gene, or the like is located downstream of the DNA containing an ERSE portion of the endoplasmic reticulum chaperone gene The promoter includes not only promoters derived from human GRP78 gene, human GRP94 gene, and human calreticulin gene, but also any foreign promoters. Concrete examples of the foreign promoters include SV40 promoter, cytomegalovirus promoter, retrovirus LTR promoter, β-actin promoter, and the like.

The DNA comprising the ERSE portion of the endoplasmic reticulum chaperone gene can be located at any positions upstream of the transcriptional initiation point, and it is preferably located within 600 bases from the transcriptional initiation point. Further, the orientation of the DNA may be + or −.

The DNA comprising the ERSE portion of the endoplasmic reticulum chaperone gene can be used for an expression vector by incorporating the DNA into generally employed plasmids, cosmids, viruses, and the like.

The cells used for expression include the cells mentioned above. In addition, the transfection of the expression vector may be carried out by a conventional method of transfection mentioned above.

EXAMPLES

The present invention will be described in further detail by means of the following Examples, without intending to limit the scope or spirit of the present invention thereto.

Example 1

Isolation of ERSE (1) Cell Culture

HeLa cells (ATCC CCL2) were cultured in Dulbecco's modified Eagle's medium (glucose at 4.5 g/l) supplemented with 10% fetal calf serum, 2 mM glutamine, 100 unit/ml penicillin and 100 μg/ml streptomycin, at 37° C. in a humidified 5% $CO_2$/95% air atmosphere.

(2) Construction of Reporter Plasmids for Isolating ERSE

Recombinant DNA techniques were performed according to the standard procedures described in *Molecular Cloning: A Laboratory Manual* Second Edition, Cold Spring Harbour Laboratory, Published in 1989, and the like.

A 311 bp fragment of a human GRP78 promoter ([−304 to +7] region; the nucleotide position of the transcription initiation site is defined as +1) was amplified by PCR method with genomic DNA of HeLa cells as a template using two oligonucleotides as primers for+ strand and− strand, wherein the oligonucleotides were prepared on the basis of the sequence of the human GRP78 gene disclosed by Ting et al. (mentioned above). The resulting amplified fragment was inserted into the KpnI-XhoI sites of the pGL3-Basic vector (manufactured by Promega) carrying the sequence encoding firefly luciferase but lacking a eukaryotic promoter or enhancer elements, and thereby being cloned.

Deletion fragments having various lengths of the promoter region [−304 to +7] were prepared by PCR method. The resulting amplified fragment was inserted into the KpnI-XhoI sites of pGL2-Basic vector or pGL2-Promoter vector (manufactured by Promega) carrying SV40 minimal promoter upstream of the sequence encoding firefly luciferase to prepare a reporter promoter for a series of the above deletion mutants.

In order to construct point mutants of the [−139 to −62] and [−65 to −26] regions, synthetic oligonucleotides having appropriate base substitutions were synthesized and annealed, and thereafter the resulting product was ligated to the KpnI-XhoI sites of pGL2-Promoter vector (manufactured by Promega). The ERSE sequences in the GRP78 promoter were mutated using Exsite Site-Directed Mutagenesis Kit manufactured by Stratagene. The resulting fragments were inserted into the KpnI-HindIII sites of pGL3-Basic vector (manufactured by Promega).

A 397-bp fragment of the human GRP94 promoter ([−363 to +34] region) was amplified by PCR method with genomic DNA of HeLa cells as a template using oligonucleotides as primers, wherein the oligonucleotides were prepared on the basis of the sequence of a human GRP94 gene disclosed by Chang et al. [Chang, S. C. et al., Mol. Cell. Biol. 9, 2153–2162 (1989)].

A 511-bp fragment of a human calreticulin promoter region ([−459 to +52] region) was amplified by PCR method with genomic DNA of HeLa cells as a template using oligonucleotides as primers, wherein the oligonucleotides were prepared on the basis of the sequence of a human calreticulin gene disclosed by McCauliffe et al. [McCauliffe, D. P. et al., J. Biol. Chem. 267, 2557–2562 (1992)].

These two promoters were used in experiment for disrupting the ERSE sequences. Plasmids purified by conventional cesium chloride (CsCl) method were used in transient transfection.

(3) Transfection Experiments for Transient Expression of Reporter Plasmids for Isolating ERSE Transfection was carried out by the conventional calcium phosphate method described in the above *Molecular Cloning*, and the like. The HeLa cells were plated onto a 24-well dish so as to have approximately 10% confluency on the day before transfection. One microgram of a reporter plasmid for isolating ERSE and 0.1 µg of a reference plasmid [pRL-SV40 vector (manufactured by Promega) carrying SV40 enhancer and promoter immediately upstream of *Renilla luciferase* gene] were mixed at room temperature in 1×HEPES buffered saline (composition: 50 mM HEPES, 280 mM NaCl, 1.5 mM $Na_2HPO_4$, pH 7.08) containing 250 mM $CaCl_2$ to form $CaPO_4$-DNA complex. The cells were incubated with the resulting $CaPO_4$-DNA complex for 16 hours at 37° C., washed with phosphate buffered saline three times, and further incubated in a fresh medium.

(4) Determination of Activity

After culturing the transfection cells obtained in item (3) above for 48 hours, the cells were harvested with a rubber policeman. The harvested cells were suspended in 100 µl lysis buffer (100 mM potassium phosphate buffer, 1 mM dithiothreitol, pH 7.8). Cells were disrupted by freeze-thawing the resulting cell suspension three times, whereby obtaining a cell-free extract.

In order to induce endoplasmic reticulum stress response, cells were treated with 2 µg/ml tunicamycin 16 hours prior to harvesting the cells.

The firefly luciferase and *Renilla luciferase* activities were determined with 5 µl of cell lysate using the Dual Luciferase Reporter Assay Systems (manufactured by Promega) according to the instruction of the manufacturer. The above activities were measured using luminometer (manufactured by Labsystems, trade name: Luminoskan) within a linear range. The relative luciferase activity was found by normalizing the firefly luciferase activity to the *Renilla luciferase* activity.

(5) Identification of ERSE

Figure 4:
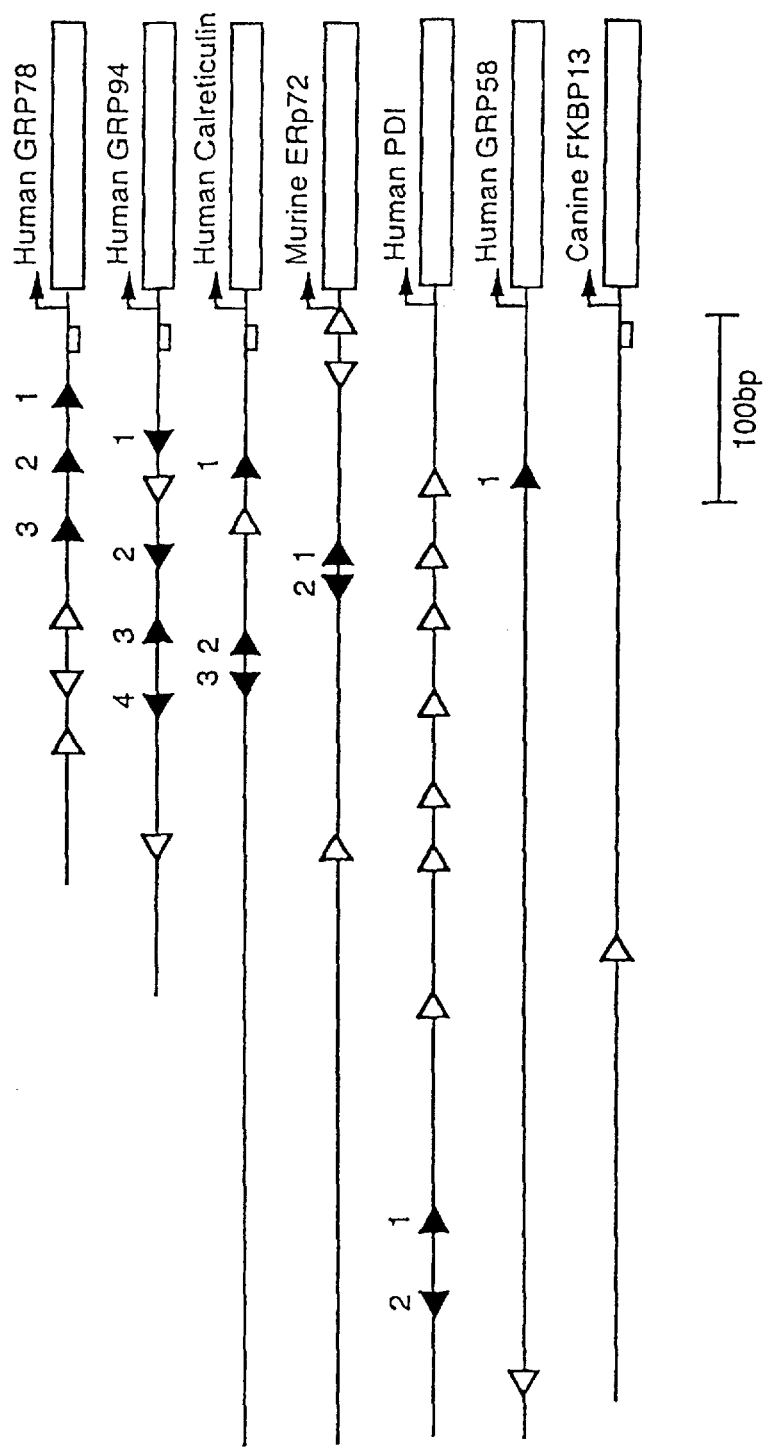
FIG. 4 shows locations and directions of ERSE-like sequences in various GRP promoters as indicated by closed arrows. CCAAT and TATA sequences are indicated by open arrows and small open boxes, respectively.

The endoplasmic reticulum stress response promoter of mammalian GRP gene was remarked to contain numerous CCAAT motifs. As shown in FIG. 3, the structural motif CCAAT-9nt-CCACG (SEQ ID NO:1) is found in promoters for GRP78, GRP94 and calreticulin. As shown in FIGS. 3 and 4, in these CCAAT sequence and flanking sequences, all of the GRP promoters tested except for FKBP13 have been found to contain multi-copy of similar motifs. As shown in FIG. 1, both of CORE and C1 region previously defined in the GRP78 promoter actually contains this motif.

Interestingly, as shown in FIG. 2, the mammalian GRP78 promoter comprises continuous repeated sequences, each of which contains this motif, and it is deduced that the repeated sequences are caused by the replication during the evolution process. From these findings, it has been suggested that the motif is specifically contained in the mammalian unfolded protein response (UPR). Since the motif is structurally different from UPRE responding to the yeast UPR, this motif is referred to as an endoplasmic reticulum stress response element (ERSE). In addition, the ERSE-like sequences are found in vertebrates, plants, fungi, and the like as shown in FIG. 5.

(6) Involvement in Transcriptional Induction of ERSE Motifs of GRP78, GRP94 and Calreticulin In order to test whether or not the ERSE motif is important in the induction of GRP78, GRP94 and calreticulin, each of the promoters shown on lines 1 to 14 of FIG. 6 was ligated to a firefly luciferase gene as a reporter gene, and the ligated product was transfected to HeLa cells in the same manner as in item (3) above. UPR was induced by using tunicamycin (hereinafter simply referred to as "TM"), an inhibitor for N-glycosylation of a protein.

As shown in FIG. 6, intact GRP78 promoter has increased the expression of luciferase in the TM-treated cells (FIG. 6, line 2, closed bar) by 5-fold over that of the control (line 2, open bar). The extent of expression was comparable to the one observed in the previous studies [Ting, J. et al., DNA 7, 275–286 (1988); Wooden, S. K. et al., Mol. Cell Biol. 11, 5612–5623 (1991)] (5 to 7 times); and that of the endogenous GRP78 protein level (5 to 8 times) shown in panel (C) of FIG. 19.

In the intact GRP94 promoter and the calreticulin promoter, the luciferase expression was increased by the TM treatment by 8- and 4-fold, respectively, as shown in FIG. 6, lines 8 and 12. This expression level agrees with the one previously reported by Ramakrishnan, M. et al., DNA Cell Biol. 14, 373–384 (1995); and Waser, M. et al., J. Cell Biol. 138, 547–557 (1997).

In addition, as shown on line 3 of FIG. 6, when the ERSE1 motif was selectively removed from the GRP promoter, the induction of luciferase was drastically reduced. As shown on lines 4 to 6 of FIG. 6, the induction of the luciferase decreased by the removal of the ERSE1 motif was completely abolished by further disruption of ERSE2 and/or ERSE3.

As in the case of GRP78, the disruption of ERSE1 of the GRP94 promoter (shown on line 9 of FIG. 6) drastically decreased the induction, and as shown on line 10, the induction was completely disrupted by simultaneous removal of ERSE1 and ERSE3.

As shown on line 13 of FIG. 6, the removal of ERSE3 alone at a distal position of the calreticulin promoter had substantially no effect, but as shown on line 14, the disruption of both ERSE3 and ERSE2 of the calreticulin promoter completely prevented induction (line 14).

Figure 7:
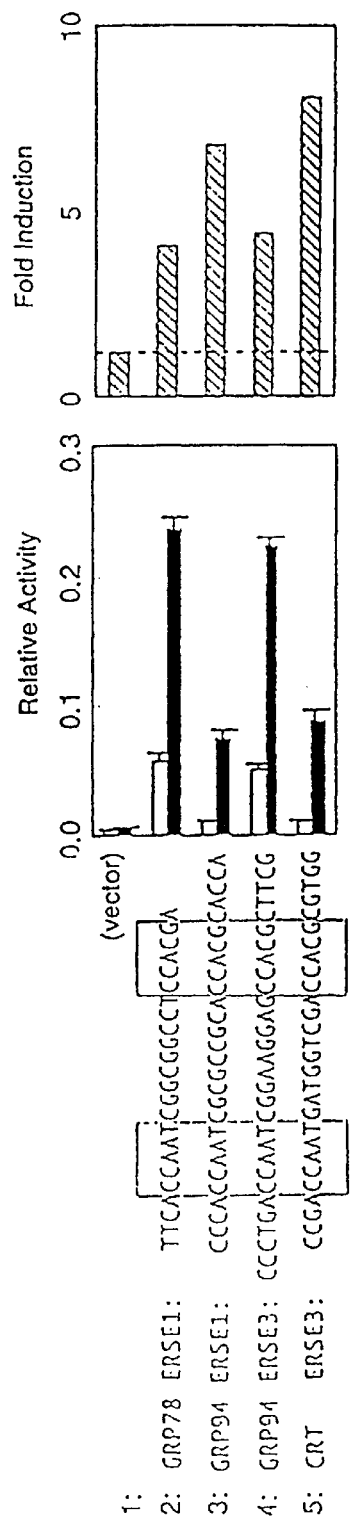
FIG. 7 shows involvement of ERSE motifs (SEQ ID NOS:60–63)in transcriptional induction on GRP78, GRP94 and calreticulin. Oligonucleotides encoding each ERSE with indicated flanking sequences as shown in the figure were inserted into the BglII site of the pGL3-Promoter vector. The relative luciferase activity and the fold induction were determined in the manner as described in FIG. 6 by four independent, transient expression assays.

As shown in FIG. 7, when several deduced ERSEs each carrying some flanking sequences (each of ERSEs of GRP78, GRP94 and calreticulin) were at positions upstream of the heterologous promoter (SV40 minimal promoter), since these ERSEs had markedly induced luciferase activity, there has been suggested that these ERSEs are actually functioning.

In addition, the effects by the orientation of ERSE1 derived from human GRP78 promoter were evaluated. As a result, the same level of activities was exhibited regardless of its orientation. It was suggested from the above results that the ERSE motif is an essential and sufficient cis-acting element for induction of GRP78, GRP94 and calreticulin and perhaps other GRPS.

In the ERSE motif, in order to determine whether or not the essential nucleotide sequence is actually CCAAT(N)$_9$CCACG (SEQ ID NO:1) a point mutation (transversion) was introduced into each of the nucleotides of ERSE1 derived from human GRP78 promoter used in the above experiment.

Figure 8:
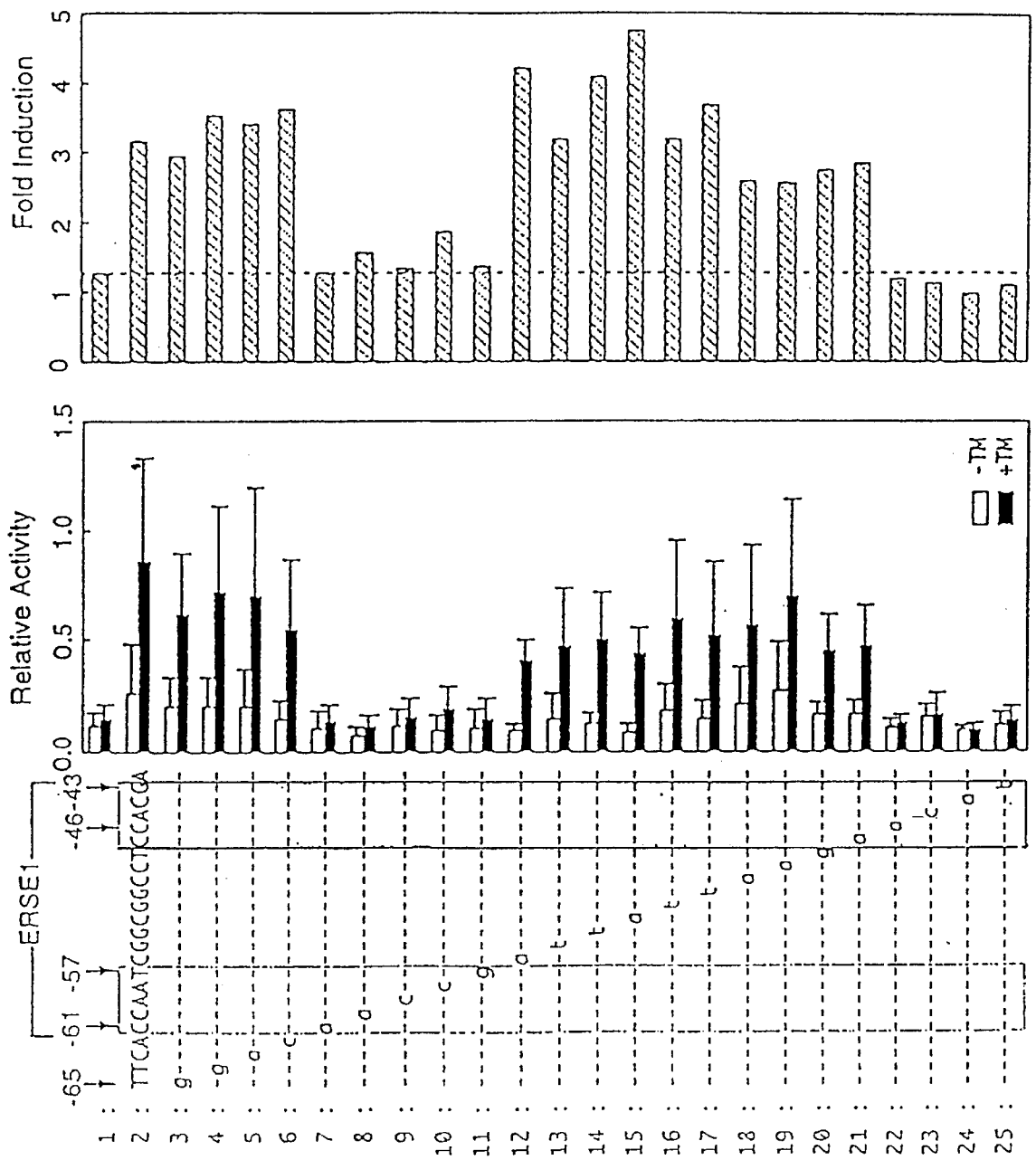
FIG. 8 shows nucleotides in ERSE1 (SEQ ID NO:64) from the human GRP78 promoter required for transcriptional induction. Each nucleotide of the segment [−65 to −43] was substituted by transversion (in the figure, substituted nucleotides indicated by lower case letters). Thereafter, resulting mutated fragment was inserted into the XhoI-BglII sites of the pGL2-Promoter vector. The data are represented as the mean of four independent experiments.
Figure 9:
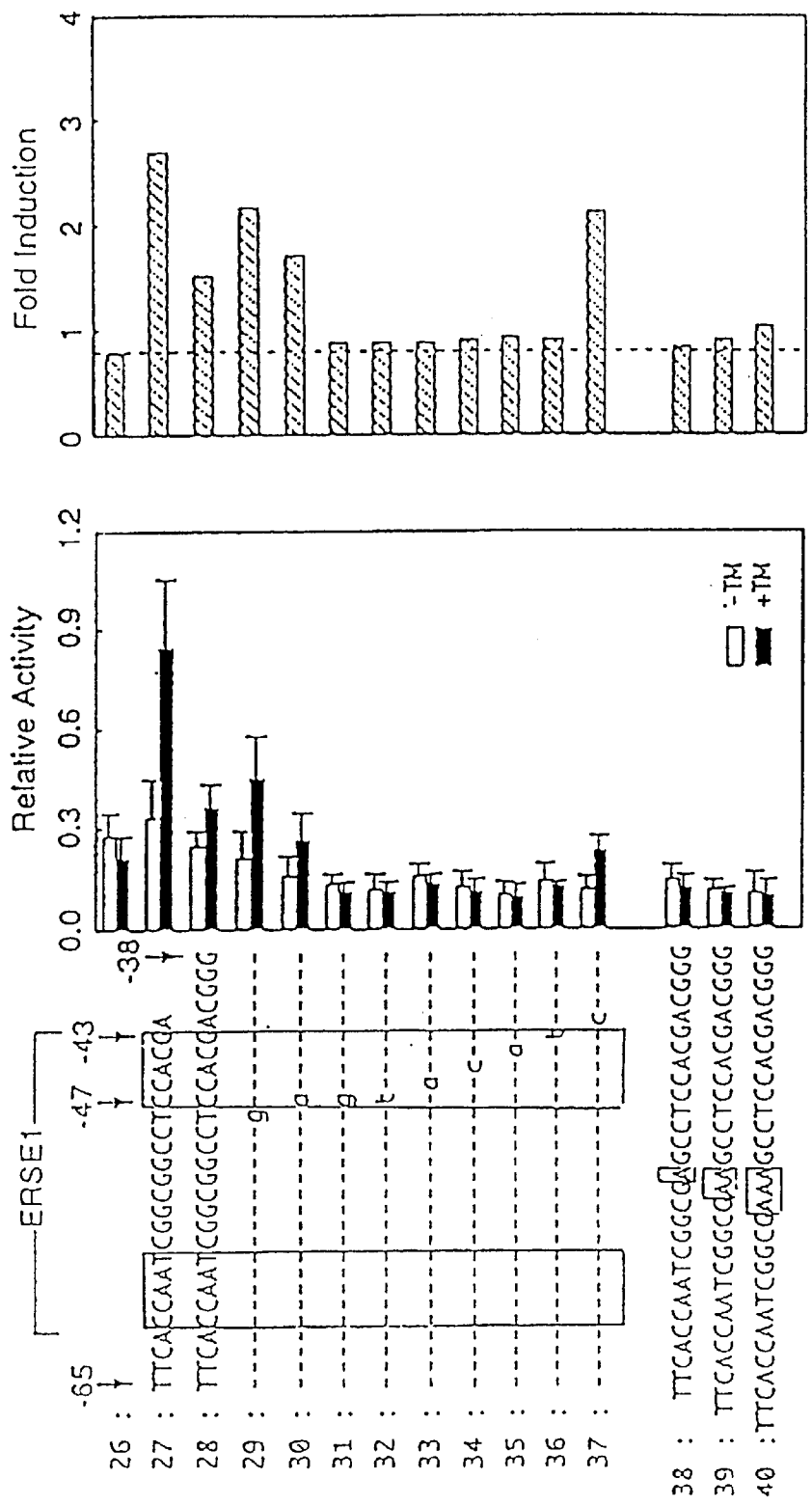
FIG. 9 shows nucleotides in ERSE1 (SEQ ID NOS:65–69) from the human GRP78 promoter required for transcriptional induction. Each CCACG and neighboring sequences were changed to those indicated by lowercase letters. Mutated fragments of the segment [−65 to −38] were inserted into the pGL2-Promoter vector in the same manner as those shown FIG. 8. Insertion mutation each comprising additional A's between CCAAT and CCACG were also shown in lines 38 to 40. The data are represnted as the mean of four independent experiments.

As a result, as shown in FIGS. 8 and 9, while the substitutions of other nucleotides had substantially no effect, some of the substitutions among the nucleotides [−61 to −57] (FIG. 8, lines 7 to 11) or [−46 to −43] (FIG. 8, lines 22 to 25) almost completely inhibited the induction. It was strongly suggested from the above results that CCAAT (−61 to −57) and CACG (−46 to −43) were essential for the induction.

As shown in FIG. 3, since the nucleotide C[−47] was well conserved, it was further analyzed in detail. In this experiment, a [−65 to −38] segment exhibiting a markedly low response as compared to a [−65 to −42] segment (FIG. 9, line 27) was used. While there were substantially no effects when C[−47] was changed to A (see line 30; line 21), as shown on lines 31 and 32 of FIG. 9, the induction was completely disrupted when C[−47] was changed to G or T. Therefore, it was shown that C[−47] is also essential for induction. By contrast, there were exhibited substantially no effects in the conversion of A[−42] to other nucleotides. Further, since the insertion of 1 to 3 nucleotides shown on lines 38 to 40 completely disrupted the induction of luciferase, there was shown that the distance CCAAT (−61 to −57) to CCACG (−47 to −43) is important. These results show that the essential sequene of the ERSE1 motif from the human GRP78 promoter is 19 nucleotides stretch [CCAAT (N)$_9$CCACG](SEQ ID NO:1).

(7) Response to Other Endoplasmic Reticulum Stress Inducer

In order to induce experimentally the endoplasmic reticulum stress response of the mammalian GRP, in addition to tunicamycin used in all experiments, the cells were treated with various chemicals including calcium ionophore A23187 depleting the calcium storage of the endoplasmic reticulum; thapsigargin inhibiting $Ca^{2+}$-ATPase of the endoplasmic reticulum and excretion of calcium ions from the endoplasmic reticulum, or the like. The endoplasmic reticulum stress response of the human GRP promoter to A23187 and thapsigargin were tested. The results: are shown in FIG. 10, wherein lines 1, 5, 9, 13, 17 and 21 indicate the relative activity when no inducer is added as a control; lines 2, 6, 10, 14, 18 and 22 indicate the relative activity when tunicamycin is added; lines 3, 7, 11, 15, 19 and 23 indicate the relative activity when calcium ionophore A23187 is added; and lines 4, 8, 12, 16, 20 and 24 indicate the relative activity when thapsigargin is added.

Figure 10:
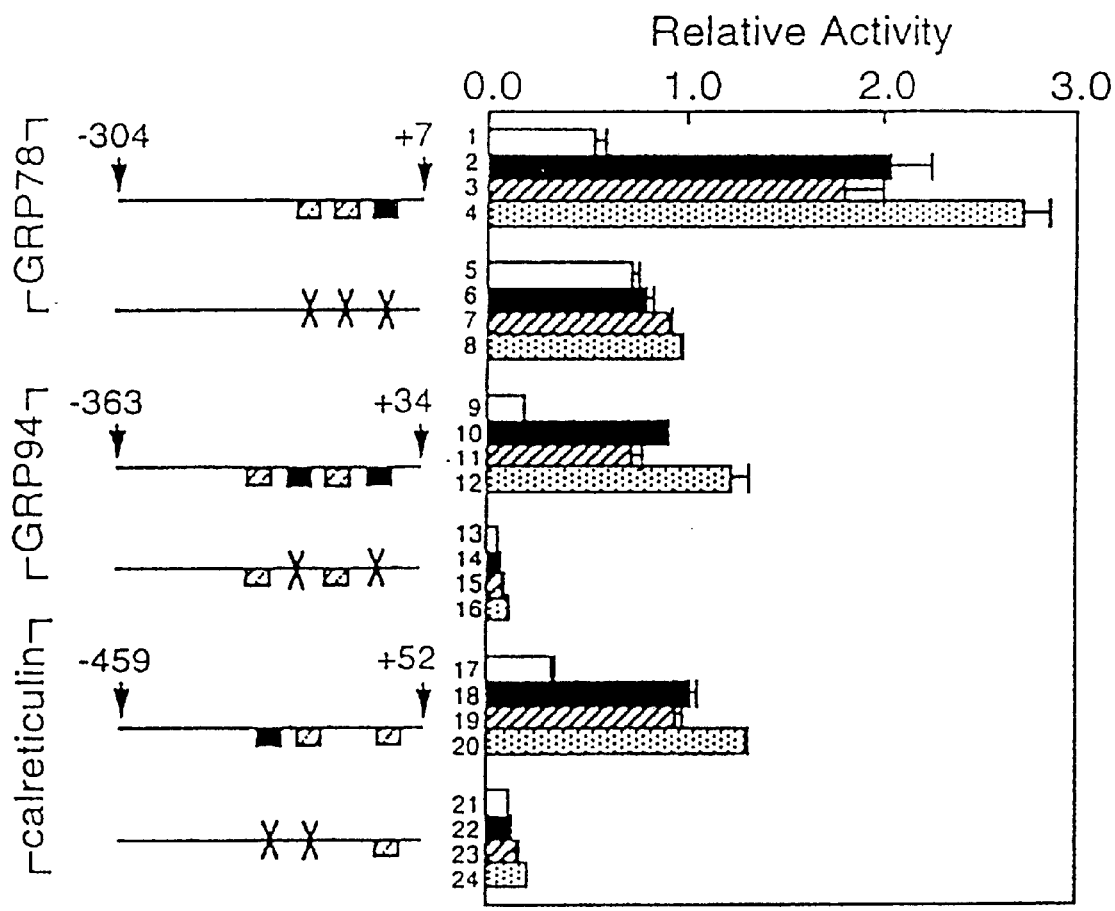
FIG. 10 shows effects of various ER stress-inducing reagents on ERSE-mediated induction of human GRP78, GRP94 and calreticulin. Cells transiently transfected with the indicated constructs were treated for 16 hours with 2 μg/ml TM (closed bars), 1 μM A23187 (hatched bars) or 100 nM Tg (dotted bars). Each of the constructs as shown in the figure corresponds to the constructs in FIG. 6. The data were obtained from four independent experiments.

Since the transcriptional induction by each treatment of GRP78 (FIG. 10, lines 1 to 4), GRP94 (FIG. 10, lines 9 to 12), and calreticulin (FIG. 10, lines 17 to 20) was completely prevented by the disruption of ERSE as shown on lines 5 to 8, 13 to 16, and 21 to 24 of FIG. 10, there was exhibited that ERSE is required for the induction of GRP not only by tunicamycin but also by other inducers.

Example 2

One-Hybrid Screening for cDNA Encoding ERSE Binding Protein

The reporter plasmid for one-hybrid screening was constructed essentially according to the method described by Mori, K. et al. [*Genes Cells* 1, 803–817 (1996)].

Figure 11:
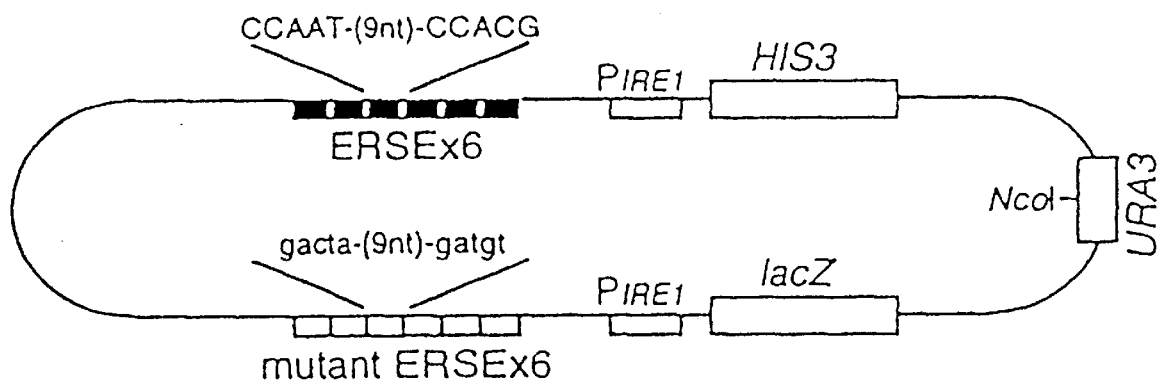
FIG. 11 shows a structure of a reporter plasmid used for one-hybrid screening in yeast.

Six tandem repeats of ERSE1 sequence from the human GRP78 promoter [5'-CCTTCA<u>CCAAT</u>CGGCGGCCT<u>CCACG</u>ACGG-3' (SEQ ID NO: 35)] were inserted upstream of the yeast HIS3 gene ligated to the IRE1 promoter, while six tandem repeats of mutant ERSE repeats [5'-CCTTCAgactaCGGCGGCCTgatgtACGG-3' (SEQ ID NO: 36)] were inserted upstream of *Escherichia coli* lacZ gene ligated to the IRE1 promoter. The structure of the above reporter plasmid is schematically shown in FIG. 11.

The above reporter plasmids were respectively linearized at the NcoI site present in URA3 gene, and one copy thereof was integrated into the ura3–52 locus of yeast strain KMY1015 (MATα leu2-3, 112 ura3-52 his3-Δ200 trp-Δ901 lys2-801 irelΔ::TRP1) [Mori, K. et al., *Genes Cells* 1, 803–817 (1996)]. The resulting yeast strain (hereinafter, referred as KMY1015-ERSE) was used as a host for eliminating unexpected activation via UPR. The KMY1015-ERSE was unable to grow in the absence of histidine and expressed low β-galactosidase activity due to low basal activity of the IRE1 promoter.

A human lymphocyte cDNA library prepared by using a multicopy plasmid vector carrying the activation domain of yeast transcriptional activator Gal4p (GAL4AD) immediately upstream of the cDNA cloning site was kindly provided by Dr. S. J. Elledge of Baylor College of Medicine through Dr. N. Hayashi of Kanazawa University.

The ERSE-bound protein, when fused with an active domain of yeast transcription factor Gal4p (GAL4AD), is expected to activate the transcription of the reporter. gene HIS3 in an ERSE-dependent manner. Therefore, transformants were prepared using yeast as a host by introducing the above human lymphocyte cDNA library provided by Dr. Ellege, and about 4,300,000 transformants were screened. As a result, 8 clones showing strong Hiss phenotype were obtained. Among the resulting clones, clones expressing β-galactosidase at a high level despite the absence of the functional ERSE in the upstream region were discarded. As a result, there was obtained clone #3, in which the transcription of the reporter gene increases in an ERSE-dependent manner.

In order to examine the ERSE-dependency of the transcriptional activation by the clone 3, clone 3-GAL4AD fusion protein was expressed together with various reporter plasmids in which intact ERSEs and mutated ERSEs were placed upstream of the lacZ gene ligated with the IRE1 promoter. The results are shown in FIG. 12.

Figure 12:
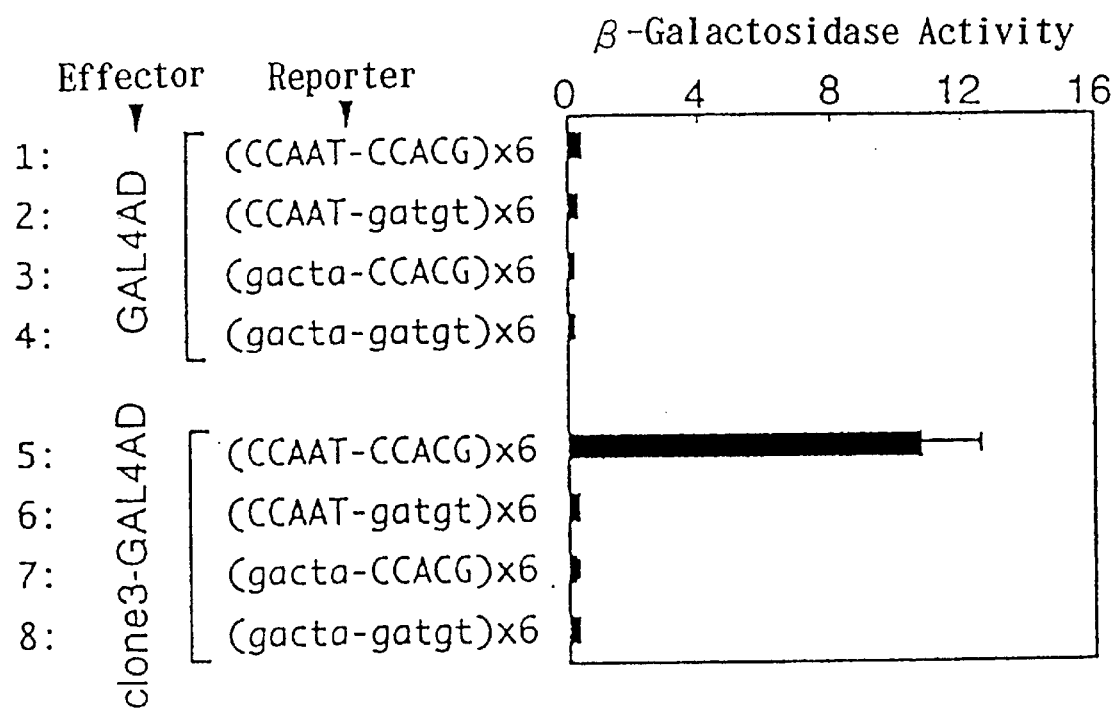
FIG. 12 shows effects of a clone 3-GAL4AD fusion protein on the reporter gene expression. An effector plasmid carrying agene encoding either GAL4AD protein alone or clone 3-GAL4AD fusion protein was introduced into yeast strain KMY1015 harboring a reporter plasmid of the lac Z gene under the control of intact ERSE (5'-CCTTCACCAATCGGCGGCCTCCACGACGG-3') (SEQ ID NO:70) or mutant ERSE (in the figure, mutated-nucleotides are indicated in lowercase).

As shown in FIG. 12, when the intact ERSE was placed upstream of the reporter gene, the β-galactosidase activity level was remarkably increased by the plasmid expressing clone 3-GAL4AD as an effector (line 5) as compared with the β-galactosidase activity level by the control plasmid expressing. GAL4AD alone (line 1).

In addition, the increase by the clone 3-GAL4AD, as shown on lines 6 to 8 of FIG. 12, was completely disrupted by using mutated ERSE lacking either one or both of CCAAT or CCACG. The results, as shown in FIGS. 8 and 9, are relevant to the requirement of intact CCAAT and CCACG for transcriptional activation observed in the HeLa cells.

It is unlikely possibility that ectopic expression of a protein derived from clone 3 in yeast cells causes endoplasmic reticulum stress by the translocation of the clone 3-GAL4AD fusion protein into the endoplasmic reticulum lumen, which in turn results in an enhanced transcription of a reporter gene directly via yeast UPR pathway in the following two aspects. First, a yeast strain lacking a sensor molecule Ire1p for endoplasmic reticulum stress was used as a host. Second, ERSE is not functional in yeast as a UPR-specific cis-acting element.

As a result of the nucleotide sequence analysis by a conventional method, it was elucidated that clone 3 encodes a known transcription factor, ATF6 [Hai, T. W. et al., *Genes Dev.* 3, 2083–2090 (1989)], a member of the ATF/CREB family containing bZIP motif as a DNA-binding domain.

Interestingly, as shown in FIG. 13, the basic region of ATF6 shows marked similarity with a basic region of yeast Hac1p. Although the function of ATF6 is not made evident., ATF6 is originally cloned as a partial cDNA weakly bound to a cAMP response element, and is recently re-isolated as a protein bound to a serum response factor.

Example 3

Isolation of Entire cDNA Encoding ATF6 and CREB-RP

A portion of 5'-region of mRNA for ATF6 thought to be lacking in clone #3 was isolated by 5'RACE using HeLa cells RNA. Here, 5'RACE method employed 5'RACE System (manufactured by Life Technologies Inc.). An intact ATF6 cDNA obtained as described above has a length of 2509 bp, and a protein having 670 amino acids was encoded (The accession number for GeneBank Data Base is AB015856). The deduced amino acid sequence was different from the sequence reported by Zhu et al. [*Mol. Cell. Biol.* 17, 4957–4966 (1997)] by 4 residues which are deduced to reflect an allele polymorphism.

An entire cDNA of CREB-RP having a similar molecular structure and homology in the amino acid sequence is cloned from HeLa cells RNA by PCR on the basis of the published sequence [Min, J. et al., *Genomics* 30, 149–156 (1995); Khanna, A. et al., *Biochem. J.* 319, 81–89 (1996)].

Example 4

Construction of Effector Plasmid

An entire cDNA was inserted into the HindIII-XhoI sites or BamHI-EcoRI sites immediately downstream of the CMV promoter of pcDNA3.1(+) vector (manufactured by Invitrogen) to construct an effector plasmid for expressing ATF6 or CREB-RP, respectively.

Example 5

ERSE-Dependency of Transcriptional Activity
(1) Test for ERSE-Dependency ATF6 on Transcriptional Activity In order to examine whether or not ATF6 is involved in the transcriptional regulation of the GRP gene in mammalian cells, HeLa cells were co-transfected with an effector plasmid carrying a full-length ATF6 cDNA and a reporter plasmid resulting from ligation of the firefly luciferase gene to downstream of the intact GRP promoter or a mutant GRP promoter, and GRP promoter activity was evaluated from the luciferase activity. The results are shown in FIG. 14.

Figure 14:
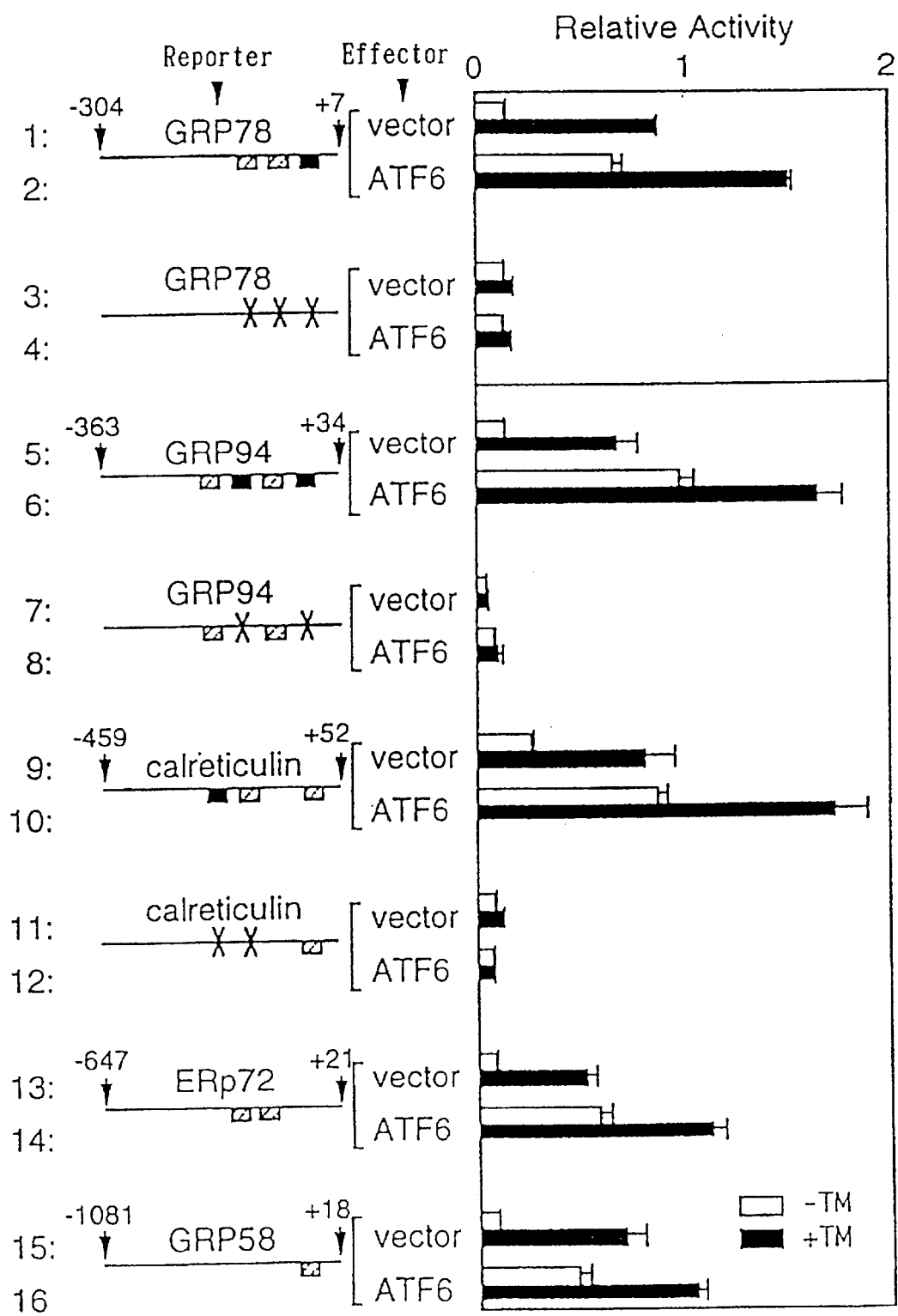
FIG. 14 shows effects of ATF6 overexpression on GRP promoters. 100 ng of an effector plasmid carrying a full-length ATF6 cDNA or plasmid vector alone was cotransfected into HeLa cells with 1 μg of a reporter plasmid containing luciferase gene fused with intact or mutant GRP promoters. The mutant promoter constructs used correspond to those of FIG. 6. Closed bars and open bars indicated cells treated with or without 2 μg/ml tunicamycin (in the figure, referred to as "TM") for 16 hours, respectively. Experiments were repeated four times.

As indicated by the open bars on lines 1 and 2 in FIG. 14, the ATF6 expression plasmid increased the luciferase expression from the GRP78 promoter having intact ERSE sequences by 5-fold over the control level of the aforementioned vector in the absence of TM, but the expression was not affected from the mutant GRP78 promoter lacking all of the three ERSE sequences.

In addition, the ATF6 effector plasmid further increased the β-galactosidase expression from the GRP78 promoter having intact ERSE sequences in the presence of TM, as indicated by the closed bars on lines 1 and 2 in FIG. 14, while the luciferase expression level did not increase from the mutant GRP78 promoter, as indicated by the closed bars on lines 3 and 4.

Figure 15:
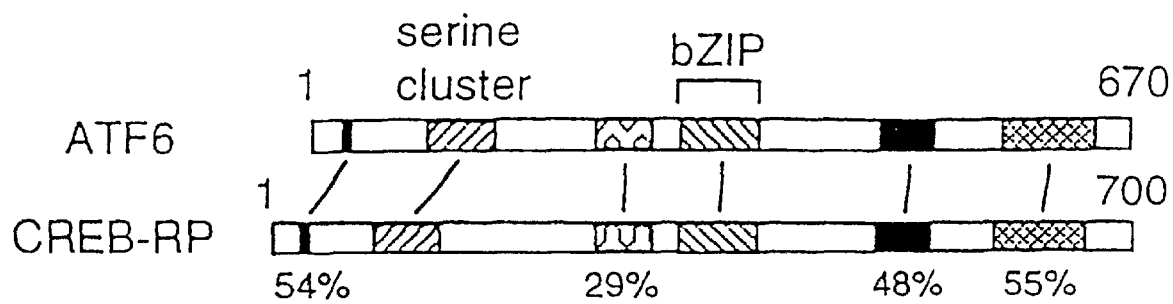
FIG. 15 shows structural homology between ATF6 and CREB-RP. A region showing remarkable homology is indicated by boxes, and the identity is indicated by %.

Similar results were obtained with other GRP promoters: GRP94, calreticulin, ERp72 and GRP58. The results shown on lines 5 through 16 definitely suggested that enhanced expression of ATF6 is capable of specifically activating transcription of the GRP genes via ERSE, regardless of the presence or absence of the endoplasmic reticulum stress.
(2) Test for ERSE-Dependency on CREB-RP Transcriptional Activity As shown in FIG. 15, CREB-RP [Min, J. et al., *Genomics* 30, 149–156 (1995)] shows marked similarity to ATF6 both in the entire structure and in the deduced amino acid sequence, especially in its basic region, having 21 out of the 23 residues in common, and the remaining 2 being similar basic residues. Also, as shown in FIG. 13, CREB-RP possesses the highest similarity among the known members of the human ATF/CREB family.

Figure 16:
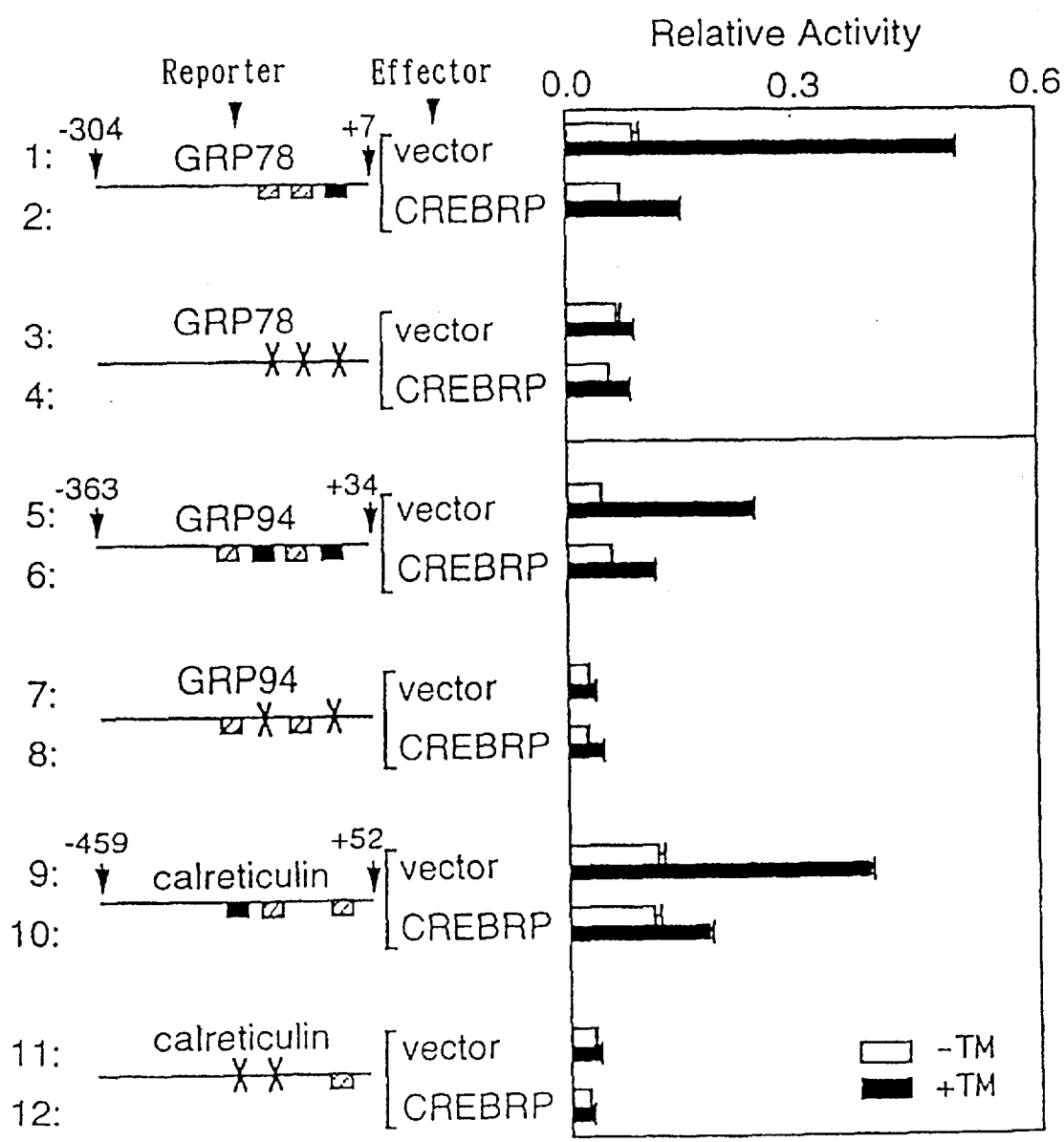
FIG. 16 shows effects of CREB-RP overexpression on GRP promoter. An effector plasmid carrying a full-length CREB-RP gene was cotransfected into HeLa cells harboring a reporter plasmid in the same manner as in FIG. 14. Experiments were repeated four times. In the figure, TM indicates tunicamycin.

Therefore, with these findings in mind, a test was carried out to determine whether or not CREB-RP overexpression affects the activity of the GRP promoter. Interestingly, as indicated by the open bars on lines 1 and 2 in FIG. 16, co-transfection of the CREB-RP expression plasmid hardly affected the reporter expression from the intact GRP78 promoter in the absence of TM, while the expression was markedly suppressed in the presence of TM.

In contrast, as shown on lines 3 and 4, CREB-RP overexpression did not affect the expression from the mutant GRP78 promoter in the presence or absence of TM. Because similar results were obtained using the GRP94 or calreticulin promoter, it has been suggested that CREB-RP overexpression prevents the endoplasmic reticulum stress-induced transcription of the GRP gene via an endogenous transactivator.

It is shown from the results of items (1) and (2) in Example 5 that the closely related transcription factors ATF6 and CREB-RP have definitely opposite effects on induction of target genes, and it was also objected to the possibility that ATF6 overexpression simply activated GRP transcription indirectly by producing endoplasmic reticulum stress in HeLa cells.

Example 6

ATF6 Regulation by Endoplasmic Reticulum Stress

A test was carried out to determine whether or not ATF6 expression is regulated by endoplasmic reticulum stress on an mRNA level or protein level.
(1) Northern Blot Hybridization Northern blotting was carried out in accordance with the standard method described in *Molecular Cloning: A Laboratory Manual*, Second Edition [Sambrook, et al. (1989)]. Concretely, 10 μg of a poly-A$^+$ RNA, prepared from HeLa cells using oligo(dT) magnetic particles (manufactured by Dynabeads), was subjected to electrophoresis on 1% agarose gel containing 2.2 M formaldehyde, transferred to a nylon membrane, and hybridized with a radiolabeled cDNA specific to either ATF6 or GAPDH.

Figure 17:
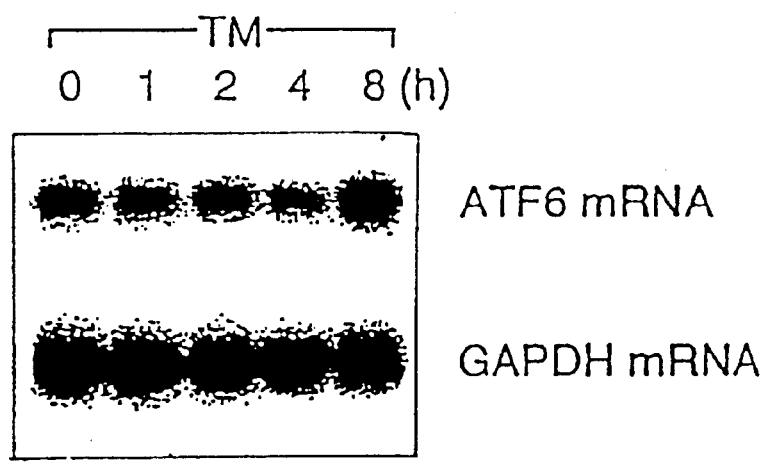
FIG. 17 shows Northern blot hybridization analysis for ATF6 mRNA. HeLa cells were treated with 2 μg/ml tunicamycin (in the figure, referred to as "TM") for indicated period.

As shown in FIG. 17, Northern hybridization analysis revealed the presence of a single band for 2.5 kb ATF6 mRNA in untreated HeLa cells, as reported by Zhu et al. [Zhu, C. et al., *Mol. Cell Biol.* 17, 4957–4966 (1997)]. In addition, unlike the recently identified splicing system of an yeast HAC1 mRNA, which is specifically induced by endoplasmic reticulum stress [Cox, J. S. et al., *Cell* 87, 391–404 (1996); Kawahara, T. et al., *Mol. Biol. Cell* 8, 1845–1862 (1997)], neither an expression level nor a size of ATF6 mRNA was affected by TM treatment.

(2) Preparation of Antisera and Immunoblotting

Two types of antisera against ATF6, i.e., anti-B03N and anti-ATF6 (N21–34), were prepared. The anti-B03N antiserum was obtained by immunizing a rabbit with a fusion protein of N-terminal portion (6th to 307th residues) of ATF6 with the *Escherichia coli* maltose-binding protein, which had been expressed in *Escherichia coli* cells and purified. The anti-B03 antiserum thus obtained was treated with CH-Sepharose 4B (manufactured by Amersham Pharmacia Biotech) on which the soluble proteins of *Escherichia coli*, previously transformed with the maltose-binding protein expression plasmid pMAL-c2 (manufactured by New England Biolab), were immobilized, to yield a flow-through fraction for the purified ATF6 antibody. The anti-ATF6 (N21–34) antiserum was obtained by immunizing with the keyhole limpet hemocyanin conjugate-synthesized peptide of 14 N-terminal amino acids (21st to 34th residues) of ATF6. The anti-GRP78 and anti-HSP70 antisera were obtained from Stressgen Biotechnologies Corporation.

In vitro translation of ATF6 was carried out using ATF6 cDNA and the TNT T7 Quick Coupled Transcription/Translation System (manufactured by Promega).

By lysing 1×106 HeLa cells in 60 μl of 1×sample buffer (62.5 mM Tris-HCl (pH 6.8), 2% SDS, 350 mM dithiothreitol and 0.01% bromophenol blue), a whole cell extract was prepared. This lysate was boiled according to the standard protocol (*Molecular Cloning: A Laboratory Manual*, Second Edition), aliquot (2 μl) of which lysate was subjected to electrophoresis on 10% SDS polyacrylamide gel, transferred onto a Hybond ECL filter (manufactured by Amersham Pharmacia Biotech), and reacted with various antisera. A pre-stained SDS-PAGE standard (manufactured by Bio-Rad) was used as a size marker. Using an ECL Western blotting detection kit (manufactured by Amersham Pharmacia Biotech), each antigen was detected.

ATF6, previously known to be constitutively expressed in both HeLa cells and COS cells [Zhu, C. et al., *Mol. Cell Biol.* 17, 4957–4966 (1997)], was analyzed by immunoblotting. The results are shown in FIG. 18.

Figure 18:
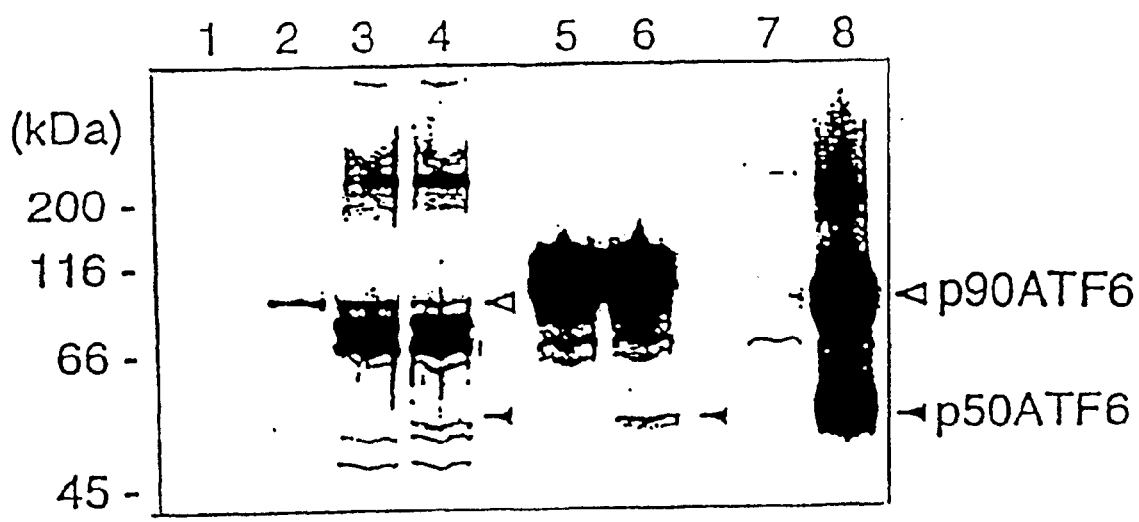
FIG. 18 shows immunoblotting analysis of ATF6 protein in vitro translation was carried out using reticulocyte lysate with a control vector (lane 1) or ATF6 cDNA (lane 2). Whole cell extracts were prepared from HeLa cells that had been untreated (lanes 3 and 5) or treated with 2 μg/ml TM for 4 hours (lanes 4 and 6) or from HeLa cells that had been transfected with a control vector (lane 7) or an ATF6 expression plasmid (lane 8). Proteins were detected by using anti-B03N antisera (lanes 1 to 4, 7 and 8) or anti-peptide [anti-ATF6 (N21–34)] antisera (lanes 5 and 6). The positions of the 90 kDa-band (p90ATF6) and 50 kDa-band (p50ATF6) are indicated by open and closed arrows, respectively.

When in vitro translation was carried out using a reticulocyte lysate, ATF6 was detected as a single band of 90 kDa molecular weight by the anti-B03N antiserum, as shown on lane 2 in FIG. 18. It was also detected by the anti-peptide (anti-ATF6(N21–34)) antiserum as a single band of 90 kDa molecular weight. These molecular weights were greater than the calculated molecular weight of 74.57 kDa, as in the report of Zhu et al.

In contrast, as shown on lane 3, the anti-B03N antiserum reacted with several kinds of proteins in the extract from untreated HeLa cells. Of these proteins, the mobility of the band indicated by the open arrow corresponded to the band from in vitro translated ATF6. When HeLa cells were treated with TM for 4 hours, the 90 kDa band decreased, whereas a new 50 kDa band indicated by the closed arrow appeared instead, as shown on lane 4. No other cross-reacted bands were affected.

Importantly, this 50 kDa protein was also detected by the anti-peptide (anti-ATF6 (N21–34)) antiserum (lane 6).

Furthermore, both the 90 kDa and 50 kDa proteins were constitutively present in the extract from ATF6 overexpressing cells (lane 8) but not in the extract from control cells (lane 7), and no other protein bands were produced in excess under the same conditions. This finding suggests that these two proteins may be actually encoded by ATF6 cDNA. The 90 kDa and 50 kDa proteins were designated as p90ATF6 and p50ATF6, respectively.

Example 7

Correlation Between p50ATF6 and Intracellular UPR Activity

In order to determine whether or not the appearance of p50ATF6 is associated with the intracellular UPR activity, stress-induced p50ATF6 appearance and GRP78 expression were monitored with the passage of time by immunoblotting. The results are shown in FIG. 19.

Figure 19:
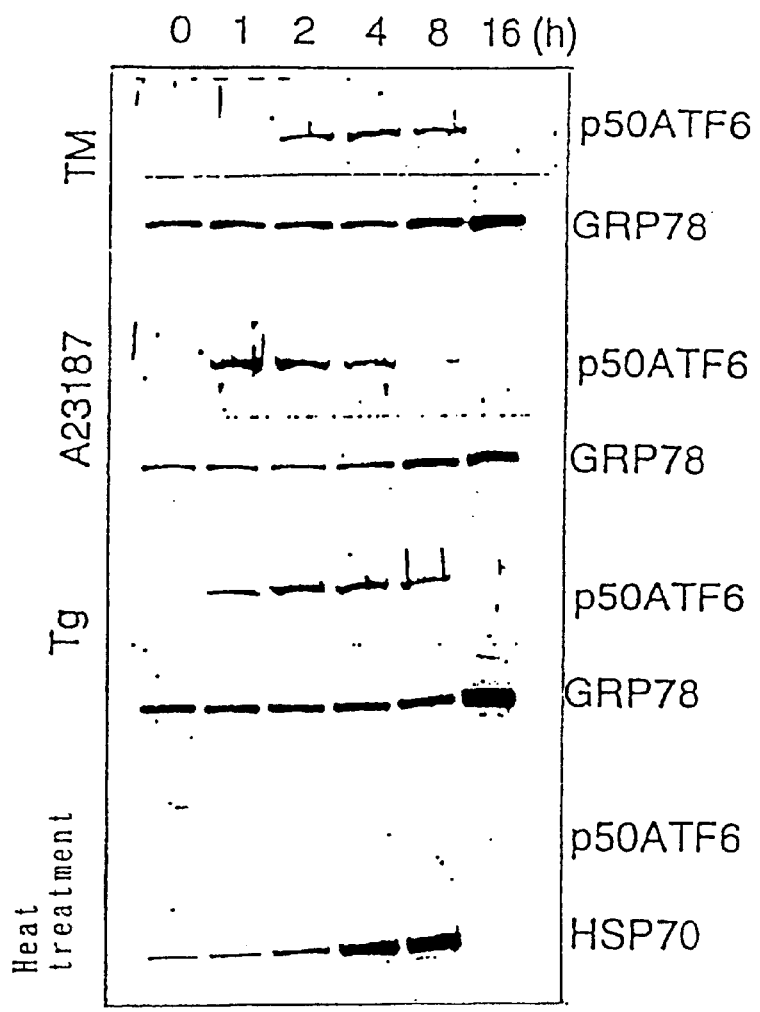
FIG. 19 shows the correlation of the appearance of p50ATF6 with the intracellular UPR activity. HeLa cells were treated with 2 μg/ml TM, 7 μM A23187 or 300 μM thapsigargin (in the figure, simply referred to as "Tg") for the indicated period. Alternatively, HeLa cells which were treated separately from the above treated cells were heat-shocked at 43° C. for 1 hour and then recovered at 37° C. for the indicated period. Whole cell extracts were prepared and analyzed by immunoblotting using an anti-B03N antiserum or an antiserum specific to either GRP78 or HSP70.

As shown in FIG. 19, increase in GRP78 was detected 8 hours after the TM treatment, whereas increase in p50ATF6 became detectable within 2 hours, reaching a peak at 4 to 8 hours, then showing a decrease. Similarly, p50ATF6 appeared in advance of GRP78 induction even in cells treated with A23187 or thapsigargin (indicated by Tg in the figure).

However, in cells subjected to heat shock, p50ATF6 was hardly detected, even though the definite induction of HSP70 was found.

These results strongly suggest that the conversion of p90ATF6 to p50ATF6 is an important regulation process in mammalian UPR.

Example 8

Conversion of p90ATF6 to p50ATF6 by Endoplasmic Reticulum Stress

In order to determine whether or not p90ATF6 is directly converted to p50ATF6 by endoplasmic reticulum stress, quantitative changes in p90ATF6, p50ATF6 and the target protein GRP78 in TM-treated HeLa cells were evaluated with the passage of time by immunoblotting using the purified ATF6 antibody.

Figure 20:
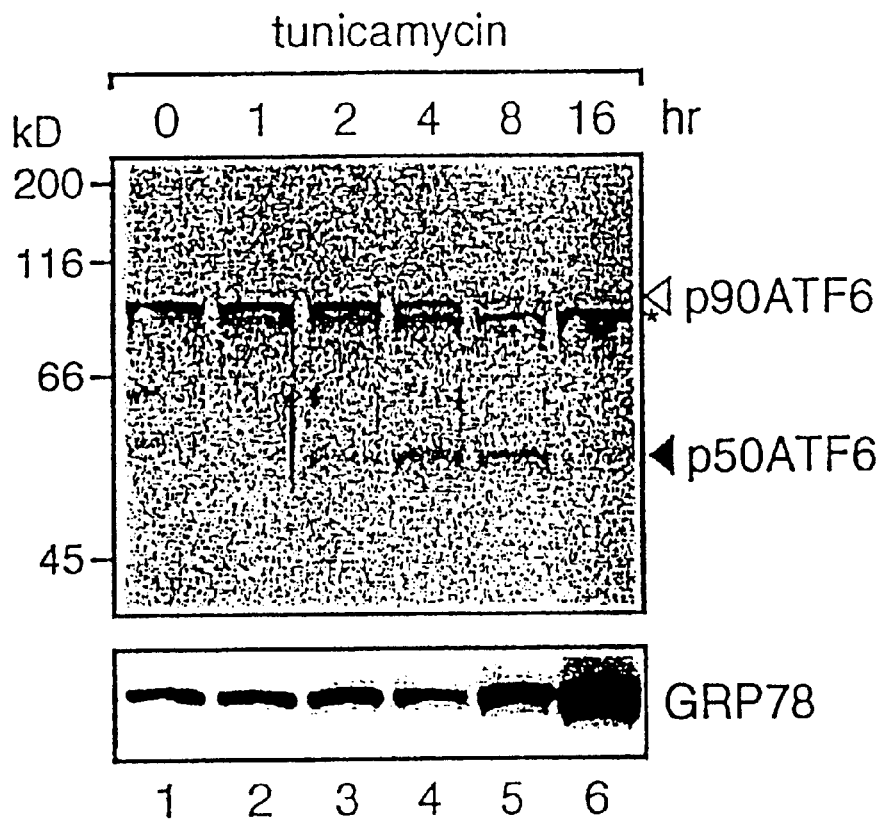
FIG. 20 shows immunoblotting analysis for ATF6. HeLa cells cultured in a 60-mm dish so as to have 60% confluency were incubated in the presence of 2 μg/ml tunicamycin (TM) for the indicated period. Cells were washed with PBS, scraped with a rubber policeman, and suspended in 100 μl Laemmli's SDS sample buffer. After boiling the suspension for 5 minutes, aliquots corresponding to $1 \times 10^5$ cells were subjected to SDS-PAGE (10% gel) and analyzed by immunoblotting using an anti-ATF6 antibody, or an anti-KDEL antibody recognizing GRP78. The positions of p90ATF6 and p50ATF6 are indicated by open and closed arrows, respectively. The asterisks denote non-specific bands in which a sugar chain is not added to p90ATF6. The positions of molecular weight markers (manufactured by Bio-Rad, prestained SDS-PAGE preparations) are also shown.

As shown in FIG. 20, p50ATF6 appeared at 2 hours after the TM treatment and continued to be detected until 4 hours (lanes 3 to 5). On the other hand, p90ATF6 decreased with the passage of time after the TM treatment, showing clear reverse correlation with the increase in p50ATF6 (lanes 1 to 6). In addition, increased GRP78 expression was observed from 8 hours after the TM treatment. These results suggest that ATF6 is synthesized as a precursor protein (p90ATF6) and specifically converted to a mature protein (50ATF6) by endoplasmic reticulum stress.

Figure 21:
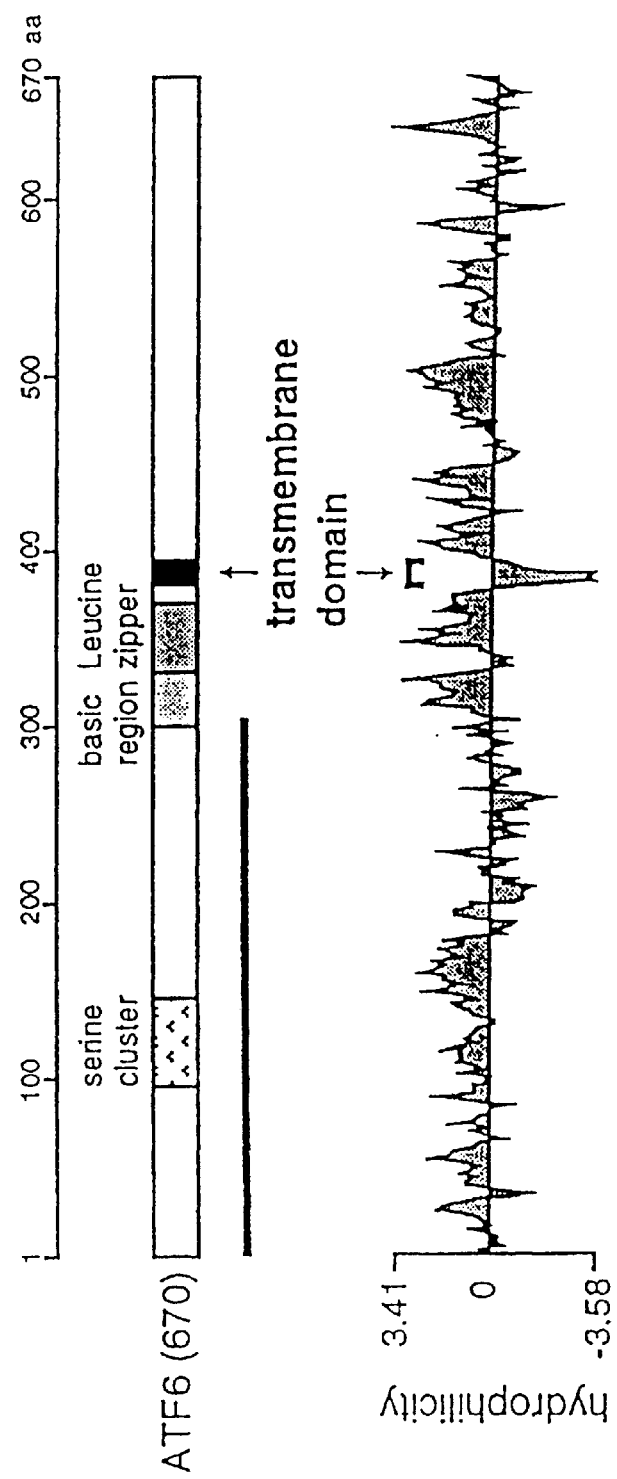
FIG. 21 shows schematic structures of ATF6 having 670 amino acids. The positions of the serine cluster, basic region, and leucine zipper [Zhu et al., Mol. Cell. Biol. 17, 4957–4966 (1997)] and the transmembrane domain identified in the present invention are indicated. The bold line represents the region (6th to 307th amino acids) in which ATF6 is fused with Escherichia coli maltose-bound protein in order to prepare an anti-AFT6 antibody. The hydropathy index was calculated by the method of Kyte and Doolittle, J. Mol. Biol. 157, 105–132 (1982).

In the experiment with respect to the passage of time shown in FIG. 20, in addition to p50ATF6, a new band with a slightly faster mobility than that of p90ATF6 was observed in TM-treated HeLa cells, whereby suggesting the possibility that p90ATF6 was modified by glycosylation and hence associated with the endoplasmic reticulum. In fact, when unstressed HeLa cells were analyzed by the indirect immunofluorescence method using the anti-B03N antibody, fine reticular stained images were observed around the nucleus. This staining pattern was the same as that observed using an anti-KDEL antibody (10C3; manufactured by Stressgen) which recognized the principal endoplasmic reticulum chaperones of GRP78 and GRP94. Furthermore, as a result of the computer-aided hydropathy analysis, it was found that as shown in FIG. 21, there exists a hydrophobic region having 21 amino acids, which is long enough to penetrate the membrane once. These results strongly support the idea that p90ATF6 is a membrane protein in the endoplasmic reticulum.

Figure 22:
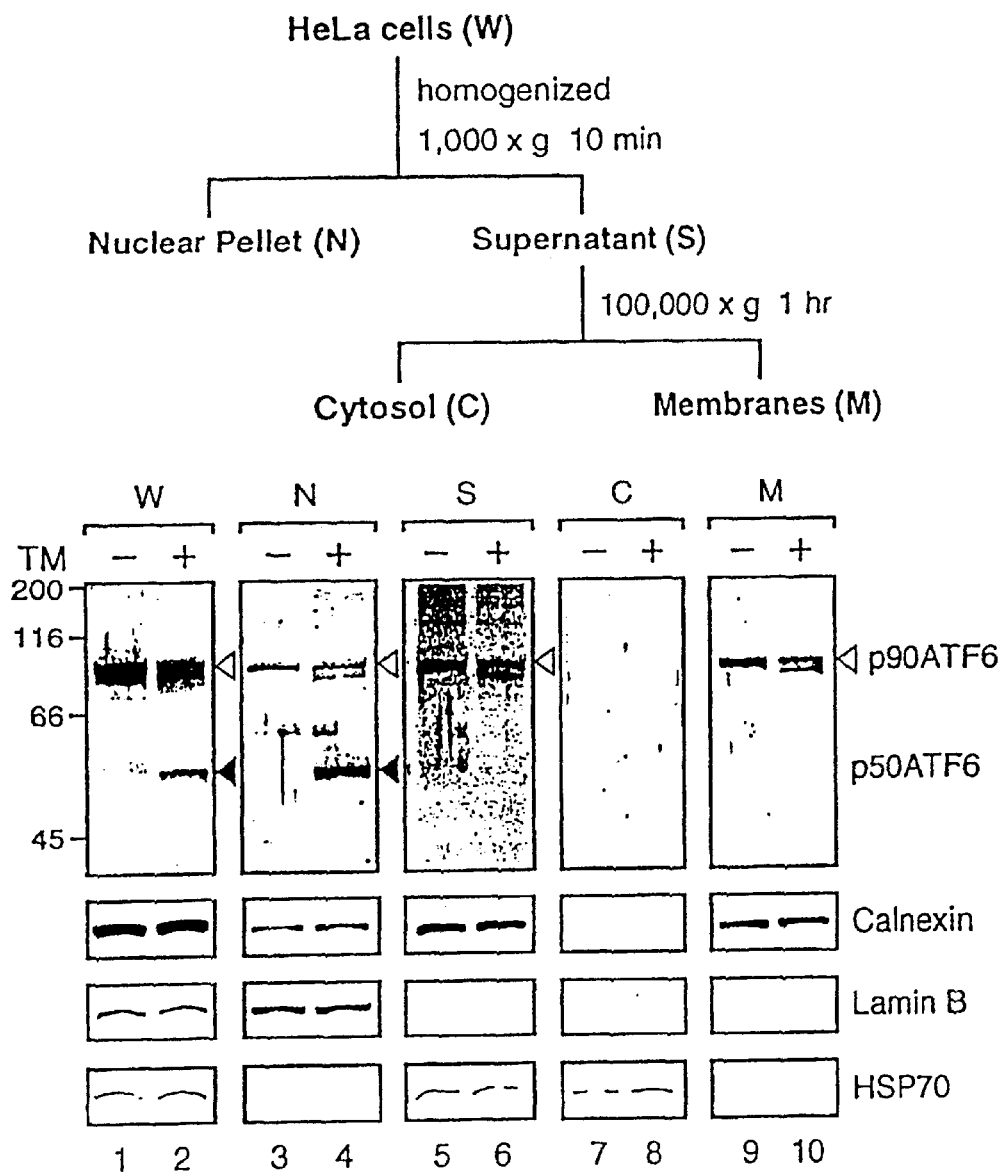
FIG. 22 shows the distribution of p90ATF6 and p50ATF6 in each of the fractions of HeLa cells. HeLa cells cultured in a 175-cm² flask so as to have 60 to 80% confluency were incubated in the absence (−) or presence (+) of 2 μg/ml tunicamycin (TM) for 4 hours. Cells were harvested, and disrupted by means of Dounce-type homogenizer, and thereafter the disrupted product was centrifuged at 1,000×g for 10 minutes to obtain nuclear pellets (in the figure, indicated by N) and supernatant (S) essentially in the same manner as described by Dignam et al. (1983). The resulting supernatant (S) was further centrifuged at 100,000×g for 1 hour to separate soluble cytosolic fraction (C) from insoluble membrane fraction (M). Aliquots of the indicated fraction as well as unfractionated HeLa cells (whole cell disruption: W) corresponding to $0.5 \times 10^5$ cells from which they originated were subjected to SDS-PAGE (10% gel) and analyzed by immunoblotting using anti-ATF6 antibody or various antibodies indicated. The positions of p90ATF6 and p50ATF6 are indicated as open arrows and closed arrows, respectively.

Next, a homogenate of HeLa cells treated with or without TM for 4 hours was fractionated by centrifugation to evaluate the localization of p90ATF6 and p50ATF6 (FIG. 22). By the first low-speed centrifugation, the majority of p90ATF6 was recovered in the soluble fraction (lane 5), whereas p50ATF6 was fractionated selectively in the nuclear fraction (lane 4), similarly to the nuclear protein lamin B. By the subsequent high-speed centrifugation, whole p90ATF6 was collected in the membrane fraction (lane 9). Although the distribution pattern of p90ATF6 was substantially identical to that of calnexin, an endoplasmic reticulum transmembrane chaperone, it completely differed from that of lamin B or the cytosolic protein HSP70. Lamin B and HSP70 were detected using an anti-lamin B antibody (manufactured by Santa Cruz) and an anti-HSP70 antibody (C92F3A-5; manufactured by Stressgen), respectively.

Example 9

Topology of p90ATF6

Figure 23:
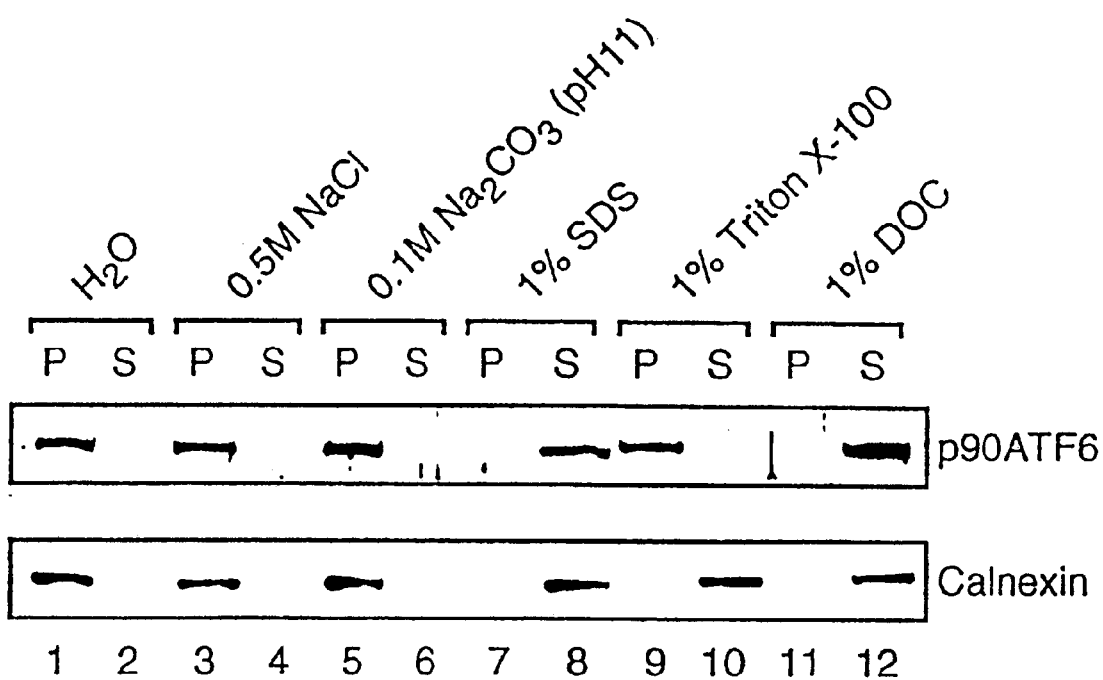
FIG. 23 shows a degree of solubilization of p90ATF6. 1,000×g supernatant (S) fraction prepared from unstressed HeLa cells obtained in the same manner as in FIG. 22 was mixed with 0.1 times by volume of one solution selected from the group consisting of the following solutions: H$_2$O, 5M NaCl, 1 M Na$_2$CO$_3$ (pH 11.0), 10% SDS, 10% Triton X-100, or 10% sodium deoxycholate (DOC). After incubation at room temperature for 15 minutes, the mixture was centrifuged at 100,000×g for 1 hour to separate supernatant (S) from pellets (P). Thereafter, the resulting sample was subjected to SDS-PAGE (10% gel) and immunoblotted using an anti-ATF6 antibody or an anti-N-terminus of calnexin antibody.

A test was carried out in order to determine whether p90ATF6 is a peripheral or integral membrane protein. The soluble fraction obtained by low-speed centrifugation was subjected to various treatments, and subsequently fractionated by high-speed centrifugation. Immunoblotting was carried out using the purified ATF6 antibody. As a result, as shown in FIG. 23, in a treatment with 0.5 M NaCl or 0.1 M $Na_2CO_3$ (pH 11), in which peripheral membrane proteins were extracted, p90ATF6 was not released from the membrane as well as the integral membrane protein calnexin. In contrast, p90ATF6 and calnexin were both released in the soluble fraction by a detergent, such as 1% SDS or 1% sodium deoxycholate (DOC). 1% Triton X-100 may cause aggregation of p90ATF6.

Figure 24:
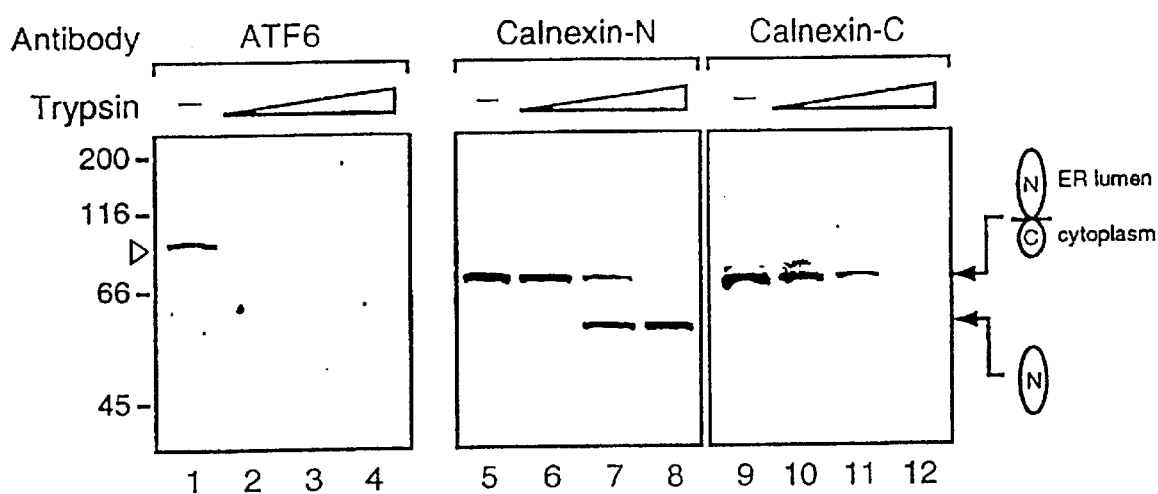
FIG. 24 shows topology of p90ATF6. The 1,000×g supernatant (S) fraction prepared from unstressed HeLa cells (50 μg proteins) was incubated with increasing amounts of trypsin (0 μg for lanes 1, 5 and 9, 0.1 μg for lanes 2, 6 and 10, 0.3 μg for lanes 3, 7 and 11, and 1.0 μg for lanes 4, 8 and 12) at room temperature for 15 minutes. Digestion was terminated by addition of an equal volume of 2×Laemmli's SDS sample buffer followed by boiling for 5 minutes. Samples were subjected to SDS-PAGE (10% gel), and analyzed by immunoblotting with anti-ATF6 antibody (lanes 1 to 4), anti-N-terminus of calnexin antibody (Calnexin-N, lanes 5 to 8), or anti-C-terminus of calnexin (Calnexin-C, lanes 9 to 12) antibody. The positions of p90ATF6 are indicated by an arrow. The positions of a full-length calnexin and its truncated form lacking the cytoplasmic domain are shown schematically.

Next, the orientation of p90ATF6 to the membrane was examined by trypsin treatment (FIG. 24). Trypsin digestion was monitored using calnexin, a type I membrane protein, as a control, and using an antibody (manufactured by Stressgen) recognizing the calnexin N-terminal region in the endoplasmic reticulum lumen (calnexin-N) or the calnexin C-terminal region in the cytosol (calnexin-C). At the trypsin concentrations reducing the amount of full-length calnexin, the appearances of indigestible calnexin fragment were not observed with the anti-calnexin C-antibody (lanes 11 and 12), while the appearance of a fragment of a size corresponding to the calnexin N-terminal region was observed with the anti-calnexin N antibody (lanes 7 and 8). This result demonstrates that the region of the lumenal side was resistant to trypsin digestion as expected.

Under these experimental conditions, p90ATF6 disappeared at the lowest trypsin concentration examined, and no fragment corresponding to 50 kDa molecular weight could be detected by the anti-ATF6 antibody recognizing the N-terminal region of ATF6 (lane 2). This result strongly suggests that p90ATF6 is a type II membrane protein with its N-terminal region oriented toward the cytosol.

Example 10

Intracellular Localization of p50ATF6

In order to determine whether or not the intracellular localization status is altered by converting p90ATF6 to p50ATF6, a test was carried out by an indirect immunofluorescence method using HeLa cells transformed with the ATF6 expression plasmid. Plasmid pCGN-ATF6 [Zhu et al., *Mol. Cell. Biol*. 17, 4957–4966 (1997)] capable of expressing full-length ATF6 was obtained from Dr. Prywes of Columbia University (hereinafter referred to as pCGN-ATF6(670)). This plasmid was prepared by inserting ATF6 cDNA to the XbaI site of the expression vector pCGN for animal cells, and expressed ATF6 with the influenza virus hemagglutinin (HA) epitope bound to the N-terminus thereof under the control of the cytomegalovirus promoter. The plasmids pCGN-ATF6(402), pCGN-ATF6(373), pCGN-ATF6(366) and pCGN-ATF6(330), all of which cause the expression of an N-terminal fragment of ATF6, were constructed by preparing the regions encoding amino acids 1st to 402nd, 1st to 373rd, 1st to 366th and 1st to 330th, respectively, by PCR, and inserting them, together with the stop codon (TAG), in the XbaI site of pCGN.

Figure 25:
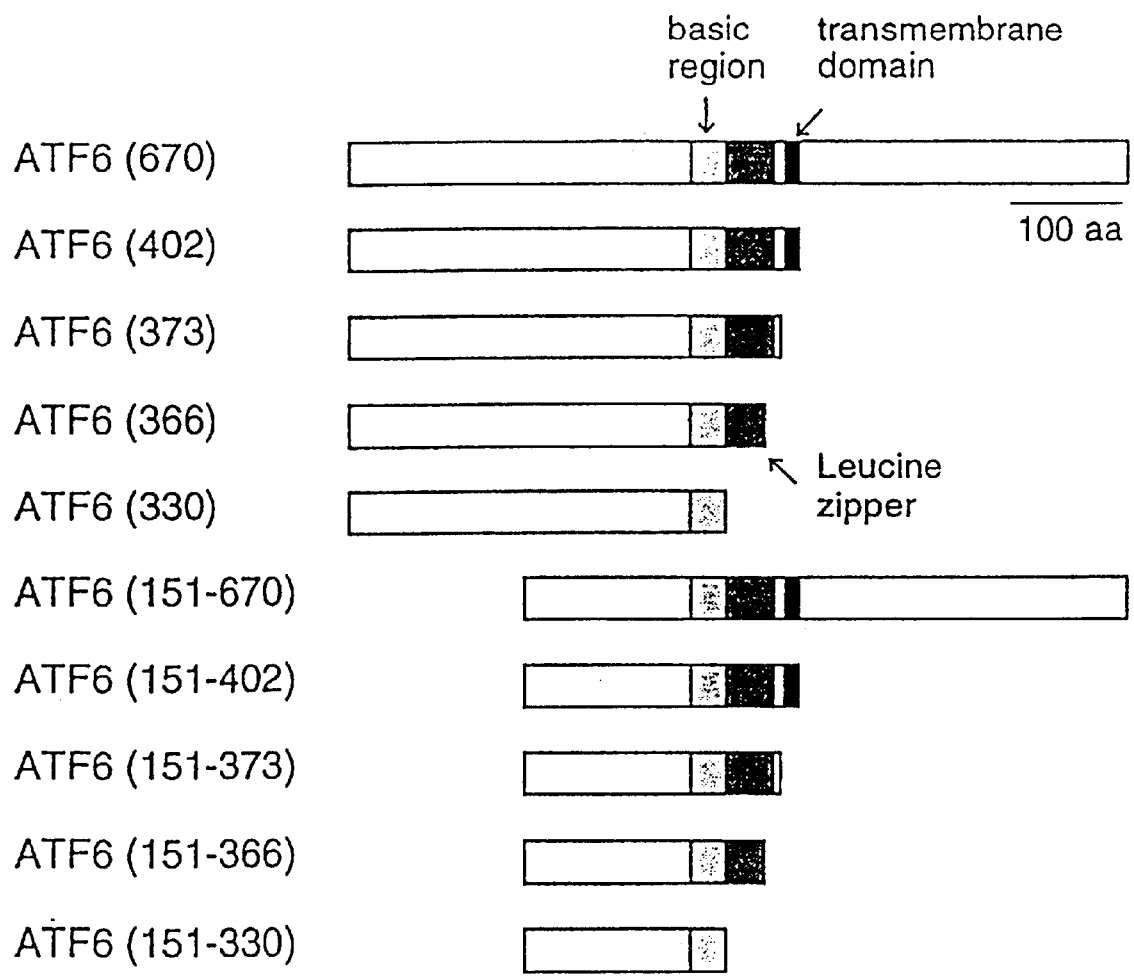
FIG. 25 shows schematic structures of full-length ATF6 cDNA, ATF6(670), which is inserted into mammalian expression vector pCGN and various deletion mutants. In the figure, the positions of the basic region, the leucine zipper region and the transmembrane domain are indicated. HA epitope is bound to N-terminal each of various deletion mutants.

The structures of the ATF6 and various mutants expressed from these plasmids are schematically shown in FIG. 25. ATF(402) lacks the majority of the C-terminal lumenal domain but retains the transmembrane domain ($V^{334}$-$L^{398}$), whereas the three mutants ATF6(373), ATF6(366) and ATF6 (330) lack both the lumenal domain and the transmembrane domain. ATF6(373) comprises the basic region ($R^{308}$-$R^{330}$) and the leucine zipper ($L^{334}$-$L^{369}$) in their entireties. ATF6 (366) comprises the entire basic region and the majority of the leucine zipper region. ATF(330) comprises the basic region but completely lacks the leucine zipper region. All these proteins have the HA epitope bound to the N-terminus thereof.

Next, the HeLa cells were transiently transformed with expression plasmids for these ATF6s and various mutants, respectively, and the resulting transformant was analyzed by the indirect immunofluorescence method using an anti-HA epitope antibody (Y11; manufactured by Santa Cruz). The expression of ATF6(670) and ATF6(402), both of which have the transmembrane domain, was found to be localized in the endoplasmic reticulum, showing the same staining pattern as that of the fluorescent staining using an anti-KDEL antibody.

On the other hand, in cells expressing ATF6(373), ATF6 (366) or ATF6(330), which are mutant ATF6 members lacking both the lumenal domain and the transmembrane domain, the nucleus was clearly stained with the anti-HA antibody. These results strongly suggested that p90ATF6 is embedded in the endoplasmic reticulum membrane, whereas p50ATF6 is cleaved on the N-terminal side of the transmembrane domain and localized in the nucleus.

Example 11

Deduction of Cleavage Site in p50ATF6 Production

In order to deduce the cleavage site involved in p50ATF6 production in response to endoplasmic reticulum stress, the HeLa cells transfected with various C-terminal deletion mutants prepared in Example 10 were analyzed by immunoblotting. The results are shown in FIG. 26. In the cells transfected with pCGN-ATF6(670), the two protein bands (lane 2) detected at a position corresponding to about 50 kDa molecular weight served as appropriate molecular weight markers for p50ATF6. These proteins are assumed to be p50ATF6 produced by proteolysis constitutively activated by overexpression of HA-labeled ATF6(670) in the transfected cells. The bands of fast mobility are assumed to have resulted from the loss of the HA label. It is found from the mobility comparison of various C-terminal deletion mutants on SDS-PAGE that the size of p50ATF6 approximates that of ATF6(373), suggesting that when cells are subjected to endoplasmic reticulum stress, p90ATF6 is cleaved between bZIP and the transmembrane domain to produce p50ATF6.

Example 12

Transcription-activating Domain of ATF6

Figure 27:
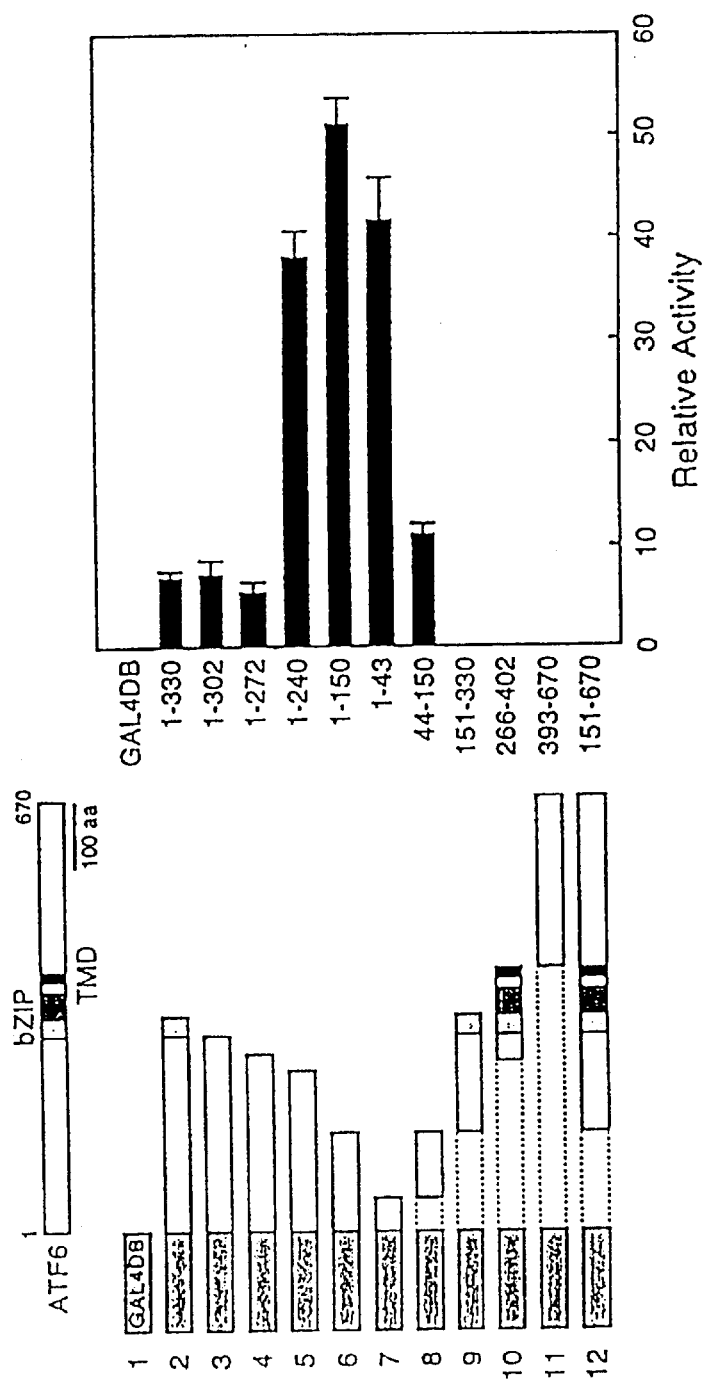
FIG. 27 shows the analytic results of transcription-activating domain of ATF6. Left panel shows schematic structures of ATF6 and fusion proteins between various ATF6 subregions and the DNA-binding domain (1st to 147th amino acids) of yeast Gal4p (GAL4DB). In the figure, the dotted lines denote the region deleted from the construct. The positions of the basic leucine zipper region (bZIP) and the transmembrane domain (TMD) are indicated. Right panel shows transcription activities of various fusion proteins. HeLa cells in a 24-well plate were transiently transfected with each of the fusion protein expression plasmids together with the reporter plasmid pG51uc containing five Gal4p binding sites upstream of the firefly luciferase gene. Constitutively expressed luciferase activities were determined and normalized as described in Examples. The relative activities are indicated as the mean±standard deviations (bars) from-four independent experiments (triplicate determinations). The positive control supplied by the manufacturer (pBIND-Id plus pACT-MyoD control vectors; manufactured by Promega) showed the relative activity of 4.6±0.3 in this assay.

Various PCR-amplified regions of ATF6 were inserted into the XbaI site of the plasmid pBIND (manufactured by Promega), which expresses the DNA-binding domain (amino acids 1st to 147th, referred to as "GAL4DB") of the yeast transcription factor Gal4p under the control of the cytomegalovirus promoter, to yield plasmids for expressing fusion proteins of the ATF6 fragments with GAL4DB. These expression plasmids were transiently introduced into HeLa cells together with the reporter plasmid pG5luc (manufactured by Promega) containing five Gal4p binding sites just upstream of the adenovirus major late promoter to determine their ability of activating the transcription of the luciferase gene. As shown in FIG. 27, the transcription-activating ability was mapped to an N-terminal 150-amino acid region (lines 6 and 9 to 12), especially demonstrating the great contribution of the 43 N-terminal amino acids (lines 6 to 8). The presence of a transcription-activating domain at the N-terminus ensures the function of p50ATF6 as a transcription factor in the nucleus.

Example 13

Transcriptional Activity of C-terminus Deletion Mutants of ATF6

Using HeLa cells co-transfected with the reporter plasmid pGL3-G78(−132) [see Example 1 (FIG. 6, line 2)] resulting from ligation of the firefly luciferase gene to downstream of the human GRP78 promoter ([−132 to +7], numbered on the basis of the translation initiation point taken as +1) and the expression plasmid for the ATF6 C-terminal deletion mutant of Example 10, the effects of each of the overexpressed C-terminal deletion mutants of ATF6 on ERSE-mediated transcriptional activation were evaluated.

As a result, it was found that when the full-length ATF6, namely ATF(670), is transiently overexpressed using pCGN-ATF6(670), the transcription of the luciferase gene from the GRP78 promoter having ERSE, is constitutively activated in the absence of endoplasmic reticulum stress (FIG. 28, line 2), as in the results obtained in Example 5 (FIG. 14). The higher relative luciferase activity in comparison with the level obtained in Example 5 (FIG. 14) was attributed to the expression of more ATF6 in the cells transfected with pCGN-ATF6 than in those transfected with pcDNA-ATF6. Further, the constitutive activation of transcription of the luciferase gene can be well explained by the fact that a p50ATF6-like protein was constitutively produced in the aforementioned cells transfected with pCGN-ATF6(670) (see FIG. 26, lane 2). Similarly, the reporter luciferase activity was also constitutively enhanced by overexpression of endoplasmic reticulum-localized ATF6(402) [open bar on line 3 in FIG. 28].

Figure 28:
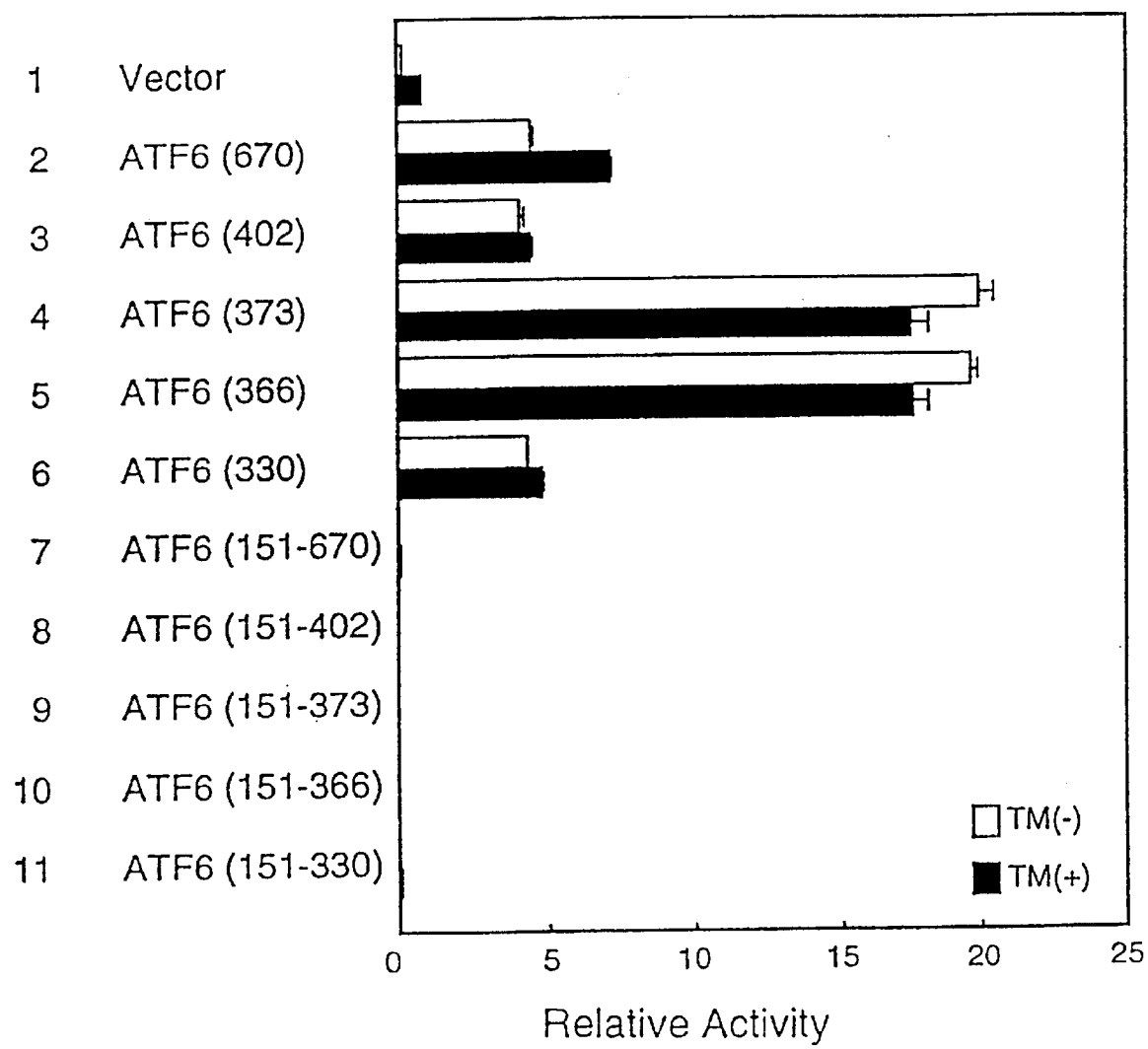
FIG. 28 shows effects of overexpression on full-length ATF6, C-terminal deletion mutants and transcription-activating domain deletion mutant on ERSE-mediated transcription. HeLa cells in a 24-well plate were transiently transfected with a reporter plasmid pGL-G78(−132) capable of expressing firefly luciferase gene under the control of human GRP78 promoter, together with pCGN vector alone (Vec) or each of ATF6 expression plasmids. Transfected cells were treated with (closed bars) or without (open bars) 2 μg/ml tunicamycin (TM) for 16 hours prior to measuring luciferase activity. The relative activities are indicated as the mean±standard deviations (bars) from four independent experiments (triplicate determinations).

The results as shown by the open bars on lines 4 and 5 and the open bars on lines 2 and 3 in FIG. 28 demonstrate that increased luciferase activity by 5-fold or more over that obtained with the endoplasmic reticulum-localized ATF6 ATF(670) or ATF(402) is obtained by overexpressing the nucleus-localized ATF6 mutants ATF6(373) and ATF6(366). These results agree with the fact that the nuclear protein p50ATF6 shows the activated form of ATF6.

On the other hand, another nucleus-localized ATF6(330) showed markedly lower activity than ATF6(373) or ATF (366), despite having nearly the same expression level (FIG. 26), demonstrating the importance of the leucine zipper in the transcriptional activity of ATF6 (compare line 6 with lines 4 and 5 in FIG. 28).

Example 14

Transcription-activating Domain Deletion Mutants of ATF6

Each of pCGN-ATF6(151–670), pCGN-ATF6(151–402), pCGN-ATF6(151–373), pCGN-ATF6(151–366) and pCGN-ATF6(151–330), which expressed mutant ATF6 lacking a region of amino acids 1st to 150th from the N-terminal of ATF6 or the mutants prepared in Example 10, was constructed by preparing the regions encoding amino acids 151st to 670th, 151st to 402nd, 151st to 373rd, 151st to 366th and 151st to 330th, respectively, by PCR, and inserting each region, together with the stop codon, in the XbaI site of pCGN (see FIG. 25).

Being expressed from these plasmids, each of ATF6 (151–670), ATF6(151–402), ATF6(151–373), ATF6 (151–366) and ATF6(151–330) resulted from the deletion of the N-terminal 150 amino acids ($M^1$-$L^{150}$) from ATF6(670), ATF6(402), ATF6(373), ATF6(366) and ATF6(330), respectively.

In the same manner as in Example 10, HeLa cells were transiently transformed with each expression plasmid for an ATF6 transcription-activating domain deletion mutant, and the intracellular localization of the ATF6 transcription-activating domain deletion mutant expressed was evaluated by the indirect immunofluorescence method using an anti-HA epitope antibody (Y11; manufactured by Santa Cruz). As a result, ATF6(151–670) and ATF6(151–402) were found to be localized in endoplasmic reticulum, as were the corresponding ATF6(670) and ATF6(402), respectively. In addition, ATF6(151–373), ATF6(151–366) and ATF6 (151–330) were all localized in the nucleus, as were ATF6 (373), ATF6(366) and ATF6(330).

Next, in the same manner as in Example 13, the effect of the overexpression of each ATF6 transcription-activating domain deletion mutant on ERSE-mediated transcriptional activation was evaluated by co-transfection with the reporter plasmid pGL3-G78(−132).

As a result, as shown on lines 7 to 11 in FIG. 28, all ATF6 transcription-activating domain deletion mutants strongly suppressed the expression of the reporter gene to a level equal to or less than that when the control pCGN vector (line 1) is used. ATF6(151–373), ATF6(151–366) and ATF6 (151–330) were shown to act dominant-negatively on endogenous p50ATF6 in the nucleus. On the other hand, ATF6(151–670) and ATF6(151–402) were assumed to act dominant-negatively on endogenous p50ATF6 by inducing endoplasmic reticulum stress by their overexpression in the endoplasmic reticulum, followed by migration into the nucleus of the resulting p50ATF6 lacking the transcription-activating domain.

Example 15

Conversion of p110CREB-RP to p60CREB-RP by Endoplasmic Reticulum Stress

In order to elucidate whether or not a full-length CREB-RP (p110CREB-RP) is converted to p60CREB-RP by endoplasmic reticulum stress, quantitative changes in p110CREB-RP and p60CREB-RP in TM-treated HeLa cells were evaluated with the passage of time by immunoblotting using a purified CREB-RP antibody. The CREB-RP antibody was prepared by immunizing a rabbit with a fusion protein of a region of amino acids 1st to 307th of CREB-RP with GST, expressed in *Escherichia coli*, and used after absorption with GST and bacterial proteins and affinity purification with the GST-CREB-RP fusion protein.

When the conversion of p90ATF6 to p50ATF6 and the amount of the target protein GRP78 were also examined in the same manner as in Example 8, p60CREB-RP was found to appear 2 hours after the TM treatment, and, unlike p50ATF6, to be persistently expressed thereafter, as shown in FIG. 29.

Example 16

Activated Form of CREB-RP

From the CREB-RP expression plasmid prepared in Example 4, a DNA fragment encoding a region of amino acids 1st to 389th of CREB-RP was prepared by PCR, and inserted into the HindIII site of the pcDNA3.1(+) vector. Being expressed from this plasmid, CREB-RP(1–389) comprises the N-terminus through the basic region and the leucine zipper region of CREB-RP, corresponding to p60CREB-RP as converted from p110CREB-RP by endoplasmic reticulum stress.

The CREB-RP(1–389) expression plasmid and a reporter plasmid resulting from ligation of the luciferase gene to downstream of the GRP78 promoter or mutant GRP78 promoter were introduced into the HeLa cells to evaluate the effect of CREB-RP(1–389) overexpression on ERSE-mediated transcriptional activation.

Figure 30:
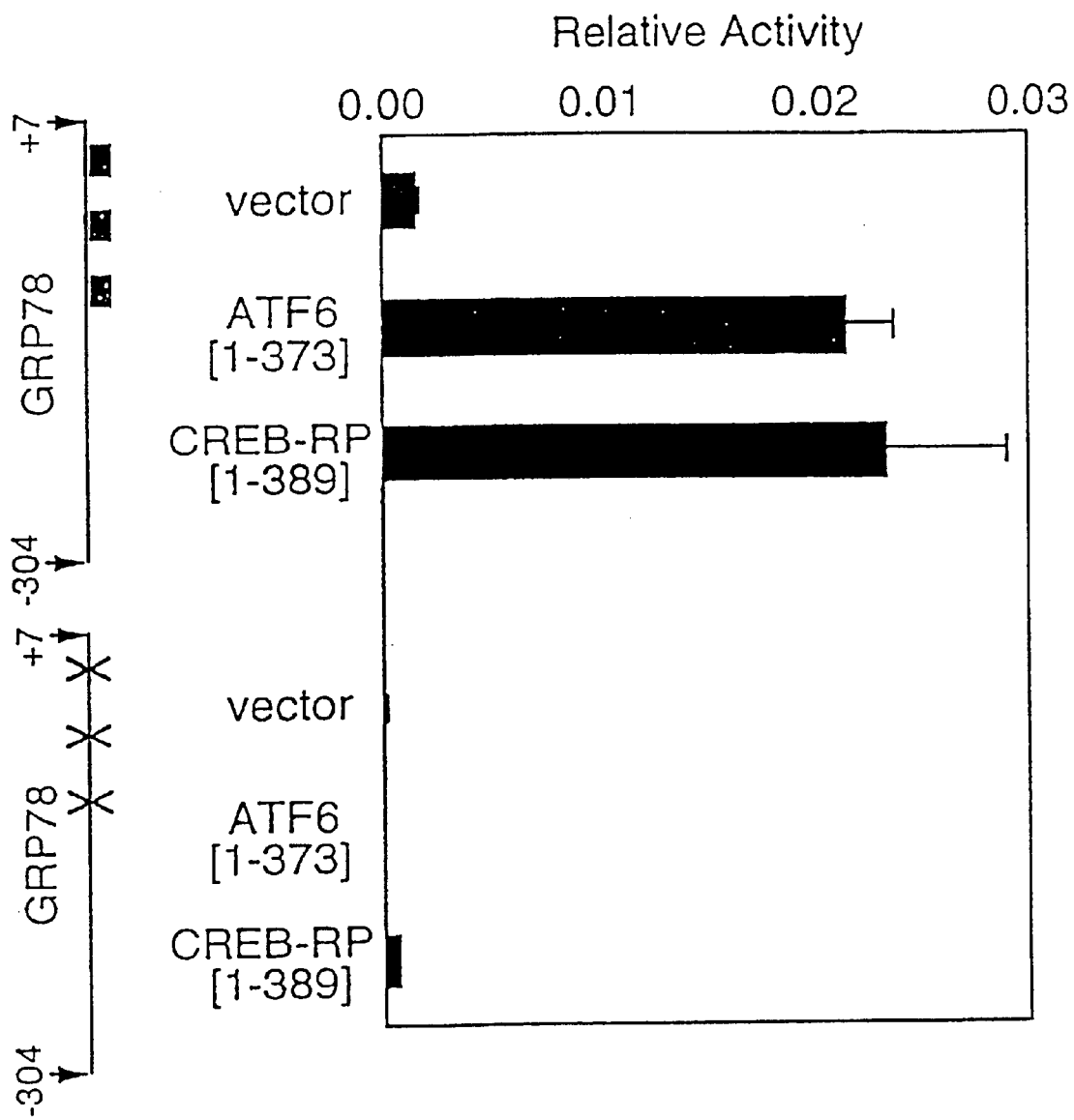
FIG. 30 shows effects of overexpression of p60CREB-RP and p50ATF6 on ERSE-mediated transcription. In a 96-well plate, the HeLa cells were transiently transformed with a reporter plasmid pGL-G78(−132) for expressing firefly luciferase gene under the control of a human GRP78 promoter together with pcDNA3.1 vector which has no inserts or with ATF6(1–373) expression plasmid or with CREB-RP (1–389) expression plasmid. Relative activity is indicated by the mean±standard deviation (bars), based on four independent experiments (each triplicate determinations).

As shown in FIG. 30, the overexpression of CREB-RP (1–389), which is assumed to correspond to p60CREB-RP, constitutively activated the transcription, in the same manner as in p50ATF6. Because this transcriptional activation is not observed when mutant ERSE is used, it is found to be ERSE-dependent.

Example 17

Suppressive Form of CREB-RP

A DNA fragment encoding a region of amino acids 308th to 386th of CREB-RP, in which Met was added to the N-terminus thereof, was prepared from the CREB-RP expression plasmid prepared in Example 4 by PCR, and the DNA fragment was inserted into the HindIII site of the pcDNA3.1(+) vector. Being expressed from this plasmid, CREB-RP(308–386) does not contain the transcription-activating domain present in the N-terminal region of CREB-RP but only selectively comprises the basic region and the leucine zipper region.

Figure 31:
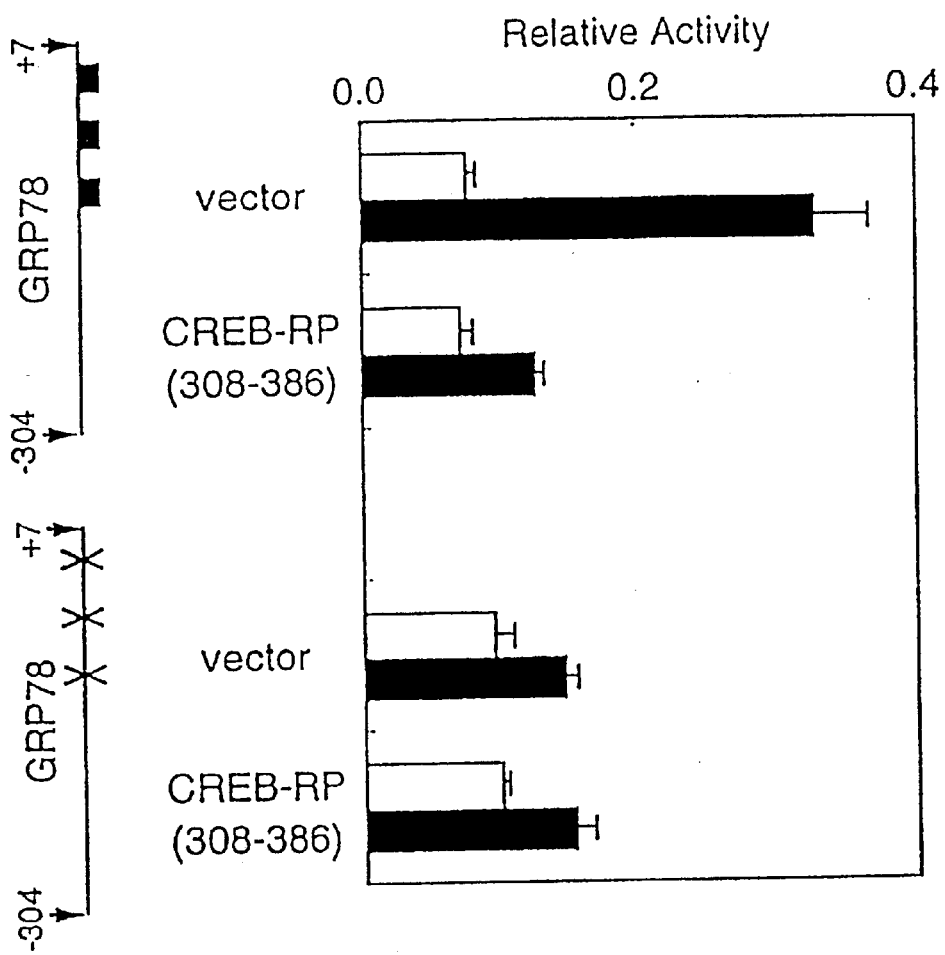
FIG. 31 shows effects of overexpression of a deletion mutant of CREB-RP transcription-activating domain on ERSE-mediated transcription. In a 96-well plate, the HeLa cells were transiently transformed using a reporter plasmid pGL-G78(−132) for expressing firefly luciferase gene under the control of a human GRP78 promoter together with pcDNA3.1 vector which has no inserts or with CREB-RP (308–386) expression plasmid. Transfected cells were treated with (closed bars) or without 2 μg/ml tunicamycin (open bars) for 16 hours before luciferase activities were determined. Relative activity is indicated by the mean±standard deviation (bars), based on four independent experiments (each triplicate determinations).

In the same manner as in Example 16, the effect of CREB-RP(308–386) overexpression on ERSE-mediated transcriptional activation was evaluated. As shown in FIG. 31, the ERSE-dependent transcriptional induction by the TM treatment was strongly suppressed. The results demonstrate that CREB-RP(308–386) acts dominant-negatively on the endogenous endoplasmic reticulum stress transcription factor.

Figure 32:
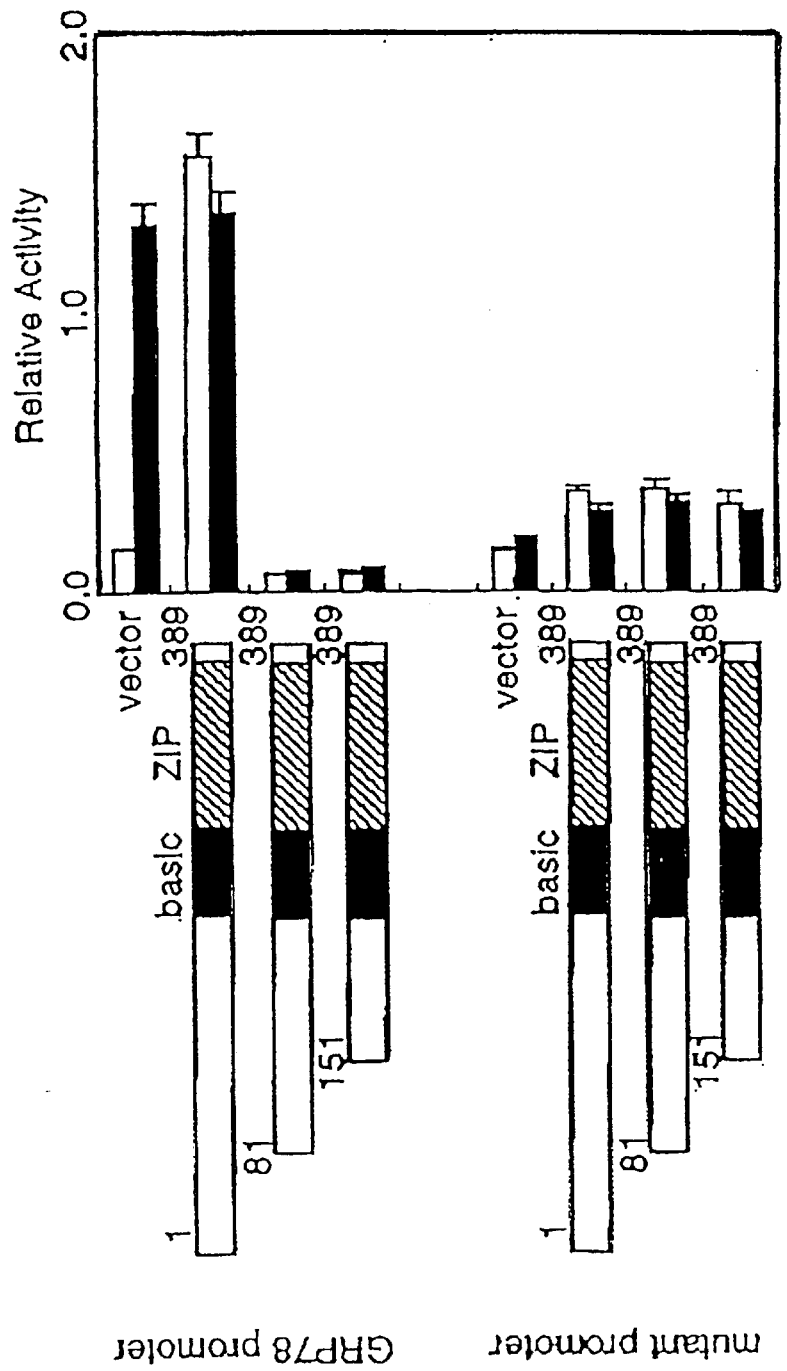
FIG. 32 shows effects of overexpression of deletion mutants of CREB-RP transcription-acting domain, CREB-RP(151–389) and CREP-RP(81–389) on ERSE-mediated transcription. In the figure, closed bars and open bars indicate the same as those in FIG. 31.

In addition, in the same manner as in Example 16, the effect of overexpression of CREB-RP(81–389) or CREB-RP(151–389) on ERSE-mediated transcriptional activation was evaluated. Here, each of CREB-RP(81–389) and CREB-RP(151–389) lacks transcription-activating domain. As shown in FIG. 32, the ERSE-dependent transcriptional induction by the TM treatment was strongly suppressed. The results demonstrate that each of CREB-RP(81–389) and CREB-RP(151–389) dominant-negatively acts on the endogenous endoplasmic reticulum stress transcription factor.

SEQUENCE LISTING FREE-TEXT

In SEQ ID NO: 1, "n" is A or C or G or T. The sequence as shown in SEQ ID NO: 1 is the ERSE1 consensus sequence.

In SEQ ID NO: 2, "n" is A or C or G or T. The sequence as shown in SEQ ID NO: 2 is the ERSE2 consensus sequence.

In SEQ ID NO: 3, "n" is A or C or G or T. The sequence as shown in SEQ ID NO: 3 is the ERSE3 consensus sequence.

INDUSTRIAL APPLICABILITY

The endoplasmic reticulum stress transcription factor is capable of regulating increase or decrease of expression of endoplasmic reticulum chaperone genes. According to the method for controlling expression of endoplasmic reticulum chaperones of the present invention, the increase or decrease of expression of endoplasmic reticulum chaperone genes can be regulated. Further, treatment or prophylaxis of cancers, arteriosclerosis, cystic fibrosis, ischemic diseases, wounds or ulcers is made possible by the method for controlling expression of endoplasmic reticulum chaperones of the present invention. Moreover, by applying the method for controlling expression mentioned above to expression of a foreign useful protein, there are exhibited excellent effects that the foreign useful protein retains correct conformation, and that the foreign protein can be expressed at a high level.

EQUIVALENT

Those skilled in the art will recognize, or be able to ascertain using simple routine experimentation, many equivalents to the specific embodiments of the invention described in the present specification. Such equivalents are intended to be encompassed in the scope of the following claims.

We claim:

1. An isolated nucleic acid encoding an activated form of ATF6, or the complementary strand thereto, wherein said activated form of ATF6 is p50ATF6 resulting from processing by endoplasmic reticulum stress, a polypeptide obtainable by expression of DNA encoding p50ATF6, or a polypeptide comprising a region of 1st to 373rd amino acids or a region of 1st to 366th amino acids in ATF6, and wherein said nucleic acid is selected from the group consisting of:
   (a) a nucleic acid having a nucleotide sequence encoding an amino acid sequence as shown in amino acid numbers: 1 to 373 in SEQ ID NO: 32;
   (b) a nucleic acid having a nucleotide sequence encoding an amino acid sequence as shown in amino acid numbers: 1 to 366 in SEQ ID NO: 32;
   (c) a nucleic acid having a nucleotide sequence as shown in base numbers: 69 to 1187 in SEQ ID NO: 31;
   (d) a nucleic acid having a nucleotide sequence as shown in base numbers: 69 to 1166 in SEQ ID NO: 31; and
   (e) a nucleic acid capable of hybridizing to a strand complementary to the nucleic acid of any one of (a) to (d) under stringent conditions at 68° C. in aqueous with 6×sodium chloride-sodium citrate (SSC) or 42° C. in 50% formamide with 6×SSC, wherein said nucleic acid encoding an activated form of ATF6 encodes a polypeptide showing an activity for enhancing expression of endoplasmic reticulum chaperone genes without conversion of the polypeptide in the presence of endoplasmic reticulum stress, or the complementary strand thereto.

2. An isolated nucleic acid encoding a suppressive form of ATF6, or the complementary strand thereto, wherein said suppressive form of ATF6 is a polypeptide resulting from disruption of a region of 1st to 150th amino acids in ATF6, or a polypeptide resulting from disruption of a region of 1st to 150th amino acids in an activated form of ATF6 selected from the group consisting of:

(i) p50ATF6 resulting from processing by endoplasmic reticulum stress, (ii) a polypeptide obtainable by expression of DNA encoding p50ATF6, and (iii) a polypeptide comprising a region of 1st to 373rd amino acids or a region of 1st to 366th amino acids in ATF6, and wherein the nucleic acid is selected from the group consisting of:

(1) a nucleic acid having a nucleotide sequence encoding an amino acid sequence as shown in amino acid numbers: 151 to 670 in SEQ ID NO: 32;

(2) a nucleic acid having a nucleotide sequence encoding an amino acid sequence as shown in amino acid numbers: 151 to 373 in SEQ ID NO: 32;

(3) a nucleic acid having a nucleotide sequence encoding an amino acid sequence as shown in amino acid numbers: 151 to 366 in SEQ ID NO: 32;

(4) a nucleic acid having a nucleotide sequence as shown in base numbers: 519 to 2078 in SEQ ID NO: 31;

(5) a nucleic acid having a nucleotide sequence as shown in base numbers: 519 to 1187 in SEQ ID NO: 31;

(6) a nucleic acid having a nucleotide sequence as shown in base numbers: 519 to 1166 in SEQ ID NO: 31; and (7) a nucleic acid capable of hybridizing to the strand complementary to the nucleic acid of any one of (1) to (6) under stringent conditions at 68° C. in aqueous with 6×sodium chloride-sodium citrate (SSC) or 42° C. in 50% formamide with 6×SSC, wherein said nucleic acid encoding a suppressive form of ATF6 encodes a polypeptide showing an activity for decreasing expression of endoplasmic reticulum chaperone genes without conversion of a protein in the presence of endoplasmic reticulum stress, or the complementary strand thereto.

* * * * *